United States Patent
Sakamoto et al.

(10) Patent No.: US 9,580,402 B2
(45) Date of Patent: Feb. 28, 2017

(54) SALT, ACID GENERATOR, PHOTORESIST COMPOSITION, AND METHOD FOR PRODUCING PHOTORESIST PATTERN

(71) Applicant: SUMITOMO CHEMICAL COMPANY, LIMITED, Tokyo (JP)

(72) Inventors: Hiromu Sakamoto, Osaka (JP); Koji Ichikawa, Osaka (JP)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 0 days.

(21) Appl. No.: 14/988,156

(22) Filed: Jan. 5, 2016

(65) Prior Publication Data

US 2016/0200702 A1   Jul. 14, 2016

(30) Foreign Application Priority Data

Jan. 8, 2015 (JP) .................... 2015-002027

(51) Int. Cl.

| | | |
|---|---|---|
| G03F 7/004 | (2006.01) | |
| G03F 7/20 | (2006.01) | |
| G03F 7/38 | (2006.01) | |
| C07C 303/32 | (2006.01) | |
| C07C 309/04 | (2006.01) | |
| C07C 309/06 | (2006.01) | |
| C07C 309/12 | (2006.01) | |
| C07C 309/17 | (2006.01) | |
| C07C 309/19 | (2006.01) | |
| C07D 327/02 | (2006.01) | |
| C07D 327/04 | (2006.01) | |
| C07D 327/06 | (2006.01) | |
| C07D 333/46 | (2006.01) | |
| C07D 335/02 | (2006.01) | |
| C07D 337/04 | (2006.01) | |
| C07D 307/93 | (2006.01) | |
| G03F 7/039 | (2006.01) | |

(52) U.S. Cl.
CPC .......... *C07D 327/06* (2013.01); *C07C 303/32* (2013.01); *C07C 309/04* (2013.01); *C07C 309/06* (2013.01); *C07C 309/12* (2013.01); *C07C 309/17* (2013.01); *C07C 309/19* (2013.01); *C07D 307/93* (2013.01); *C07D 327/02* (2013.01); *C07D 327/04* (2013.01); *C07D 333/46* (2013.01); *C07D 335/02* (2013.01); *C07D 337/04* (2013.01); *G03F 7/0045* (2013.01); *G03F 7/0046* (2013.01); *G03F 7/0397* (2013.01); *G03F 7/0392* (2013.01); *G03F 7/2041* (2013.01); *G03F 7/38* (2013.01)

(58) Field of Classification Search
CPC .... G03F 7/0045; G03F 7/0046; G03F 7/0392; G03F 7/0397; G03F 7/2041; G03F 7/38; C07D 327/02; C07D 327/04; C07D 327/06; C07D 333/46; C07D 335/02; C07D 337/04; C07C 303/32; C07C 309/04; C07C 309/06; C07C 309/12; C07C 309/17; C07C 309/19
USPC ... 430/270.1, 326, 921, 922; 549/10, 13, 14, 549/28, 30, 62; 560/149, 256; 562/100, 562/109, 110, 113
See application file for complete search history.

(56) References Cited

U.S. PATENT DOCUMENTS

| | | |
|---|---|---|
| 2011/0117493 A1 | 5/2011 | Ichikawa et al. |
| 2011/0117494 A1* | 5/2011 | Ichikawa ............... C07C 25/18 430/270.1 |
| 2012/0122032 A1 | 5/2012 | Anryu et al. |

* cited by examiner

*Primary Examiner* — John S Chu
(74) *Attorney, Agent, or Firm* — Birch, Stewart, Kolasch & Birch, LLP

(57) ABSTRACT

A salt represented by the formula (I):

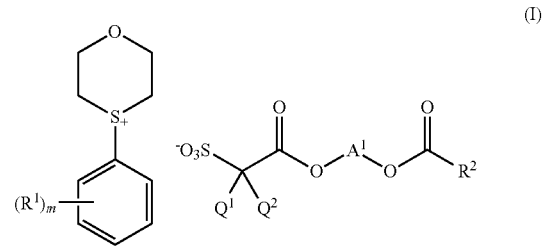

wherein
$R^1$ represents a C1 to C12 alkyl group in which a methylene group can be replaced by an oxygen atom or a carbonyl group;
$Q^1$ and $Q^2$ each independently represent a fluorine atom or a C1 to C6 perfluoroalkyl group;
$A^1$ represents a lactone ring-containing group which has 4 to 24 carbon atoms;
$R^2$ represents an acid-labile group; and
"m" represents an integer of 0 to 3.

7 Claims, No Drawings

SALT, ACID GENERATOR, PHOTORESIST COMPOSITION, AND METHOD FOR PRODUCING PHOTORESIST PATTERN

This nonprovisional application claims priority under 35 U.S.C. §119(a) on Patent Application No. 2015-002027 filed in JAPAN on Jan. 8, 2015, the entire contents of which are hereby incorporated by reference.

TECHNICAL FIELD

The present invention relates to a salt, and an acid generator, a photoresist composition, and a method for producing a photoresist pattern.

BACKGROUND ART

US2011/117493A1 discloses a salt represented by the following formula:

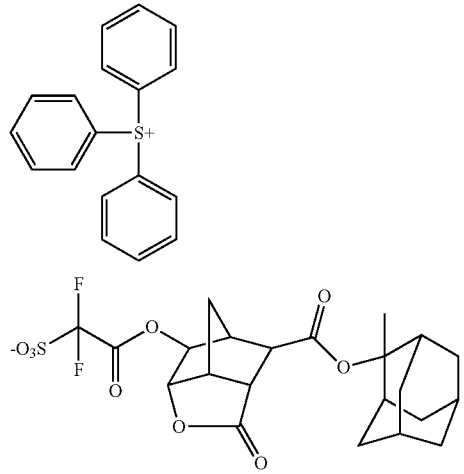

and a photoresist composition which contains the salt as an acid generator.

US2012/122032A1 discloses a salt represented by the following formula:

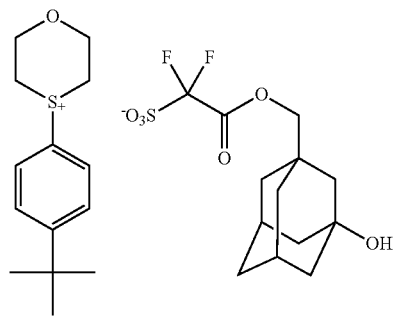

and a photoresist composition which contains the salt as an acid generator.

SUMMARY OF THE INVENTION

The present invention relates to the followings.
[1] A salt represented by the formula (I):

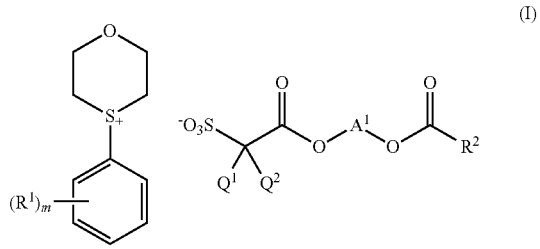

wherein
$R^1$ each independently represents a C1 to C12 alkyl group in which a methylene group can be replaced by an oxygen atom or a carbonyl group;
$Q^1$ and $Q^2$ each independently represent a fluorine atom or a C1 to C6 perfluoroalkyl group;
$A^1$ represents a lactone ring-containing group which has 4 to 24 carbon atoms;
$R^2$ represents an acid-labile group; and
"m" represents an integer of 0 to 3.
[2] The salt according to [1] wherein
$A^1$ represents a group which has a norbornanelactone ring.
[3] The salt according to [1] or [2] wherein
$R^2$ is represented by formula (R2-1)

wherein $R^{2a1}$, $R^{2a2}$ and $R^{2a3}$ independently each represent a C1 to C8 alkyl group, a C3 to C20 alicyclic hydrocarbon group or a group composed of the alkyl group and the alicyclic hydrocarbon group,
or $R^{2a1}$ and $R^{2a2}$ can be bonded each other to form a C3 to C20 divalent alicyclic hydrocarbon group together with the carbon atom bonded to $R^{2a1}$ and $R^{2a2}$, and * represents a binding site; or formula (R2-2)

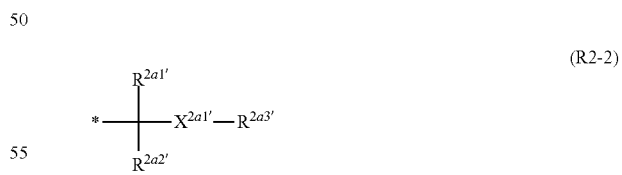

wherein $R^{2a1'}$ and $R^{2a2'}$ independently each represent a hydrogen atom or a C1 to C12 hydrocarbon group, and $R^{2a3'}$ represents a C1 to C20 hydrocarbon group, or $R^{2a2'}$ and $R^{2a3'}$ can be bonded each other to form a C2 to C20 divalent heterocyclic group together with $X^{2a1'}$ and the carbon atom bonded to $R^{2a2'}$ and $R^{2a3'}$, and a methylene group in the hydrocarbon group and the heterocyclic group can be replaced by —O— or —S—,
$X^{2a1'}$ represents an oxygen atom or a sulfur atom, and
* represents a binding site.

[4] An acid generator which contains the salt according to any one of [1] to [3].

[5] A photoresist composition which contains the salt represented by the formula (I) and a resin having an acid-labile group.

[6] The photoresist composition according to [5], which further contains a salt which generates an acid weaker in acidity than an acid generated from the salt represented by the formula (I).

[7] A process for producing a photoresist pattern comprising the following steps (1) to (5)
(1) a step of applying the photoresist composition according [5] or [6] on a substrate,
(2) a step of forming a composition film by conducting drying,
(3) a step of exposing the composition film to radiation,
(4) a step of baking the exposed composition film, and
(5) a step of developing the baked composition film.

DESCRIPTION OF PREFERRED EMBODIMENTS

Herein, the term "(meth)acrylic monomer" means a monomer having a structure of "CH$_2$=CH—CO—" or "CH$_2$=C(CH$_3$)—CO—", as well as "(meth)acrylate" and "(meth)acrylic acid" mean "an acrylate or methacrylate" and "an acrylic acid or methacrylic acid" respectively. Herein, chain structure groups include those having a linear structure and those having a branched structure. Unless otherwise specified, the term "aliphatic hydrocarbon group" means a chain aliphatic hydrocarbon group.

The indefinite articles "a" and "an" are taken as the same meaning as "one or more".

The term "solid components" means components other than solvents in a resist composition.

The salt represented by formula (I) is sometimes referred to as "Salt (I)", the cation contained in formula (I) is sometimes referred to as "Cation (I)", and the anion contained in formula (I) is sometimes referred to as "Anion (I)".
<Salt (I)>
Salt (I) is represented by formula (I).

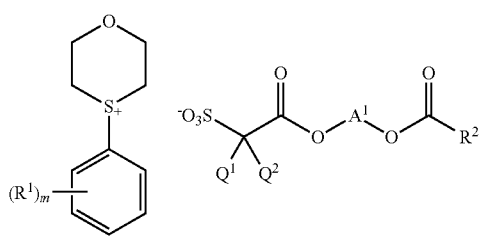
(I)

In formula (I), $R^1$ each independently represents a C1 to C12 alkyl group in which a methylene group can be replaced by an oxygen atom or a carbonyl group;
$Q^1$ and $Q^2$ each independently represent a fluorine atom or a C1 to C6 perfluoroalkyl group;
$A^1$ represents a lactone ring-containing group which has 4 to 24 carbon atoms;
$R^2$ represents an acid-labile group; and
"m" represents an integer of 0 to 3.

Examples of the alkyl group represented by $R^{1'}$ include a methyl group, an ethyl group, n-propyl group, an isopropyl group, a n-butyl group, a sec-butyl group, a tert-butyl group, a pentyl group, a hexyl group, a heptyl group, a 2-ethylhexyl group, an octyl group, a nonyl group, an undecyl group and a decyl group.

$R^1$ is preferably a C1 to C6 alkyl group, more preferably a C1 to C4 alkyl group such as a methyl group, an ethyl group, n-propyl group, an isopropyl group, and tert-butyl group, and still more preferably a methyl group and tert-butyl group.

For $R^1$, examples of the group in which a methylene group of the alkyl group has been replaced by an oxygen atom or a carbonyl group include a methoxy group, an ethoxy group, a butoxy group, a hexyloxy group, methoxyethyl group, an ethoxyethyl group, an ethoxyethoxy groups, ethoxyethoxyethoxy group, an ethoxyethoxyethoxyethoxy group, an ethoxyethoxyethoxyethoxyethoxy group, an acetyl group, a methoxycarbonyl group, an acetyloxy group, and a butoxycarbonyloxy group.

"m" represents an integer of 0 to 3, preferably an integer of 1 or 2, and still more preferably 1.

Examples of the perfluoroalkyl group for $Q^1$ and $Q^2$ include trifluoromethyl, perfluoroethyl, perfluoropropyl, perfluoroisopropyl, perfluorobutyl, perfluoro-sec-butyl, perfluoro (tert-butyl), perfluoropentyl and perfluorohexyl groups. $Q^1$ and $Q^2$ each independently are preferably a trifluoromethyl group or a fluorine atom, and both of $Q^1$ and $Q^2$ are more preferably a fluorine atom.

For $A^1$, the lactone ring may be any of monocyclic one and polycyclic one. Specific examples of the lactone ring include the following ones.

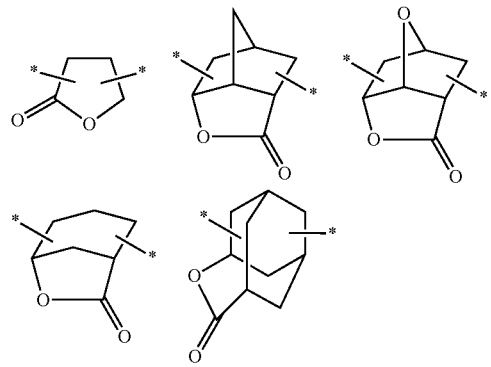

In each formula, * represents a binding site.

The lactone ring has preferably 5 to 12 carbon atoms, more preferably 5 to 9 carbon atoms. $A^1$ represents preferably a group which has a norbornanelactone ring.

The group represented by $A^1$, i.e. the lactone ring-containing group which has 4 to 24 carbon atoms, includes a C4 to C24 divalent group composed of a divalent hydrocarbon group and a lactone ring, and a C4 to C24 divalent group consisting of a lactone ring. Examples of the divalent hydrocarbon group include a divalent aliphatic hydrocarbon group such as an alkanediyl group.

In the divalent hydrocarbon group present in $A^1$, a methylene group can be replaced by a carbonyl group or an oxygen atom. When a methylene group has been replaced by a carbonyl group or an oxygen atom therein, the carbon atom presented in the replaced methylene group is taken as carbon atoms of divalent group.

Examples of the group represented by $A^1$ include a group represented by —(C1 to C6 divalent aliphatic hydrocarbon group)-(a lactone group)-(C1 to C6 divalent aliphatic hydrocarbon group).

The divalent aliphatic hydrocarbon group presented in $A^1$ is preferably a C1 to C6 alkanediyl group in which one or two methylene groups have been replaced by a carbonyl group or an oxygen atom, more preferably —$(CH_2)_{xa1}$—CO—O— where xa1 represents an integer of 0 to 4, preferably 0 or 1.

Specific examples of the group represented by $A^1$ include the following ones.

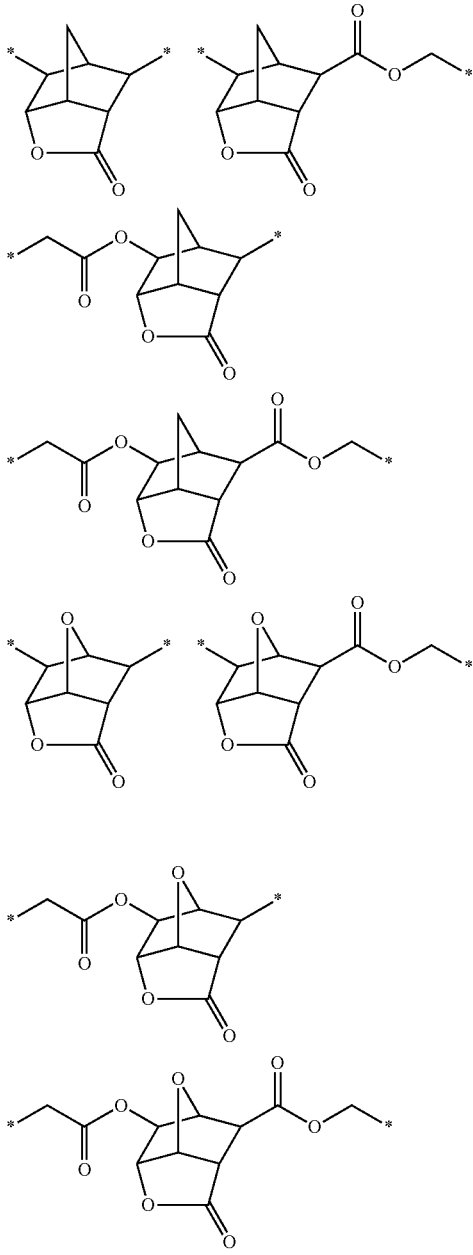

In each formula, * represents a binding site.

$R^2$ is an acid-labile group. In formula (I), "an acid-labile group" means a functional group having a leaving group which is removed therefrom by the action of an acid to thereby form a carboxy group.

$R^2$ is preferably represented by formula (R2-1):

wherein $R^{2a1}$, $R^{2a2}$ and $R^{2a3}$ independently each represent a C1 to C8 alkyl group, a C3 to C20 alicyclic hydrocarbon group or a group composed of the alkyl group and the alicyclic hydrocarbon group, or $R^{2a1}$ and $R^{2a2}$ can be bonded each other to form a C3 to C20 divalent alicyclic hydrocarbon group together with the carbon atom bonded to $R^{2a1}$ and $R^{2a2}$, and
and * represents a binding site; or
formula (R2-2):

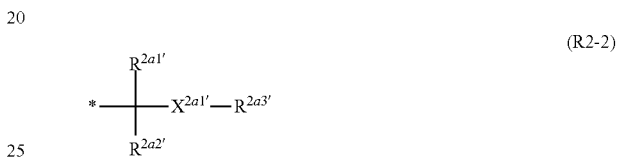

wherein $R^{2a1'}$ and $R^{2a2'}$ independently each represent a hydrogen atom or a C1 to C12 hydrocarbon group, and $R^{2a3'}$ represents a C1 to C20 hydrocarbon group, or $R^{2a2'}$ and $R^{2a3'}$ can be bonded each other to form a C3 to C20 divalent heterocyclic group together with $X^{2a1'}$ and the carbon atom bonded to $R^{2a2}$ and $R^{2a3'}$, and a methylene group in the hydrocarbon group and the heterocyclic group can be replaced by —O— or —S—,
$X^{2a1'}$ represents an oxygen atom or a sulfur atom, and
* represents a binding site.

For $R^{2a1}$, $R^{2a2}$ and $R^{2a3}$, specific examples of the alkyl group include a methyl group, an ethyl group, a propyl group, an isopropyl group, a butyl group, a pentyl group, a hexyl group, a heptyl group and an octyl group.

The alicyclic hydrocarbon group may be monocyclic or polycyclic. Examples of the alicyclic hydrocarbon group include a monocyclic alicyclic hydrocarbon group such as a C3-C20 cycloalkyl group (e.g. a cyclopentyl group, a cyclohexyl group, a cycloheptyl group and a cyclooctyl group) and a polycyclic alicyclic hydrocarbon group such as a decahydronaphthyl group, an adamantyl group, a norbornyl group, and the followings:

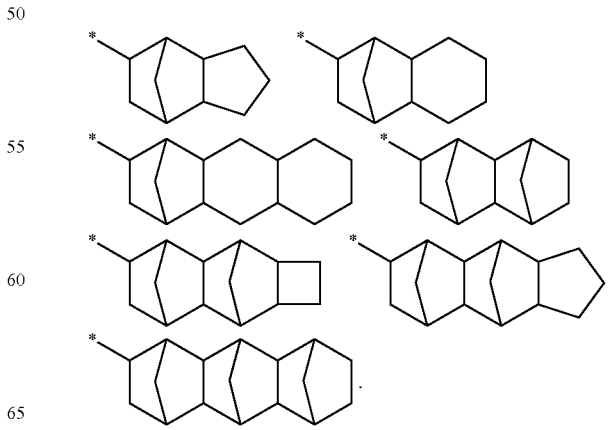

The alicyclic hydrocarbon group preferably has 3 to 16 carbon atoms. Examples of the group consisting of alkyl and alicyclic hydrocarbon group include a methylcyclohexyl group, a dimethylcyclohexyl group, a methylnorbornyl group, an adamantylmethyl group, and a norbornylethyl group.

The "na" is preferably 0.

When the divalent alicyclic hydrocarbon group is formed by bonding $R^{2a1}$ and $R^{2a2}$ each other, examples of the moiety —C($R^{2a1}$)($R^{2a2}$)($R^{2a3}$) include the following groups and the divalent hydrocarbon group preferably has 3 to 12 carbon atoms.

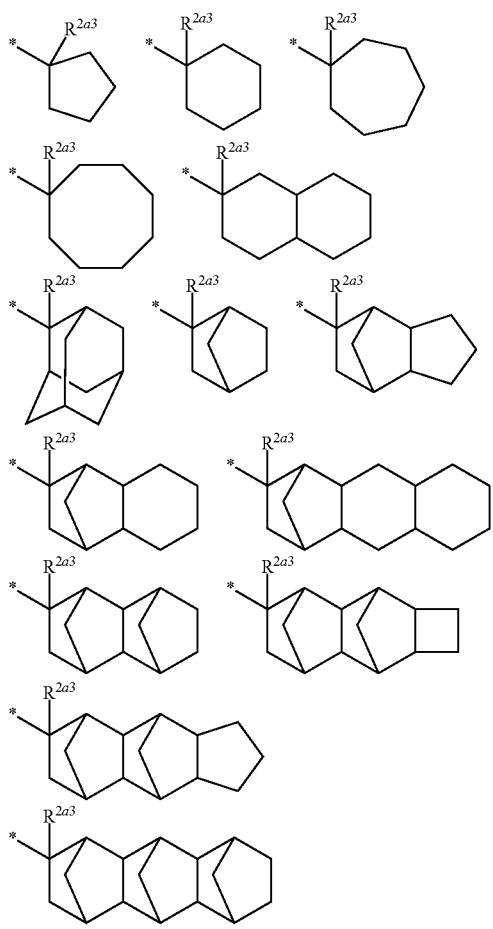

In each formula, $R^{2a3}$ is the same as defined above.

Preferred are 1,1'-dialkylalkoxycarbonyl group, i.e., the group represented by the formula (R2-1) wherein $R^{2a1}$, $R^{2a2}$ and $R^{2a3}$ independently each represent a C1-C8 alkyl group such as a tert-butyl group;

2-alkyladamantane-2-yloxylcarbonyl group, i.e., the group represented by the formula (R2-1) wherein $R^{2a1}$ and $R^{2a2}$ are bonded each other to form an adamantyl ring and $R^{2a3}$ is a C1 to C8 alkyl group such as a 2-alkyl-2-adamantyl group; and 1-(adamantane-1-yl)-1-alkylalkoxycarbonyl group, i.e., the group represented by the formula (R2-1) wherein $R^{2a1}$ and $R^{2a2}$ are C1 to C8 alkyl groups and $R^{2a3}$ is an adamantyl group.

For formula (R2-2), examples of the hydrocarbon group include an alkyl group, an alicyclic hydrocarbon group, an aromatic hydrocarbon group and a group consisting of two or more of them.

Examples of the alkyl group and the alicyclic hydrocarbon group include the same as described above. Examples of the aromatic hydrocarbon group include an aryl group such as a phenyl group, a naphthyl group, a p-methylphenyl group, a p-tert-butylphenyl group, a p-adamantylphenyl group, a tolyl group, a xylyl group, a cumyl group, a mesityl group, a biphenyl group, an anthryl group, a phenanthryl group, a 2,6-diethylphenyl group and a 2-methyl-6-ethylphenyl group.

When the divalent hydrocarbon group is formed by bonding $R^{2a2'}$ and $R^{2a3'}$ each other, examples of the moiety —C($R^{2a1'}$)($R^{2a2'}$)($R^{2a3'}$) include the following groups.

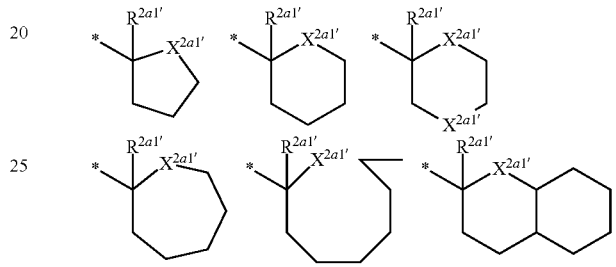

In each formula, $R^{2a1'}$ and $X^{2a1'}$ are as defined above.

It is preferred that at least one of $R^{2a1'}$ and $R^{2a2'}$ is a hydrogen atom.

Examples of the group represented by the formula (R2-2) include the following.

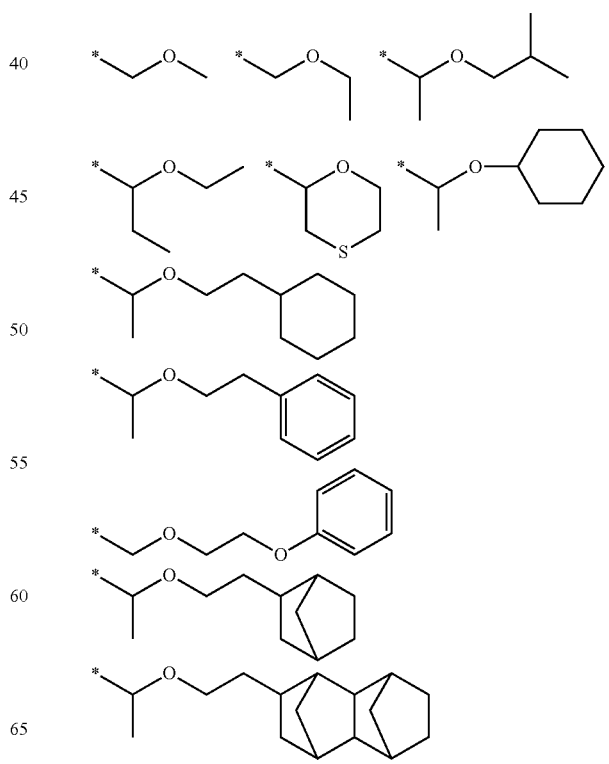

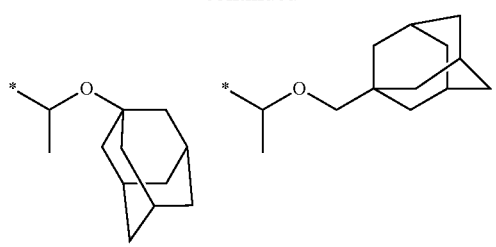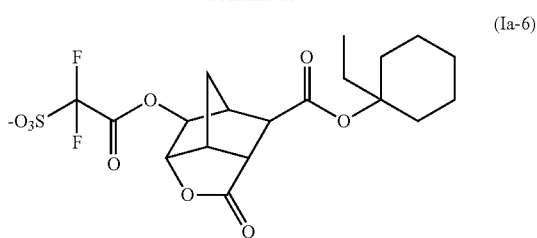
R² is preferably one represented by formula (R2-1), more preferably one represented by formula (R2-1) which has an adamantane ring. Examples of the anion (I) include those represented by the following formulae, preferably those represented by the formulae (Ia-1) to (Ia-6), and more preferably those represented by the formulae (Ia-1) to (Ia-4).
(Ia-1)
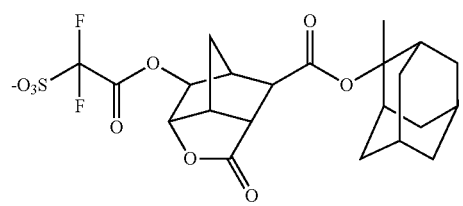
(Ia-2)
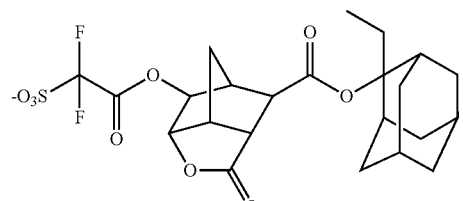
(Ia-3)
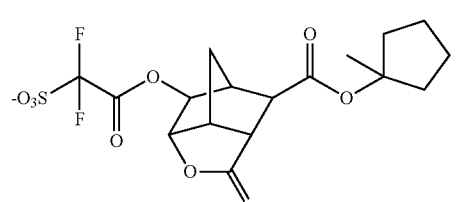
(Ia-4)
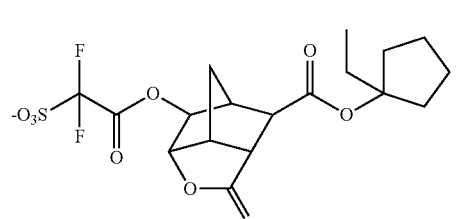
(Ia-5)
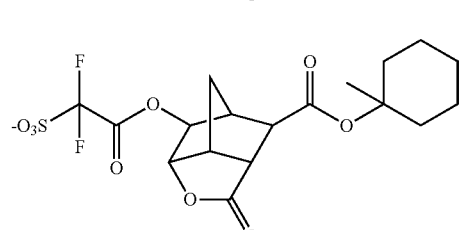
(Ia-6)
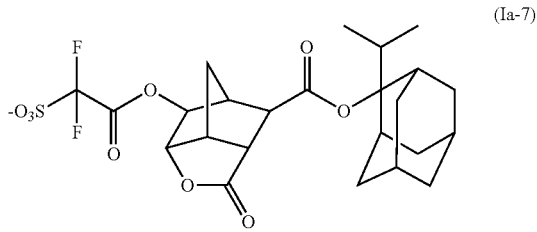
(Ia-7)
(Ia-8)
(Ia-9)
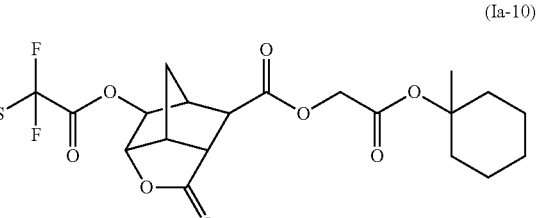
(Ia-10)
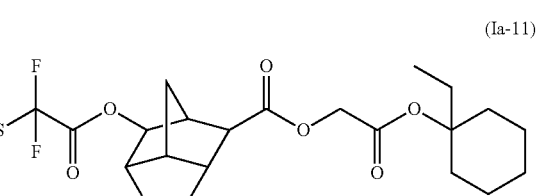
(Ia-11)
(Ia-12)
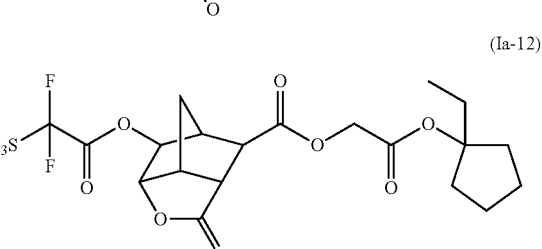

(Ia-13)
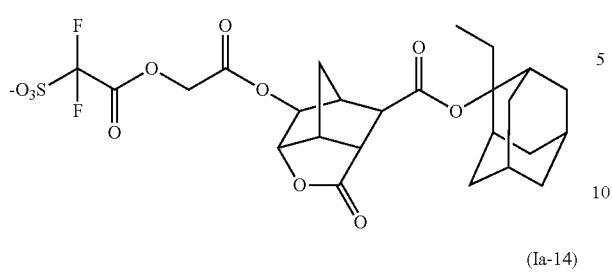
(Ia-14)
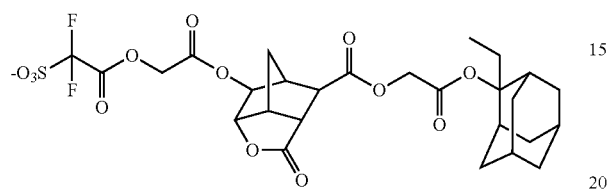
Examples of Cation (I) include the following ones, preferably those represented by the formulae (c-1) to (c-3) and (c-5)
(c-1)
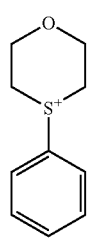
(c-2)
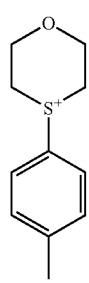
(c-3)
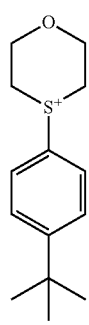
(c-4)
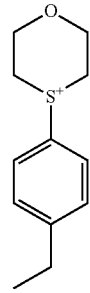
(c-5)
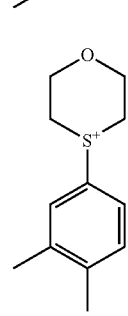
(c-6)
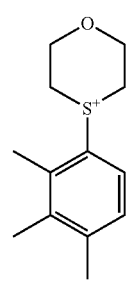
(c-7)
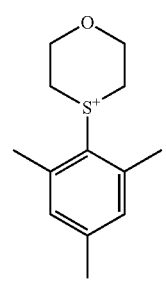
(c-8)
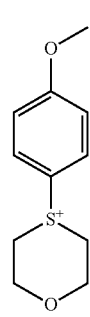

(c-9)
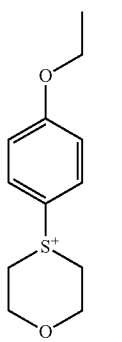
(c-10)
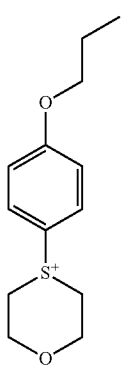
(c-11)
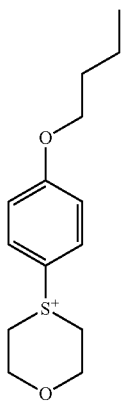
(c-12)
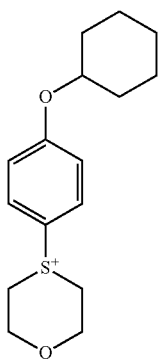
(c-13)
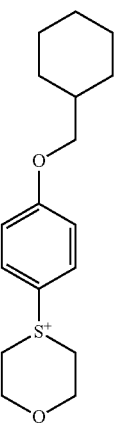
(c-14)
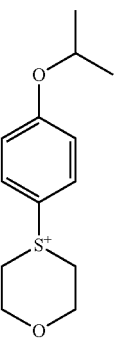
(c-15)
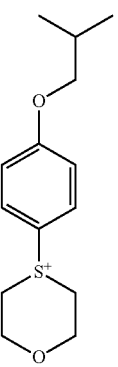
(c-16)
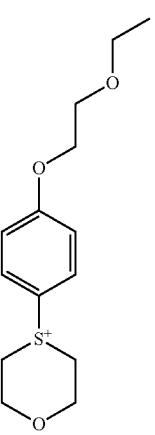

(c-17)
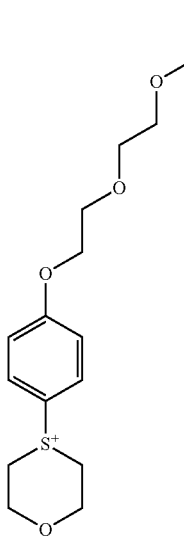
(c-18)
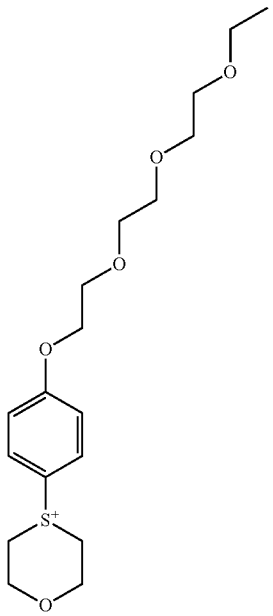
(c-19)
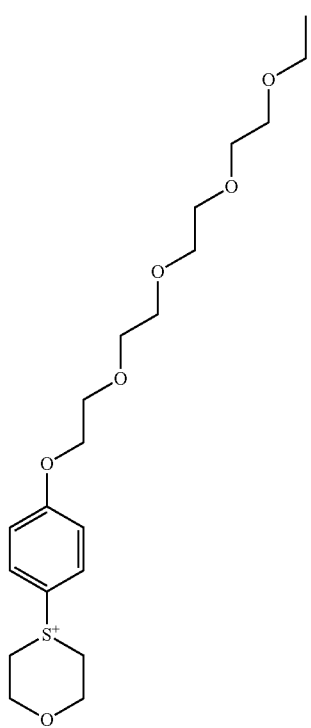
Specific examples of the Salt (I) include those consisting of an anion represented by one of formulae (Ia-1) to (Ia-14) and a cation represented by one of formulae (c-1) to (c-19), preferably those represented by the following formulae.
(I-1)
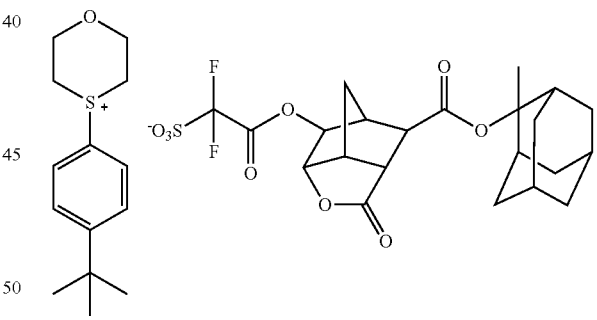
(I-2)
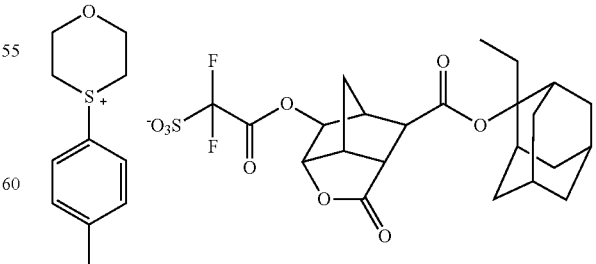

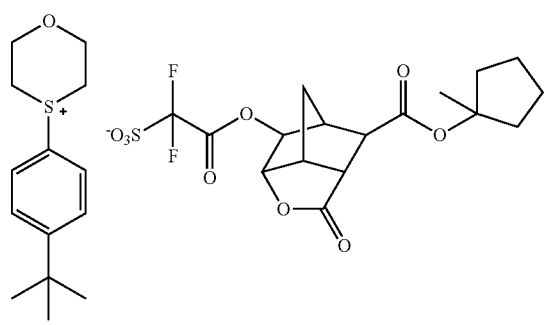
(I-3)
(I-4)
(I-5)
(I-6)
(I-7)
(I-8)
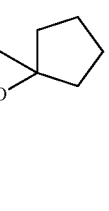
(I-9)
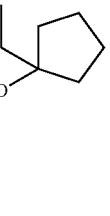
(I-10)
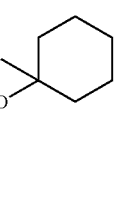
(I-11)
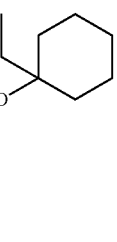
(I-12)

(I-13)
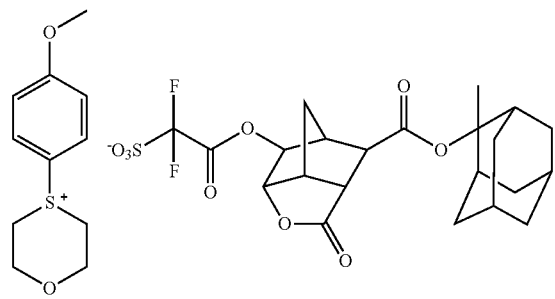
(I-18)
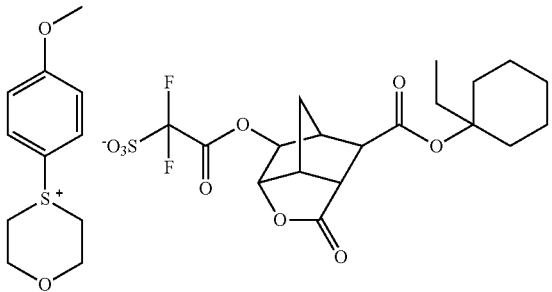
(I-14)
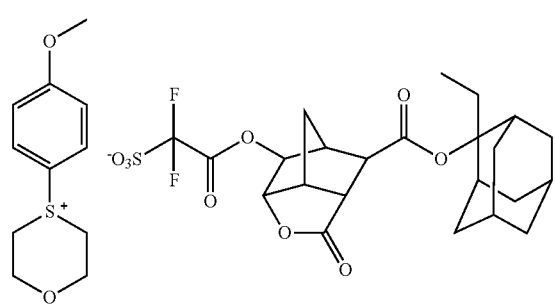
(I-19)
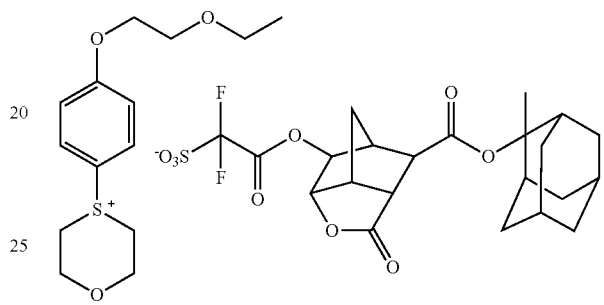
(I-15)
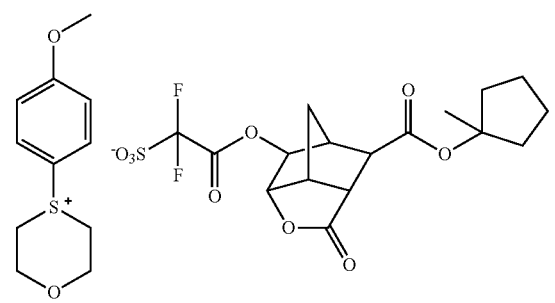
(I-20)
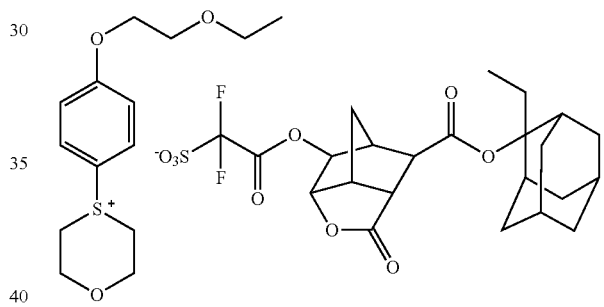
(I-16)
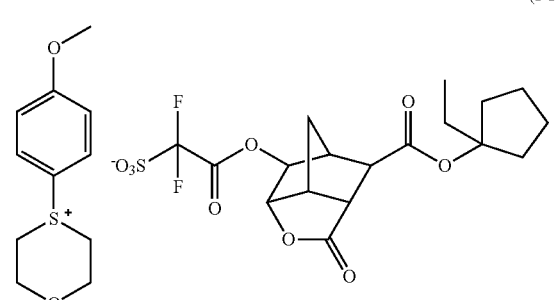
(I-21)
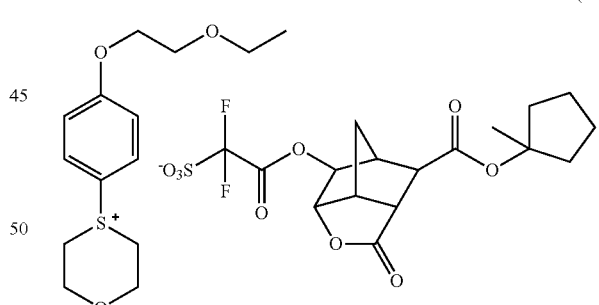
(I-17)
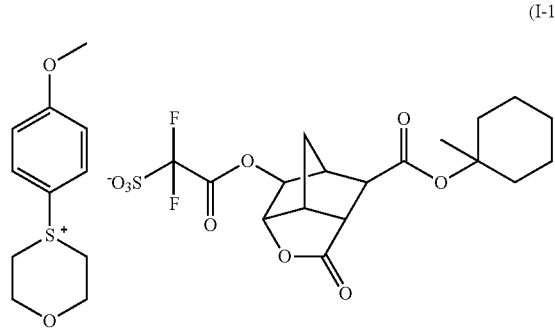
(I-22)
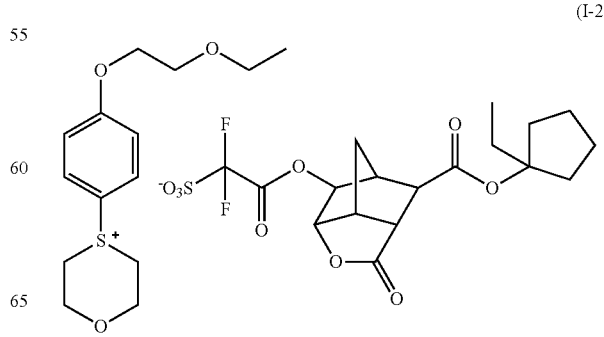

(I-23)

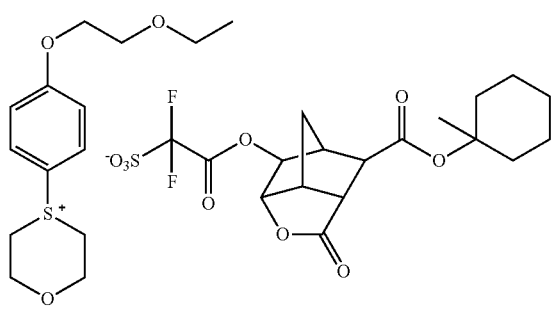

(I-24)

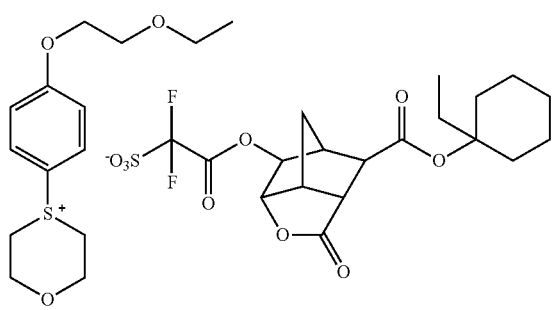

Among them, the salts represented by formulae (I-1), (I-2), (I-7) (I-8), (I-13), (I-14), (I-17) and (I-18) are preferred, and the salts represented by formulae (I-1), (I-2), (I-7) (I-8), (I-13) and (I-14) are more preferred.

Salt (I) can be produced by reacting a compound represented by formula (I-a) with a compound represented by formula (I-b) in the presence of a catalyst, in a solvent such as acetonitrile, chloroform or water:

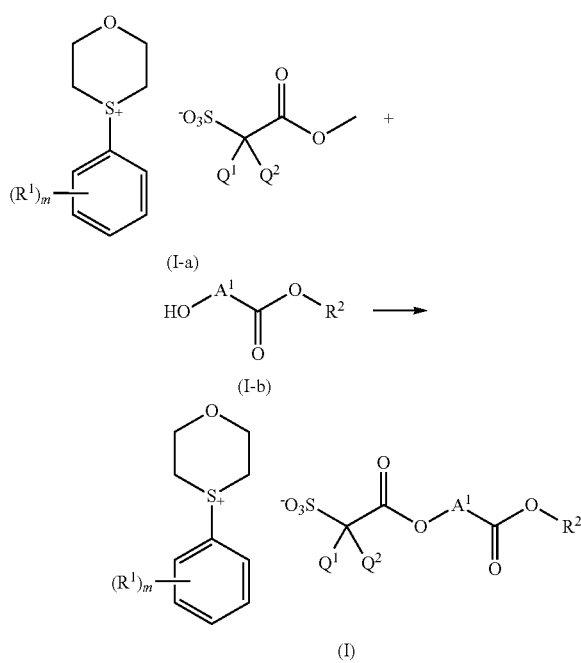

wherein $R^1$, $R^2$, $Q^1$, $Q^2$, $A^1$ and m are as defined above.

Examples of the catalyst include the following one.

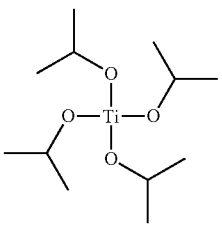

The reaction can be conducted at temperature of preferably −5° C. to 40° C., for 0.5 to 24 hours.

Examples of the compound represented by formula (I-b) include the following ones which are available on the market.

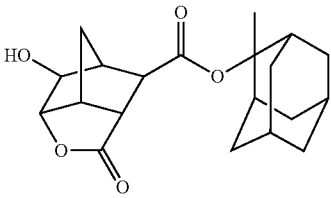

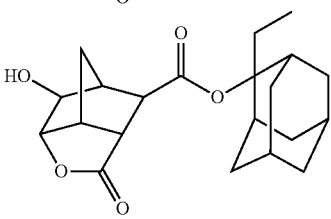

The compound represented by formula (I-a) can be produced by reacting a compound represented by formula (I-c) with a compound represented by formula (I-d) in a solvent such as chloroform:

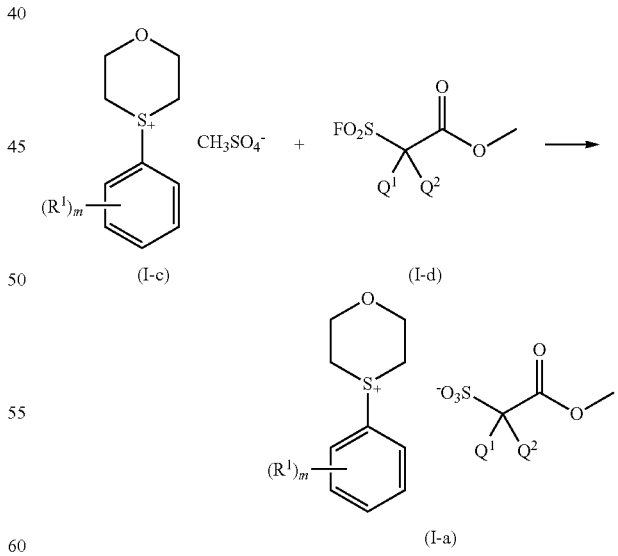

wherein $R^1$, $Q^1$, $Q^2$ and m are as defined above.

The reaction can be conducted at temperature of preferably 15° C. to 120° C., for 0.5 to 12 hours.

Examples of the compound represented by formula (I-d) include the following compound which is available on the market.

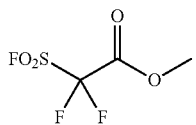

The compound represented by formula (I-c) can be produced by reacting a compound represented by formula (I-e) with a compound represented by formula (I-f) in the presence of a catalyst such as copper (II) acetate in a solvent such as chloroform:

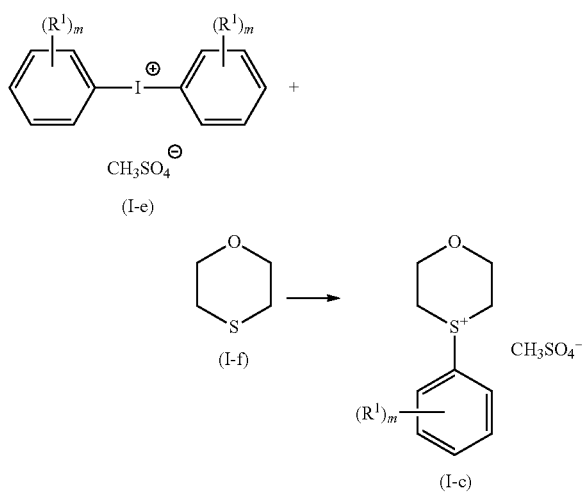

wherein R¹ and m are as defined above.

The reaction can be conducted at temperature of preferably 15° C. to 80° C., for 0.5 to 24 hours.

Examples of the compound represented by formula (I-e) include the following ones which are available on the market.

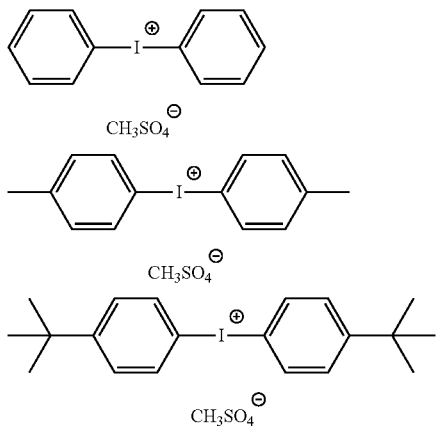

The compound represented by formula (I-e) can be produced by reacting a compound represented by formula (I-g) with a compound represented by formula (I-h) in a solvent such as chloroform:

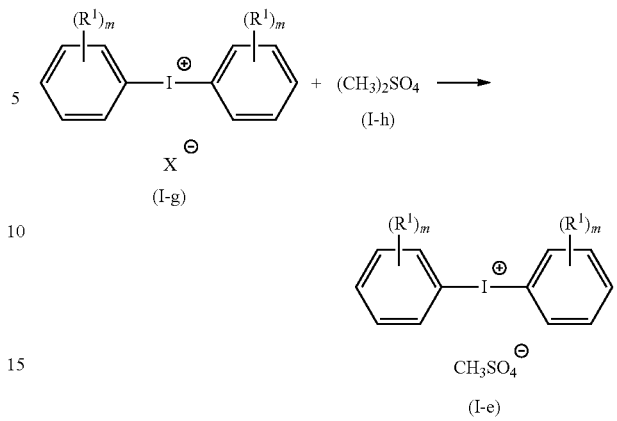

wherein R¹ and m are as defined above, and X represents a chlorine atom, a bromine atom or an iodine atom.

The reaction can be conducted at temperature of preferably 15° C. to 80° C., for 0.5 to 24 hours.

Examples of the compound represented by formula (I-g) include the following ones which are available on the market.

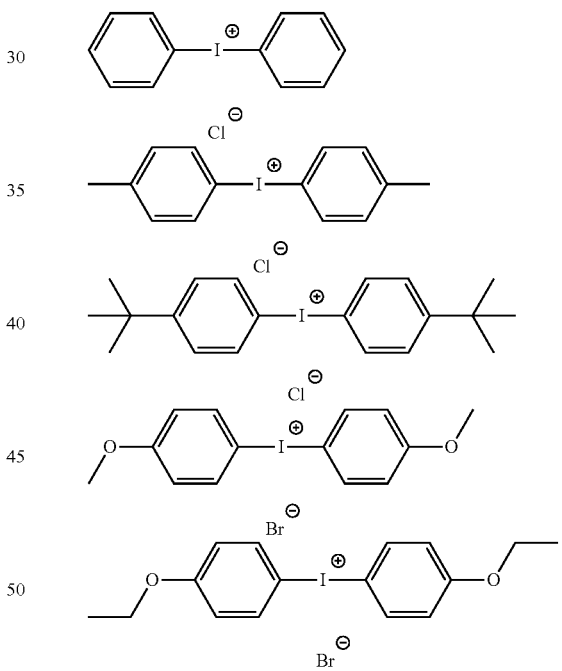

<Acid Generator>

The acid generator of the disclosure contains a Salt (I). The acid generator of the disclosure may contain two or more kinds of Salts (I).

Here, the acid generator means salts capable of generating an acid with a developer described later.

The acid generator may further contain a known acid generator in the art of the photoresist compositions. The known acid generators are sometimes referred to as "acid generator (B)". In the acid generator of the disclosure, the acid generator (B) may consist of a single salt or contain two or more of salts.

The acid generator (B) may be any of an ionic acid generator and a non-ionic acid generator, and preferably an ionic acid generator.

Examples of the acid generator include a salt such as an organic sulfonium salt, an organic sulfonic acid salt, and acid generators as mentioned in JP2013-68914A1, JP2013-3155A1 and JP2013-11905A1. Specific examples of the acid generator include the following salts represented by the formulae (B1-1) to (B1-30). Among them, those which contain an arylsulfonium cation are preferred, the salts represented by the formulae (B1-1), (B1-2), (B1-3), (B1-6), (B1-7), (B1-11), (B1-12), (B1-13), (B1-14), (B1-20), (B1-21), (B1-22), (B1-23), (B1-24), (31-25), (B1-26) and (B1-29) are more preferred.

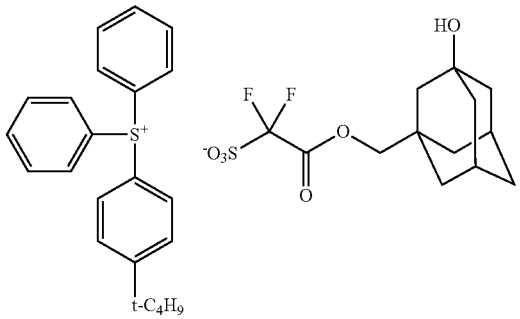

(B1-4)

(B1-5)

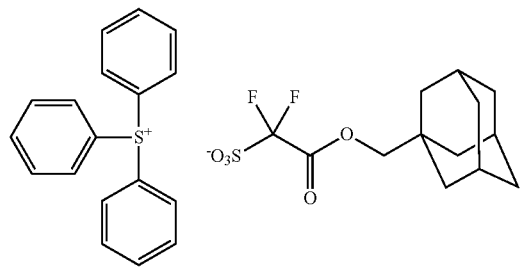

(B1-1)

(B1-2)

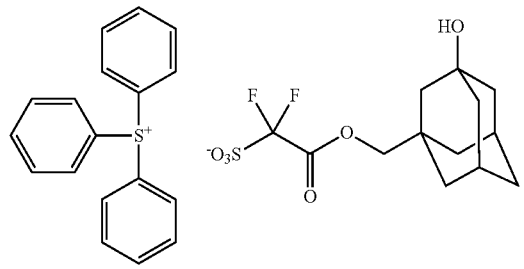

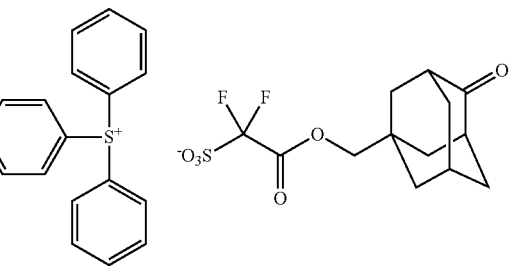

(B1-6)

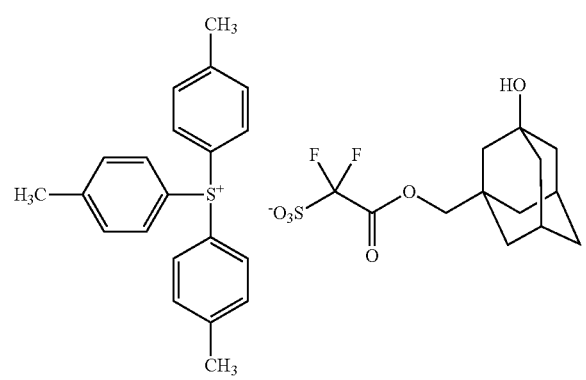

(B1-3)

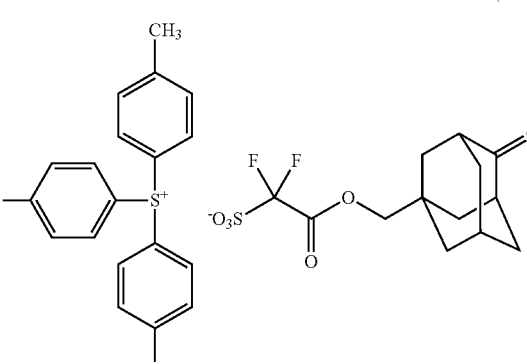

(B1-7)

(B1-8)
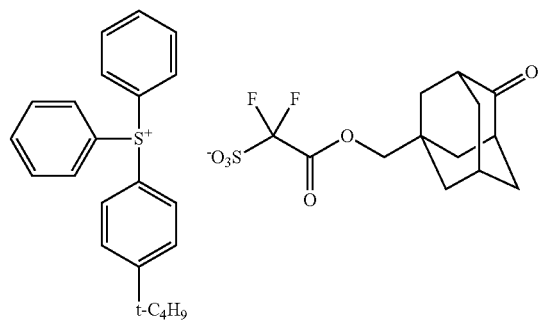
(B1-9)
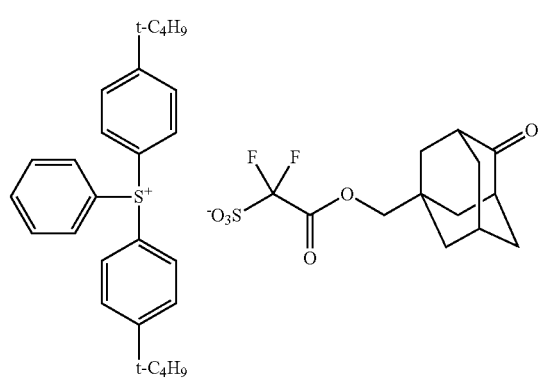
(B1-10)
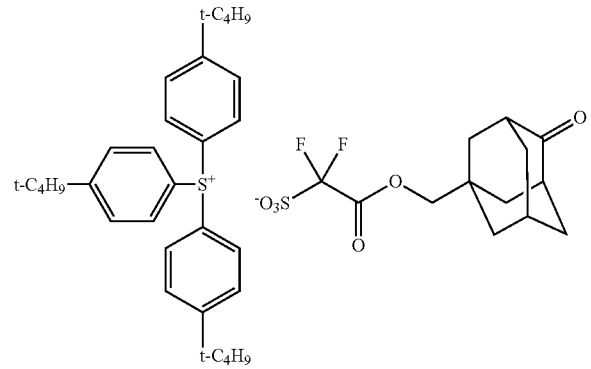
(B1-11)
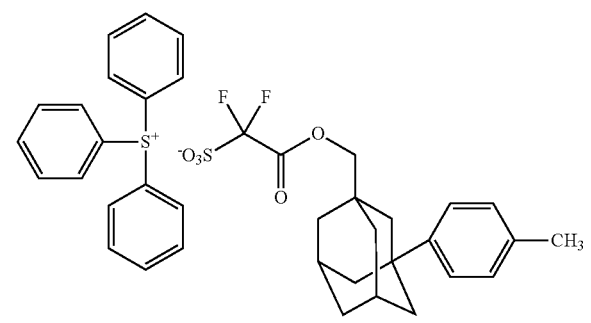
(B1-12)
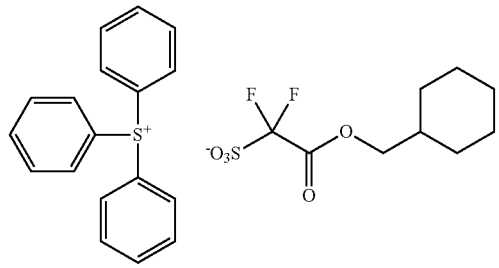
(B1-13)
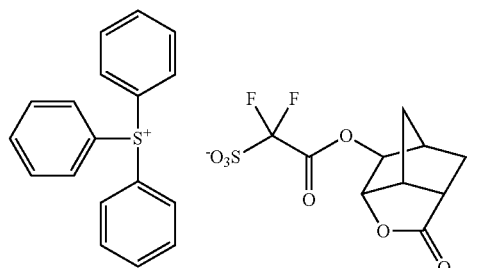
(B1-14)
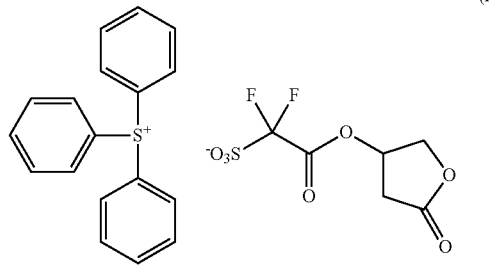
(B1-15)
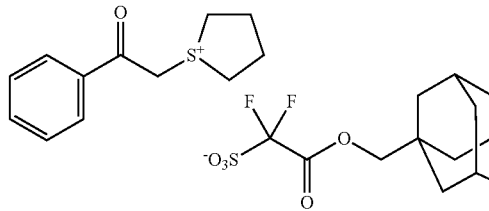
(B1-16)
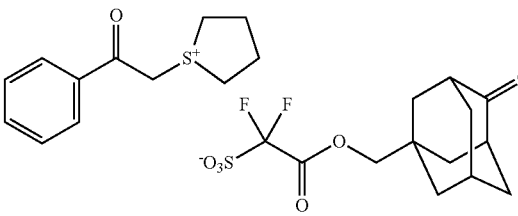
(B1-17)
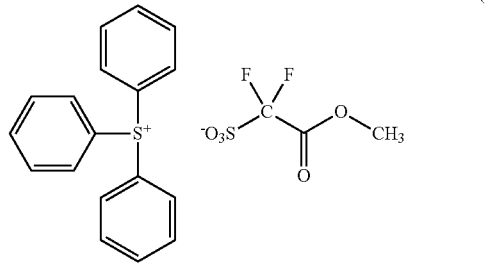

(B1-18) 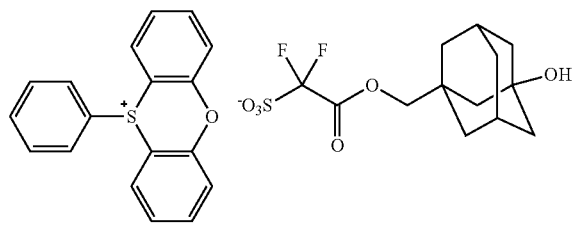
(B1-19) 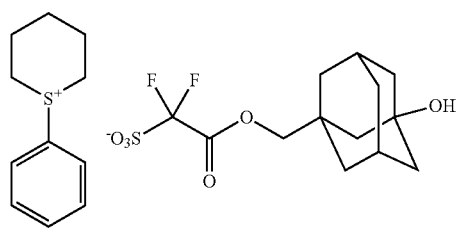
(B1-20) 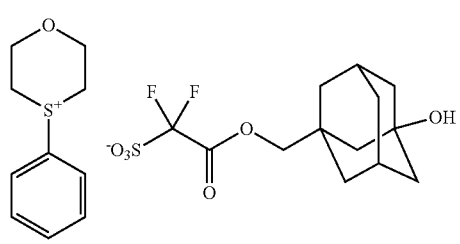
(B1-21) 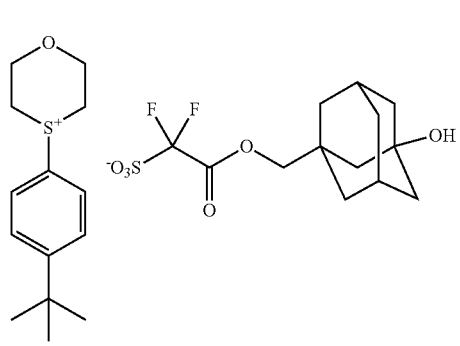
(B1-22) 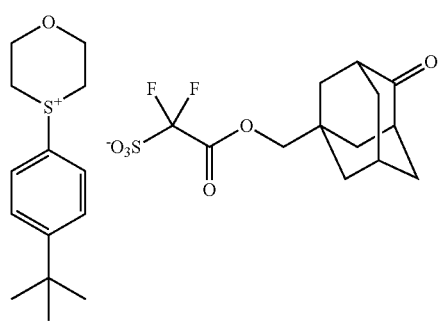
(B1-23) 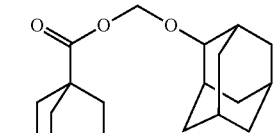
(B1-24) 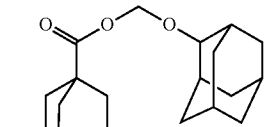
(B1-25) 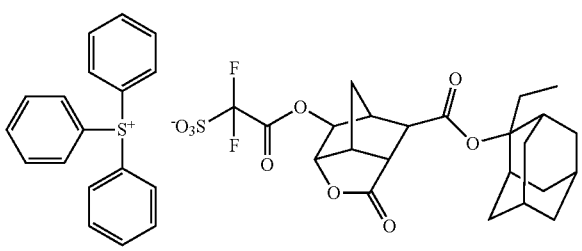
(B1-26) 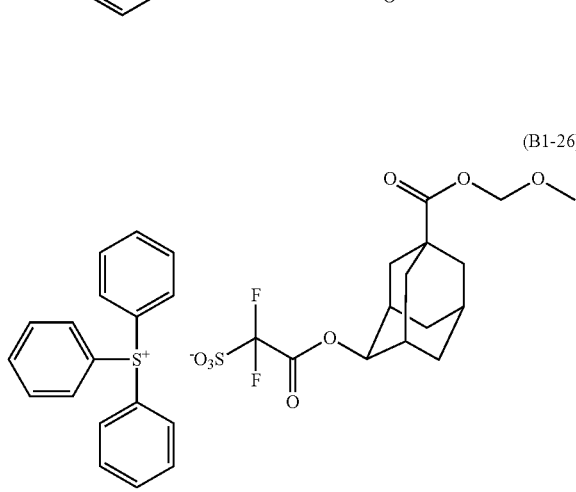

-continued (B1-27)
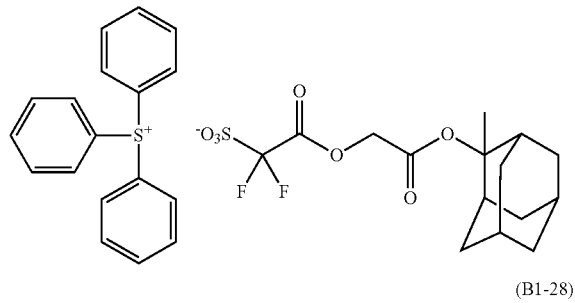

(B1-28)
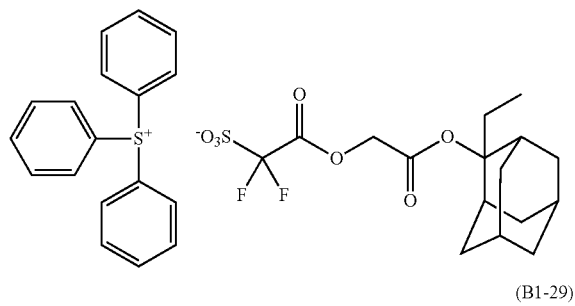

(B1-29)

(B1-30)
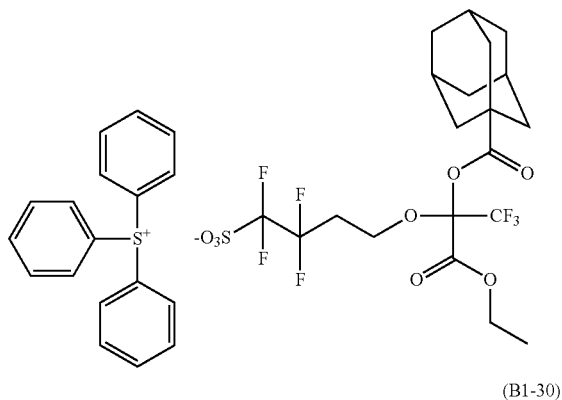

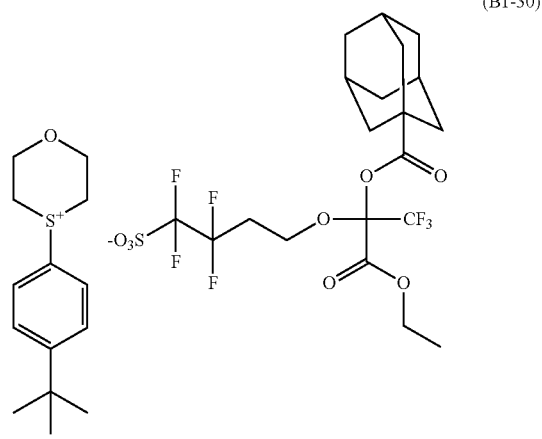

When the acid generator further contains an acid generator (B), the amount ratio of the Salt (I) and the acid generator (B) [the Salt (I): the acid generator (B), weight ratio] is usually 1:99 to 99:1, preferably 2:98 to 98:2, more preferably 5:95 to 95:5, still more preferably 90:10 to 60:40, and further still more preferably 85:15 to 70:30.

<Photoresist Composition>

The photoresist composition of the disclosure contains a Salt (I) and a resin having an acid-labile group which resin is sometimes referred to as "Resin (A)".

The photoresist composition may further contain an acid generator (B), a quencher, or a solvent.

The photoresist composition preferably further contains a quencher, or a solvent, more preferably both of them.

In the photoresist composition, the content of Salt (I) is usually 1 part by mass or more, preferably 2 parts by mass or more, per 100 parts by mass of the resin (A). The content of the Salt (I) is usually 50 parts by mass or less, preferably 45 parts by mass or less, per 100 parts by mass of the resin (A).

In the photoresist composition, the content of the acid generator (B) is usually 1 part by mass or more, preferably 3 parts by mass or more, per 100 parts by mass of the resin (A). The content of it is usually 40 parts by mass or less, preferably 35 parts by mass or less, per 100 parts by mass of the resin (A).

In the photoresist composition of the disclosure, the acid generator (B) may consist of a single salt or contain two or more of salts.

In the photo resist composition of the disclosure, when the photo resist composition contains the salt (I) and the acid generator (B), the total amount of the salt (I) and the acid generator (B) is preferably 1.5 parts by mass or more and more preferably 3 parts by mass or more, and preferably 50 parts by mass or less and more preferably 45 parts by mass or less with respect to 100 parts by mass of the resin (A).

<Resin (A)>

Resin (A) usually has a structural unit having an acid-labile group.

Hereinafter, the structural unit is sometimes referred to as "structural unit (a1)".

Preferably Resin (A) further has another structural unit than the structural unit (a1), i.e. a structural unit having no acid-labile group, which is sometimes referred to as "structural unit (s)". Herein, the structural units (a1) and (s) include no structural unit (II) described later, which generally have neither a cation nor an anion.

In Resin (A), "an acid-labile group" means a functional group having a leaving group which is removed therefrom by the action of an acid to thereby form a hydrophilic group, such as a hydroxyl group or a carboxy group.

Examples of the acid-labile group include
a group represented by the formula (1):

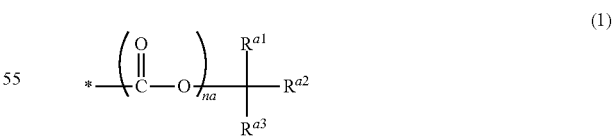

(1)

wherein $R^{a1}$, $R^{a2}$ and $R^{a3}$ independently each represent a C1 to C8 alkyl group, a C3 to C20 alicyclic hydrocarbon group or a group composed of the alkyl group and the alicyclic hydrocarbon group, and $R^{a1}$ and $R^{a2}$ can be bonded each other to form a C2 to C20 divalent alicyclic hydrocarbon group, "na" represents an integer of 0 or 1, and * represents a binding site; and a group represented by the formula (2):

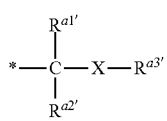
(2)

wherein $R^{a1'}$ and $R^{a2'}$ independently each represent a hydrogen atom or a C1 to C12 hydrocarbon group, and $R^{a3'}$ represents a C1 to C20 hydrocarbon group, and $R^{a2'}$ and $R^{a3'}$ can be bonded each other to form a C3 to C20 divalent heterocyclic group, and one or more —$CH_2$— in the hydrocarbon group and the divalent heterocyclic group can be replaced by —O— or —S—, X represents an oxygen atom or a sulfur atom, and * represents a binding site.

For $R^{a1}$, $R^2$, and $R^{a3}$, specific examples of the alkyl group include a methyl group, an ethyl group, a propyl group, an isopropyl group, a butyl group, a pentyl group, a hexyl group, a heptyl group and an octyl group.

The alicyclic hydrocarbon group may be monocyclic or polycyclic.

Examples of the alicyclic hydrocarbon group include a monocyclic alicyclic hydrocarbon group such as a C3 to C20 cycloalkyl group (e.g. a cyclopentyl group, a cyclohexyl group, a cycloheptyl group and a cyclooctyl group) and a polycyclic alicyclic hydrocarbon group such as a decahydronaphthyl group, an adamantyl group, a norbornyl group, and the followings:

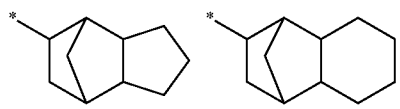

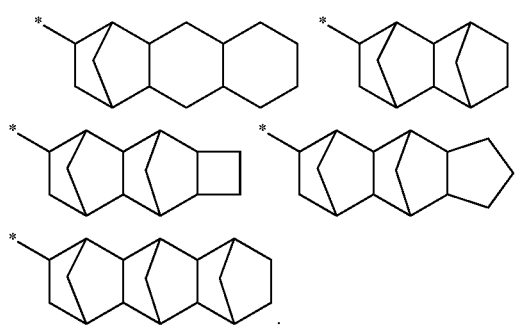

The alicyclic hydrocarbon group preferably has 3 to 16 carbon atoms.

Examples of the group consisting of alkyl and alicyclic hydrocarbon group include a methylcyclohexyl group, a dimethylcyclohexyl group, a methylnorbornyl group, an adamantylmethyl group, and a norbornylethyl group.

The "na" is preferably 0.

When the divalent alicyclic hydrocarbon group is formed by bonding $R^{a1}$ and $R^{a2}$ each other, examples of the moiety —$C(R^{a1})(R^{a2})(R^{a3})$— include the following groups and the divalent hydrocarbon group preferably has 3 to 12 carbon atoms.

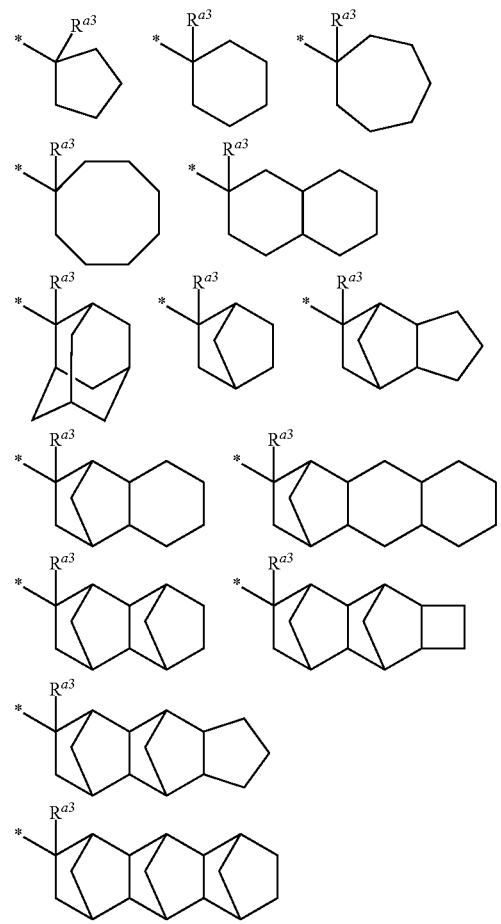

In each formula, $R^{a3}$ is the same as defined above.
Preferred are 1,1'-dialkylalkoxycarbonyl group, i.e., the group represented by the formula (1) wherein $R^{a1}$, $R^{a2}$ and $R^{a3}$ independently each represent a C1-C8 alkyl group such as a tert-butyl group;

2-alkyladamantane-2-yloxylcarbonyl group, i.e., the group represented by the formula (1) wherein $R^{a1}$ and $R^{a2}$ are bonded each other to form an adamantyl ring and $R^{a3}$ is a C1 to C8 alkyl group such as a 2-alkyl-2-adamantyl group; and 1-(adamantane-1-yl)-1-alkylalkoxycarbonyl group, i.e., the group represented by the formula (1) wherein $R^{a1}$ and $R^{a2}$ are C1 to C8 alkyl groups and $R^{a3}$ is an adamantyl group.

For formula (2), examples of the hydrocarbon group include an alkyl group, an alicyclic hydrocarbon group, an aromatic hydrocarbon group and a group consisting of two or more of them.

Examples of the alkyl group and the alicyclic hydrocarbon group include the same as described above. Examples of the aromatic hydrocarbon group include an aryl group such as a phenyl group, a naphthylgroup, a p-methylphenyl group, a p-tert-butylphenyl group, a p-adamantylphenyl group, a tolyl group, a xylyl group, a cumyl group, a mesityl group, a biphenyl group, an anthryl group, a phenanthryl group, a 2,6-diethylphenyl group and a 2-methyl-6-ethylphenyl group.

When the divalent hydrocarbon group is formed by bonding $R^{a2'}$ and $R^{a3'}$ each other, examples of the moiety —$C(R^{a1'})(R^{a2'})(R^{a3'})$— include the following groups.

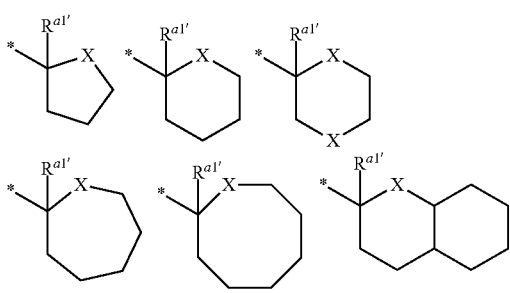

In each formula, $R^{1'}$ and X are as defined above.

At least one of $R^{a1'}$ and $R^{a2'}$ is preferably a hydrogen atom.

Examples of the group represented by the formula (2) include the following.

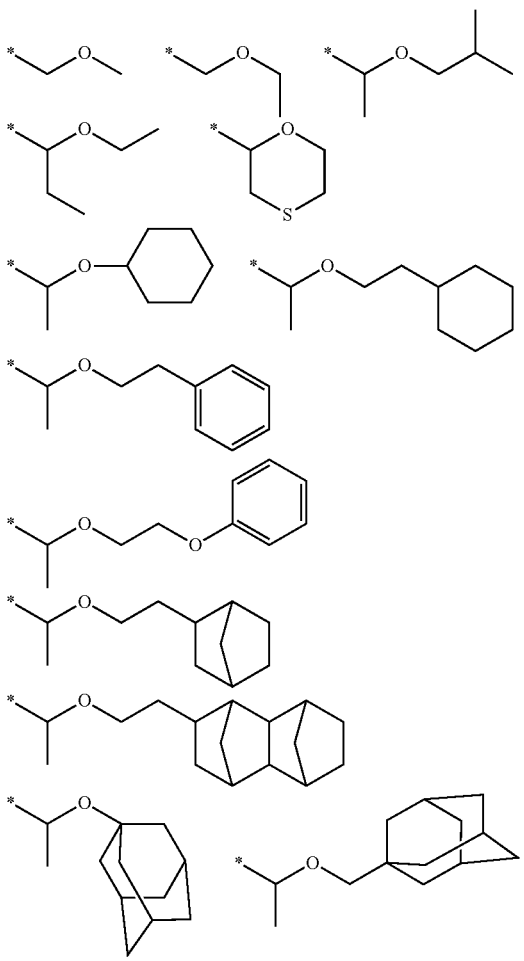

The structural unit (a1) is derived from a compound having an acid-labile group which compound is sometimes referred to as "Monomer (a1)".

Monomer (a1) is preferably a monomer having an acid-labile group and an ethylenic unsaturated group, more preferably a (meth)acrylate monomer having an acid-labile group, and still more preferably a (meth)acrylate monomer having the group represented by formula (1) or (2).

The (meth)acrylate monomer having an acid-labile group is preferably those which have a C5 to C20 alicyclic hydrocarbon group. The resin which has a structural unit derived from such monomers can provide improved resolution for a photoresist pattern to be prepared therefrom.

The structural unit derived from a (meth)acrylate monomer having the group represented by formula (1) is preferably one of structural units represented by formulae (a1-0), (a1-1) and (a1-2):

(a1-0)

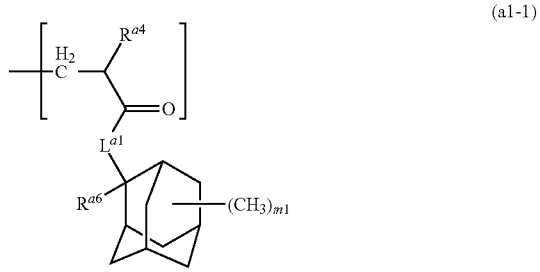

(a1-1)

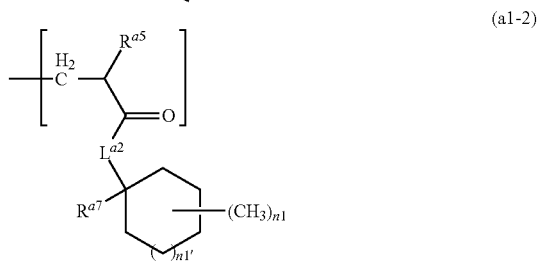

(a1-2)

where $L^{a01}$, $L^{a1}$ and $L^{a2}$ each independently represent —O— or

* —O—$(CH_2)_{k1}$—CO—O— in which k1 represents an integer of 1 to 7 and

* represents a binding site to —CO—, $R^{a01}$, $R^{a4}$ and $R^{a5}$ each independently represent a hydrogen atom or a methyl group, $R^{a02}$, $R^{a03}$, $R^{a04}$, $R^{a6}$ and $R^{a7}$ each independently represent a C1-C8 alkyl group, a C3-C20, preferably C3-C18, alicyclic hydrocarbon group, or a group formed by combining them, m1 represents an integer of 0 to 14, n1 represents an integer of 0 to 10, and n1' represents an integer of 0 to 3.

Hereinafter, the structural units represented by formulae (a1-0), (a1-1) and (a1-2) are respectively referred to as "structural unit (a1-0)", "structural unit (a1-1)" and "structural unit (a1-2)". Resin (A) may have two or more of these structural units.

$L^{a01}$ is preferably *—O— or *—O—$(CH_2)_n$—CO—O— in which * represents a binding site to —CO—, and f1 represents an integer of 1 to 4, and is more preferably *—O— or *—O—$CH_2$—CO—O—, and is especially preferably *—O—.

$R^{a01}$ is preferably a methyl group.

For $R^{a02}$, $R^{a03}$ and $R^{a04}$, examples of the alkyl group, the alicyclic hydrocarbon group and the group formed by combining them include the same as referred for $R^{a1}$, $R^{a2}$ and $R^{a3}$.

The alkyl group preferably has 1 to 6 carbon atoms.

The alicyclic hydrocarbon group preferably has 3 to 8 carbon atoms and more preferably 3 to 6 carbon atoms. The alicyclic hydrocarbon group is preferably a saturated aliphatic cyclic hydrocarbon group.

The group formed by combining them preferably has 18 carbon atoms or less in total, examples of which include a methylcyclohexyl group, a dimethylcyclohexyl group, and a methylnorbornyl group. Each of $R^{a02}$ and $R^{a03}$ is preferably a C1-C6 alkyl group, more preferably a methyl group and an ethyl group.

$R^{a04}$ is preferably a C1 to C6 alkyl group and a C5 to C12 alicyclic hydrocarbon group, more preferably a methyl group, an ethyl group, a cyclohexyl group, and an adamantyl group.

Each of $L^{a1}$ and $L^{a2}$ is preferably *—O— or *—O—$(CH_2)_{f1}$—CO—O— in which * represents a binding site to —CO—, and f1 is the same as defined above, and is more preferably *—O— or *—O—$CH_2$—CO—O—, and is especially preferably *—O—.

Each of $R^{a4}$ and $R^{a5}$ is preferably a methyl group.

For $R^{a6}$ and $R^{a7}$, examples of the alkyl group, the alicyclic hydrocarbon group and the group composed of them include the same as referred for $R^{a1}$, $R^{a2}$ and $R^{a3}$.

The alkyl group represented by $R^{a6}$ and $R^{a7}$ is preferably a C1 to C6 alkyl group.

The alicyclic hydrocarbon group represented by $R^{a6}$ and $R^{a7}$ is preferably a C3 to C8 alicyclic hydrocarbon group, more preferably a C3 to C6 alicyclic hydrocarbon group.

The "m1" is preferably an integer of 0 to 3, more preferably 0 or 1. The "n1" is preferably an integer of 0 to 3, more preferably 0 or 1. The "n1'" is preferably 0 or 1.

Examples of the structural unit (a1-0) include those represented by formulae (a1-0-1) to (a1-0-12), preferably those represented by formulae (a1-0-1) to (a1-0-10).

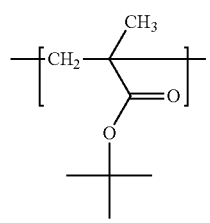
(a1-0-1)

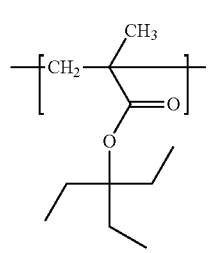
(a1-0-2)

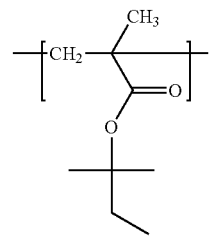
(a1-0-3)

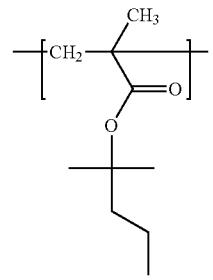
(a1-0-4)

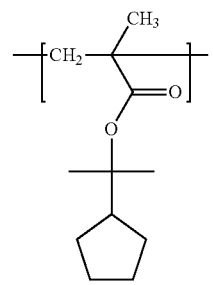
(a1-0-5)

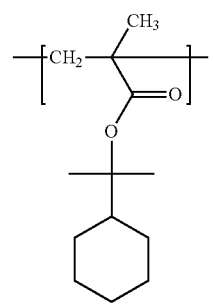
(a1-0-6)

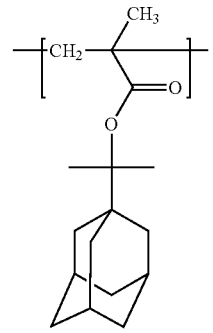
(a1-0-7)

-continued (a1-0-8)
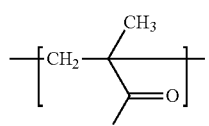

(a1-0-9)
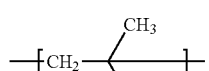

(a1-0-10)
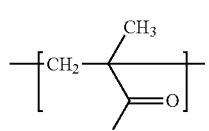

(a1-0-11)
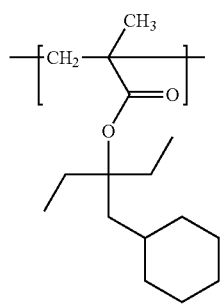

(a1-0-12)
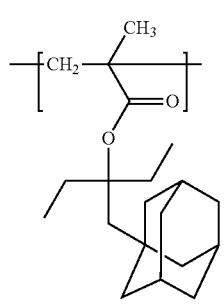

Examples of the structural unit (a1-0) further include such groups that a methyl group corresponding to $R^{a01}$ has been replaced by a hydrogen atom in the formulae (a1-0-1) to (a1-0-12).

Examples of the monomer from which the structural unit (a1-1) is derived include the monomers described in JP2010-204646A1, and the following monomers represented by the formulae (a1-1-1) to (a1-1-8), preferably the following monomers represented by the formulae (a1-1-1) to (a1-1-4).

(a1-1-1)
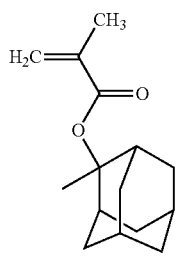

(a1-1-2)
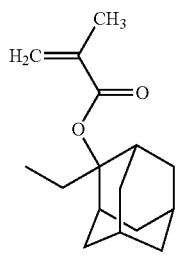

(a1-1-3)
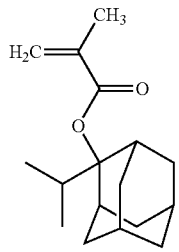

(a1-1-4)
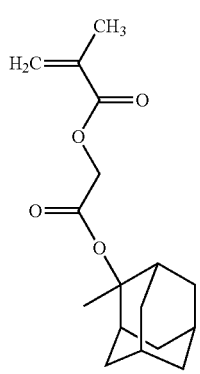

(a1-1-5)
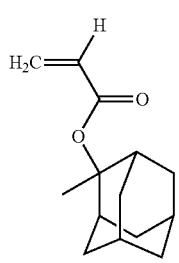

(a1-1-6)
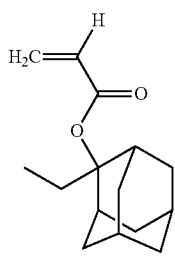

(a1-1-7)
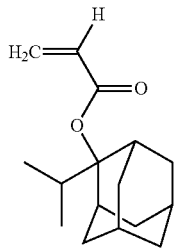

(a1-1-8)
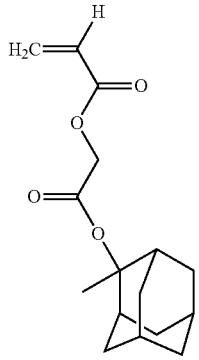

Examples of the monomer from which the structural unit (a1-2) is derived include 1-ethylcyclopentan-1-yl acrylate, 1-ethylcyclopentan-1-yl methacrylate, 1-ethylcyclohexan-1-yl acrylate, 1-ethylcyclohexan-1-yl methacrylate, 1-ethylcycloheptan-1-yl acrylate, 1-ethylcycloheptan-1-yl methacrylate, 1-methylcyclopentan-1-yl acrylate, 1-methylcyclopentan-1-yl methacrylate, 1-isopropylcyclopentan-1-yl acrylate and 1-isopropylcyclopentan-1-yl methacrylate, preferably the monomers represented by the formulae (a1-2-1) to (a1-2-12), more preferably the monomers represented by the formulae (a1-2-3), (a1-2-4), (a1-2-9) and (a1-2-10), still more preferably the monomers represented by the formulae (a1-2-3) and (a1-2-9).

(a1-2-1)
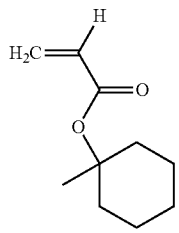

(a1-2-2)
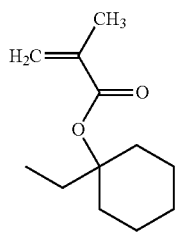

(a1-2-3)
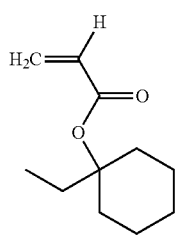

(a1-2-4)
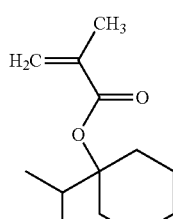

(a1-2-5)
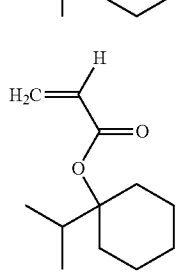

(a1-2-6)
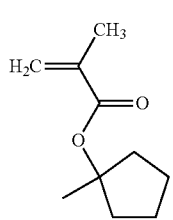

(a1-2-7)
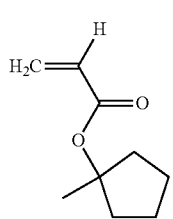

(a1-2-8)

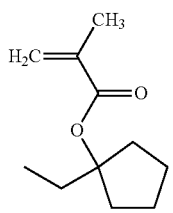 (a1-2-9)

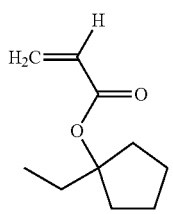 (a1-2-10)

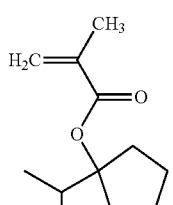 (a1-2-11)

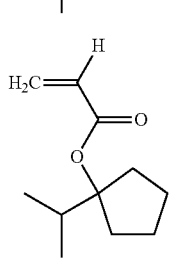 (a1-2-12)

When the resin has one or more of the structural units represented by the formulae (a1-0), (a1-1) and (a1-2), the total content of the structural units is preferably 10 to 95% by mole and more preferably 15 to 90% by mole and still more preferably 20 to 85% by mole based on all the structural units of the resin.

Other examples of the structural unit (a1) having a group of formula (1) include one represented by the formula (a1-3):

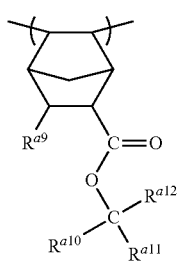 (a1-3)

wherein $R^{a9}$ represents a hydrogen atom, a carboxyl group, a cyano group, a C1 to C3 aliphatic hydrocarbon group which can have a hydroxyl group, or a group represented by —COOR$^{a13}$ group in which $R^{a13}$ represents a C1 to C8 aliphatic hydrocarbon group or a C3 to C20 alicyclic hydrocarbon group, and a group composed of a C1 to C8 aliphatic hydrocarbon group and a C3 to C20 alicyclic hydrocarbon group, and the aliphatic hydrocarbon group and the alicyclic hydrocarbon group can have a hydroxyl group, and a methylene in the aliphatic hydrocarbon group and the alicyclic hydrocarbon group can be replaced by —O— or —CO—, $R^{a10}$, $R^{a11}$ and $R^{a17}$ each independently represent a C1 to C8 alkyl group or a C3 to C20 alicyclic hydrocarbon group, and $R^{a10}$ and $R^{a11}$ can be bonded each other to form a C3 to C20 ring together with the carbon atom to which $R^{a10}$ and $R^{a11}$ are bonded, and the alkyl group and the alicyclic hydrocarbon group can have a hydroxyl group, and a methylene group in the alkyl group and the alicyclic hydrocarbon group can be replaced by —O— or —CO—.

As $R^{a9}$, examples of the alkyl group which can have a hydroxyl group include a methyl group, an ethyl group, a propyl group, a hydroxymethyl group and a 2-hydroxyethyl group.

Examples of the aliphatic hydrocarbon group represented by $R^{a13}$ include a methyl group, an ethyl group and a propyl group.

Examples of the alicyclic hydrocarbon group represented by $R^{a13}$ include a cyclopropyl group, a cyclobutyl group, an adamantyl group, an adamantylmethyl group, a 1-adamantyl-1-methylethyl group, a 2-oxo-oxolan-3-yl group and a 2-oxo-oxolan-4-yl group. As to $R^{a10}$, $R^{a11}$ and $R^{a12}$, examples of the alkyl group, the alicyclic hydrocarbon group and the group formed by combining them include the same as referred for $R^{a1}$, $R^{a2}$ and $R^{a3}$.

When the divalent hydrocarbon group is formed by bonding $R^{a10}$ and $R^{a11}$, examples of —C($R^{a10}$)($R^{a11}$)($R^{a12}$) include the following ones;

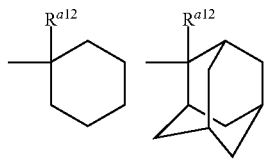

where $R^{a12}$ is as defined above.

Examples of the monomer from which the structural unit represented by the formula (a1-3) is derived include tert-butyl 5-norbornene-2-carboxylate, 1-cyclohexyl-1-methylethyl 5-norbornene-2-carboxylate, 1-methylcyclohexyl 5-norbornene-2-carboxylate, 2-methyl-2-adamantyl 5-norbornene-2-carboxylate, 2-ethyl-2-adamantyl 5-norbornene-2-carboxylate, 1-(4-methylcyclohexyl)-1-methylethyl 5-norbornene-2-carboxylate, 1-(4-hydroxycyclohexyl)-1-methylethyl 5-norbornene-2-carboxylate, 1-methyl-1-(4-oxocyclohexyl)ethyl 5-norbornene-2-carboxylate and 1-(1-adamantyl)-1-methylethyl 5-norbornene-2-carboxylate.

When the resin has a structural unit represented by the formula (a1-3), the photoresist composition having excellent resolution and higher dry-etching resistance tends to be obtained.

When Resin (A) has the structural unit represented by the formula (a1-3), the content of the structural unit is usually 10 to 95% by mole and preferably 15 to 90% by mole and more preferably 20 to 85% by mole based on all the structural units of the resin. Other examples of the structural unit (a1) having a group of formula (2) include one represented by the formula (a1-4):

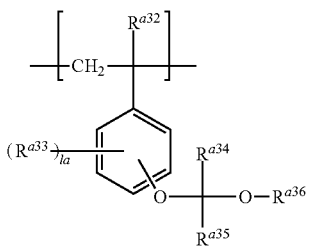

(a1-4)

wherein $R^{a32}$ represents a hydrogen atom, a halogen atom, a C1 to C6 alkyl group or a C1 to C6 halogenated alkyl group, $R^{a33}$ is independently in each occurrence a halogen atom, a hydroxy group, a C1 to C6 alkyl group, a C1 to C6 alkoxy group, a C2 to C4 acyl group, a C2 to C4 acyloxy group, an acryloyl group or a methacryloyl group, la represents an integer of 0 to 4, $R^{a34}$ and $R^{a35}$ each independently represent a hydrogen atom or a C1 to C12 hydrocarbon group, $R^{a36}$ represents a C1 to C20 hydrocarbon group in which a methylene group can be replaced by —O— or —S—, and $R^{a35}$ and $R^{a36}$ are bonded to each other to jointly represent a C3 to C20 divalent hydrocarbon group in which a methylene group can be replaced by —O— or —S—.

Examples of the alkyl group represented by $R^{a32}$ and $R^{a33}$ include a methyl group, an ethyl group, a propyl group, a butyl group, a pentyl group, and a hexyl group, preferably a C1 to C4 alkyl group, more preferably a methyl group and an ethyl group, and still more preferably a methyl group.

Examples of halogen atom represented by $R^{a32}$ and $R^{a33}$ include a fluorine atom, a chlorine atom, and a bromine atom.

Examples of the alkoxy group represented by $R^{a33}$ include a methoxy group, an ethoxy group, a propoxy group, an isopropoxy group, a butoxy group, an isobutoxy group, a sec-butoxy group, a tert-butoxy group, a pentyloxy group and a hexyloxy group.

Examples of the acyl group represented by $R^{a33}$ include an acetyl group, a propyonyl group and a butyryl group, and examples of the acyloxy group represented by $R^{a33}$ include an acetyloxy group, a propyonyloxy group and a butyryloxy group.

Examples of the groups represented by $R^{a34}$ and $R^{a35}$ include those as referred to for $R^{a1'}$ and $R^{a2'}$.

Examples of the groups represented by $R^{a36}$ include those as referred to for $R^{3'}$.

$R^{a32}$ preferably represents a hydrogen atom.

$R^{a33}$ is preferably a C1-C4 alkoxy group, more preferably a methoxy group and an ethoxy group, and still more preferably a methoxy group.

The symbol "la" preferably represents 0 or 1, more preferably 1. Examples of the groups represented by $R^{a34}$, $R^{a35}$ and $R^{a36}$ includes the same as the groups represented by $R^{a1'}$, $R^{a2'}$ and $R^{a3'}$, respectively.

$R^{a34}$ preferably represents a hydrogen atom.

$R^{a35}$ is preferably a C1-C12 monovalent hydrocarbon group, more preferably a methyl group and an ethyl group.

The hydrocarbon group represented by $R^{a36}$ includes a C1 to C18 alkyl group, a C3 to C18 monovalent alicyclic hydrocarbon group, a C6 to C18 monovalent aromatic hydrocarbon group, and any combination of them, and preferably a C1 to C18 alkyl group, a C3 to C18 monovalent alicyclic hydrocarbon group and a C7 to C18 aralkyl group.

These groups may be unsubstituted or substituted. The alkyl group and the monovalent alicyclic hydrocarbon group are preferably unsubstituted. As the substituent for the monovalent aromatic hydrocarbon group, a C6 to C10 aryloxy group is preferred.

Examples of the monomer from which the structural unit represented by formula (a1-4) is derived include monomers recited in JP2010-204646A1. Among them, the monomers represented by formulae (a1-4-1), (a1-4-2), (a1-4-3), (a1-4-4), (a1-4-5), (a1-4-6), (a1-4-7) and (a1-4-8) are preferred, and the monomers represented by formulae (a1-4-1), (a1-4-2), (a1-4-3), (a1-4-4), (a1-4-5) and (a1-4-8) are more preferred.

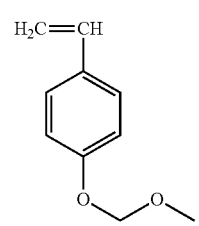

(a1-4-1)

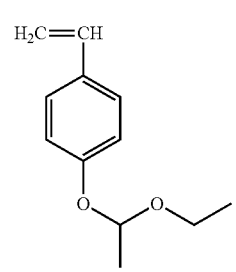

(a1-4-2)

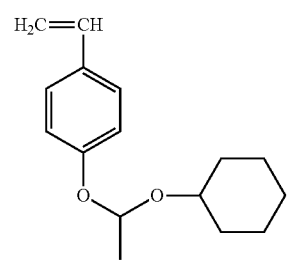

(a1-4-3)

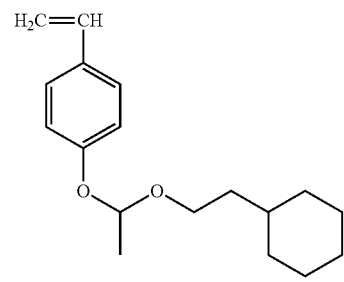

(a1-4-4)

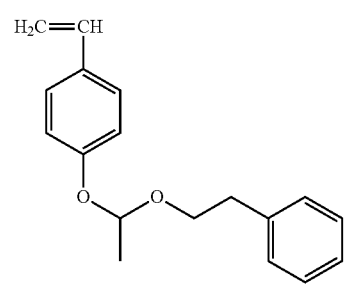

(a1-4-5)

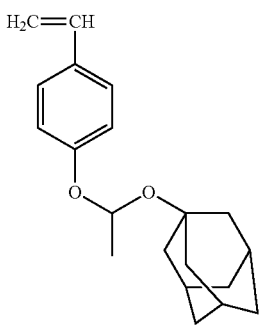
(a1-4-6)

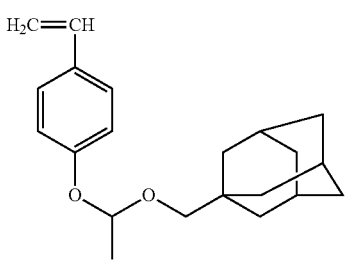
(a1-4-7)

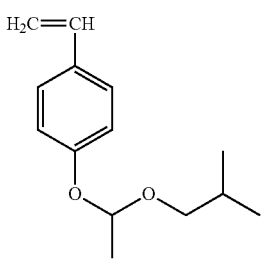
(a1-4-8)

When Resin (A) has a structural unit represented by formula (a1-4), its content is usually 10 to 95% by mole, preferably 15 to 90% by mole and more preferably 20 to 85% by mole based on 100% by mole of all the structural units of the resin.

Other examples of the structural unit having an acid-labile group include one represented by the formula (a1-5):

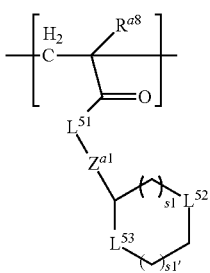
(a1-5)

In formula (a1-5) $R^{a8}$ represents a hydrogen atom, a halogen atom, or a C1 to C6 alkyl group which may have a halogen atom, $Z^{a1}$ represents a single bond or *—$(CH_2)_{h3}$—CO-$L^{54}$- in which h3 represents an integer of 1 to 4 and * represents a binding site to $L^{51}$, $L^{51}$, $L^{52}$, $L^{53}$ and $L^{54}$ each independently represent an oxygen atom or a sulfur atom, s1 represents an integer of 1 to 3, and s1' represents an integer of 0 to 3.

Herein, the structural unit represented by formula (a1-5) is sometimes referred to as "structural unit (a1-5)".

Examples of halogen atoms include a fluorine atom and a chlorine atom, preferably a fluorine atom.

Examples of the alkyl group which may have a halogen atom include a methyl group, an ethyl group, n-propyl group, an isopropyl group, an n-butyl group, a sec-butyl group, a tert-butyl group, a pentyl group, a hexyl group, a heptyl group, a 2-ethylhexyl group, an octyl group, a fluoromethyl group, and a trifluoromethyl group. In the formula (a1-5), $R^{a5}$ preferably represents a hydrogen atom, a methyl group, or a trifluoromethyl group.

$L^{51}$ represents preferably an oxygen atom.

One of $L^{52}$ and $L^{53}$ represents preferably an oxygen atom, while the other represents a sulfur atom.

s1 preferably represents 1. s1' represents an integer of 0 to 2.

$Z^{a1}$ preferably represents a single bond or *—$CH_2$—CO—O— wherein * represents a binding site to $L^{51}$.

Examples of the monomer from which the structural unit (a1-5) is derived include the following ones:

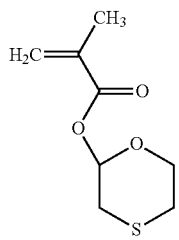
(a1-5-1)

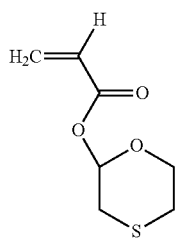
(a1-5-2)

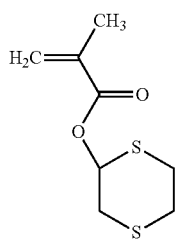
(a1-5-3)

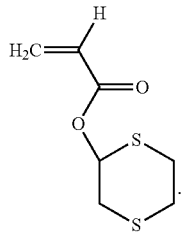
(a1-5-4)

When Resin (A) has a structural unit (a1-5), its content is usually 1 to 50% by mole, preferably 3 to 45% by mole and more preferably 5 to 40% by mole based on 100% by mole of all the structural units of the resin.

Resin (A) has preferably one or more of the structural units (a1-0), (a1-1), (a1-2) and (a1-5), more preferably two or more of these structural units.

Specifically, it has preferably the structural units (a1-1) and (a1-2), the structural units (a1-1) and (a1-5), the structural units (a1-1) and (a1-0), the structural units (a1-2) and (a1-0), the structural units (a1-5) and (a1-0), the structural units (a1-0), (a1-1) and (a1-2), or the structural units (a1-0), (a1-1) and (a1-5), more preferably the structural units (a1-1) and (a1-2) or the structural units (a1-1) and (a1-5).

Resin (A) has preferably the structural unit (a1-1).

The content of the structural unit (a1) is usually 10 to 80% by mole and preferably 20 to 60% by mole, based on all the structural units of Resin (A).

Resin (A) preferably has a structural unit which generates an acid by being decomposed by exposure which structural unit is referred to as "structural unit (II)".

The structural unit (II) preferably has a group represented by formula (II-1) or (II-2).

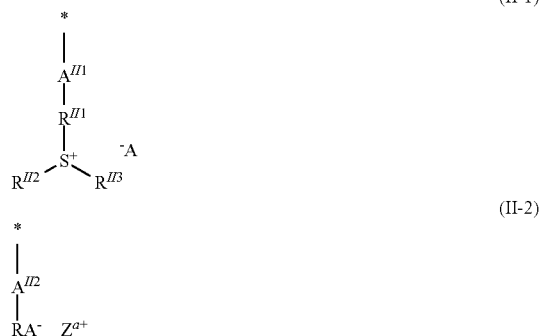

In each formula,
$A^{II1}$ and $A^{II2}$ each independently represent a single bond or a divalent connecting group;
$R^{II1}$, $R^{II2}$ and $R^{II3}$ each independently represent an organic group, or $R^{II2}$ and $R^{II3}$ can be bonded each other to form a ring together with $S^+$ bonded to them;
A represents a counter anion;
$RA^-$ represents an organic group having an anion; and
* represents a binding site.

The divalent connecting group represented by $A^{II1}$ and $A^{II2}$ is not limited, examples of which include a divalent hydrocarbon group which may have a substituent.

The divalent hydrocarbon group for $A^{II1}$ and $A^{II2}$ includes a C1 to C30 aliphatic hydrocarbon group, a C3 to C36 alicyclic hydrocarbon group, a C6 to C36 aromatic hydrocarbon group, and combination of them.

In these hydrocarbon groups, a methylene group can be replaced by a hetero atom, a carbonyl group or a sulfonyl group.

The aliphatic hydrocarbon group may be a linear one or a branched one. The aliphatic hydrocarbon group preferably has 1 to 10, more preferably 1 to 8, still more preferably 1 to 5 carbon atoms. Examples of the linear aliphatic hydrocarbon group include a linear alkanediyl group such as —CH$_2$—, —(CH$_2$)$_2$—, —(CH$_2$)$_3$—, —(CH$_2$)$_4$— and —(CH$_2$)$_5$—.

Examples of the branched aliphatic hydrocarbon group include a branched alkanediyl group such as —CH(CH$_3$)—, —CH(CH$_2$CH$_3$)—, —C(CH$_3$)$_2$—, —C(CH$_3$)(CH$_2$CH$_3$)—, —C(CH$_3$)(CH$_2$CH$_2$CH$_3$)—, —C(CH$_2$CH$_3$)$_2$—, —CH(CH$_3$)CH$_2$—, —CH(CH$_3$)CH(CH$_3$)—, —C(CH$_3$)$_2$CH$_2$—, —CH(CH$_2$CH$_3$)CH$_2$—, —C(CH$_3$)$_2$CH$_2$—, —CH(CH$_3$)CH$_2$CH$_2$—, —CH$_2$CH(CH$_3$)CH$_2$—, —CH(CH$_3$)CH$_2$CH$_2$CH$_2$— and —CH$_2$CH(CH$_3$)CH$_2$CH$_2$—.

Examples of the alicyclic hydrocarbon group include a cycloalkyl group such as cyclopentyl, cyclohexyl, cycloheptyl, cyclooctyl groups; and polycyclic hydrocarbon groups such as decahydronaphtyl, adamantyl, norbornyl, isobornane, tricyclodecane and tetracyclododecane group.

The alicyclic hydrocarbon group has preferably 3 to 20 carbon atoms, more preferably 3 to 12 carbon atoms.

The alicyclic hydrocarbon group may be a monocyclic one or a polycyclic one.

Examples of the monocyclic aliphatic hydrocarbon group include cyclic groups in which two hydrogen atoms have been removed from a monocycloalkane. The monocycloalkane has preferably 3 to 6 carbon atoms, and specific examples of it include cyclopentane and cyclohexane.

Examples of the polycyclic aliphatic hydrocarbon group include cyclic groups in which two hydrogen atoms in a polycycloalkane have been removed. The polycyclic aliphatic hydrocarbon group has preferably 7 to 12 carbon atoms, and specific example of it include adamantane, norbornane, isobornane, tricyclodecane, and tetracyclododecane.

The aromatic hydrocarbon group represented by $A^{II1}$ or $A^{II2}$ is a divalent hydrocarbon group having a monocyclic or polycyclic aromatic ring.

The aromatic hydrocarbon group has preferably 4 to 30 carbon atoms, more preferably 5 to 20 carbon atoms, still more preferably 6 to 15 carbon atoms, further more preferably 6 to 12 carbon atoms, excluding the carbon atoms contained in a substituent on the ring. Examples of the aromatic ring include hydrocarbon rings such as benzene, naphthalene, anthracene, and phenanthrene; and the heterocyclic ring where a carbon atom has been replaced by a hetero atom in any one of these hydrocarbon rings.

Examples of a hetero atom within the heterocyclic ring include an oxygen atom, a sulfur atom and a nitrogen atom. Examples of the heterocyclic ring include a pyridine ring and a thiophene ring.

Examples of the divalent hydrocarbon group having a monocyclic or polycyclic aromatic ring include those consisting of the ring where two hydrogen atoms have been removed from an hydrocarbon or heterocyclic ring, specifically including an allylene group and heteroarylene group; and those composed of the ring where one hydrogen atom in an hydrocarbon or heterocyclic ring have been replaced by one alkanediyl group having preferably 1 to 4, more preferably 1 to 2 carbon atoms, still more preferably one carbon atom, specifically such a group that a hydrogen atom has been removed from the ring contained in a benzyl, a phenethyl group, 1-naphthylmethyl group, 2-naphthylmethyl group, 1-naphthylethyl group, or 2-naphthylethyl group.

The hetero atom in the hydrocarbon groups in formula (II-1) or (II-2) may be any atom except for a carbon atom and hydrogen atom, examples of which include an oxygen atom, a sulfur atom, a nitrogen atom and a halogen atom.

The hydrocarbon group which contains a hetero atom has a group such as —O—, —C(=O)—O—, —C(=O)—, —O—C(=O)—O—, —C(=O)—NH—, —NH—, —NH—C(=NH)—, —S—, —S(=O)$_2$—, —S(=O)$_2$—O—, -A$^{21}$-O-A$^{22}$-, -A$^{21}$-O-, -A$^{21}$-C(=O)—O—, -[A$^{21}$-C(=O)—O]$_{m'}$, -A$^{22}$- and -A$^{21}$-O—C(=O)-A$^{22}$-, where A$^{21}$ and A$^{22}$ are each independently a divalent hydrocarbon group which may have a substituent and m' is an integer of 0 to 3.

A hydrogen atom contained in —C(=O)—NH—, —NH—, and —NH—C(=NH)— can be replaced by a substituent such as an alkyl group and an acyl group which substituent has preferably 1 to 8 carbon atoms, more preferably 1 to 5 carbon atoms.

Examples of the divalent hydrocarbon group represented by $A^{21}$ and $A^{22}$ include the same ones as the above-mentioned divalent hydrocarbon group such as an aliphatic hydrocarbon group, an alicyclic hydrocarbon group and an aromatic hydrocarbon group.

$A^{21}$ is preferably a linear aliphatic hydrocarbon group, more preferably a linear alkanediyl group, still more preferably a C1 to C5 linear alkanediyl group, further more preferably a methylene group and an ethylene group.

$A^{21}$ is preferably a linear or branched chain aliphatic hydrocarbon group, preferably a methylene group, an ethylene group, or an alkylmethylene group. In the alkylmethylene group, the alkyl group is preferably a C1 to C5 linear alkyl group, more preferably a C1 to C3 linear alkyl group, and still more preferably a methyl group.

In $-[A^{21}-C(=O)-O]_{m'}-A^{22}-$, m' is preferably an integer of 0 to 2, more preferably 0 or 1, still more preferably 1. Thus, $-[A^{21}-C(=O)-O]_{m'}-A^{22}-$ is preferably $-A^{21}-C(=O)-O-A^{22}-$, more preferably one represented by $-(CH_2)_{a'}-C(=O)-O-(CH_2)_{b'}-$.

a' and b' are each independently preferably an integer of 1 to 8, more preferably an integer of 1 to 5, still more preferably an integer of 1 or 2, and further more preferably 1.

In formulae (II-1) and (11-2), an alicyclic hydrocarbon group where a methylene group has been replaced by an substituent, the substituent is preferably selected from among $-O-$, $-C(=O)-O-$, $-S-$, $(=O)_2-$, $-S(=O)_2-O-$.

In formulae (II-1) and (II-2), Examples of a substituent on the divalent hydrocarbon group include a halogen atom, a hydroxyl group, a C1 to C8 alkyl group, a C1 to C12 alkoxy group, a C1 to C8 halogenated alkyl group, and an oxo group (=O), preferably a fluorine atom, a C1 to C5 fluorinated alkyl group and an oxo group (=O).

The alkyl group has preferably 1 to 5 carbon atoms, preferred examples of which include a methyl group, an ethyl group, a propyl group, a n-butyl group and a tert-butyl group.

The alkoxy group has preferably 1 to 5 carbon atoms, preferred examples of which include a methoxy group, an ethoxy group, n-propoxy group, an iso-propoxy group, n-butoxy group, and a tert-butoxy group, and more preferred are a methoxy group and an ethoxy group. Examples of a halogen atom include a fluorine atom, a chlorine atom, a bromine atom, iodine atoms, and preferred is a fluorine atom.

Examples of the halogenated alkyl group include such a group that a hydrogen atom has been replaced by a halogen atom.

Preferably, $A^{II1}$ and $A^{II2}$ each independently represent a single bond, an ester bond [$-C(=O)-O-$], an ether bond [$-O-$], a linear or branched chain alkanediyl group, or a combination consisting of two or more of them.

In formulae (II-1) and (II-2), the organic group represented by has a carbon atom, which may have another atom than a carbon atom, such as a hydrogen atom, an oxygen atom, a nitrogen atom, a sulfur atom, a halogen atom including a fluorine atom and a chlorine atom.

The organic group includes an alkanediyl group which may have a substituent, and an arylene group which may have a substituent. The alkanediyl group may be a linear one, a branched one or a cyclic one, and preferably has 1 to 10, more preferably 1 to 5 carbon atoms. Examples of the alkanediyl group include a methylene group, an ethylene group, 1,3-propanediyl group, 1,2-propanediyl group, 1,4-butanediyl group, 1,3-butanediyl group, 1,5-pentanediyl group, a cyclopentanediyl group, a hexanediyl group, and a cyclohexanediyl group.

Examples of the substituent for the alkanediyl group include a halogen atom, an oxo group (=O), a cyano group, an alkyl group, an alkoxyalkyloxy group, an alkoxycarbonylalkyloxy group, $-C(=O)-O-R^{7"}$, $-O-C(=O)-R^{8"}$, $-O-R^{9"}$ and an aryl group. $R^{7"}$, $R^{8"}$ and $R^{9"}$ each independently represent a hydrogen atom or a hydrocarbon group. Examples of the halogen atom include a fluorine atom, a chlorine atom, iodine atoms, and a bromine atom, preferably a fluorine atom. The alkyl groups as a substituent for alkanediyl group may be linear, branched, or cyclic one, which has preferably 1 to 30 carbon atoms. The linear alkyl groups has preferably 1 to 20 carbon atoms, more preferably 1 to 15 carbon atoms, still more preferably 1 to 10 carbon atoms.

Examples of the linear alkyl group include a methyl group, an ethyl group, a propyl group, and a butyl group specifically, for example. A pentyl group, a hexyl group, a heptyl group, an octyl group, a nonyl group, a decyl group, a undecyl group, a dodecyl group, a tridecyl group, an isotridecyl group, a tetradecyl group, a pentadecyl group, a hexadecyl group, an isohexadecyl group, a heptadecyl group, an octadecyl group, a nonadecyl group, an icosyl group, a henicosyl group and a docosyl group.

The branched chain alkyl groups has preferably 3 to 20 carbon atoms, more preferably 3 to 15 carbon atoms, still more preferably 3 to 10 carbon atoms.

Examples of the branched chain alkyl group include 1-methylethyl group and 1-methylpropyl group, 2-methylpropyl group, 1-methylbutyl group, 2-methylbutyl group, 3-methylbutyl group, 1-ethylbutyl group, 2-ethylbutyl group, 1-methylpentyl group, 2-methylpentyl group, 3-methylpentyl group, and 4-methylpentyl group.

The cyclic chain alkyl group may be a monocyclic one or a polycyclic one, which has preferably 3 to 30 carbon atoms, more preferably 5 to 30 carbon atoms, still more preferably 5 to 20 carbon atoms, further more preferably 5 to 15 carbon atoms, still further more preferably 5 to 12 carbon atoms.

Examples of the cyclic chain alkyl group include such a group that one hydrogen atom has been removed from a monocycloalkane; and one hydrogen atom has been removed from a polycycloalkane including a bicycloalkane, a tricycloalkane and a tetracycloalkane.

Specific examples of the cyclic chain alkyl group include a monocyclic one such as a cyclopentyl group and a cyclohexyl group, and a polycyclic one such as an adamantyl group, a norbornyl group, an isobornyl group, a tricyclodecanyl group and a tetracyclododecanyl group. The cyclic chain alkyl group is preferably a polycyclic one, more preferably an adamantyl group.

The alkyl group as the substituent for the alkanediyl group has preferably 1 to 5 carbon atoms, examples of which include a methyl group, an ethyl group, a propyl group, n-butyl group, and a tert-butyl group.

Examples of the alkoxyalkyloxy group as a substituent for the alkylene group include those represented by $-O-C(R^{47})(R^{48})-O-R^{49}$ where $R^{47}$ and $R^{48}$ are a hydrogen atom, a chain alkyl group, and $R^{49}$ is an alkyl group.

In $R^{47}$ and $R^{48}$, the chain alkyl group has preferably 1 to 5 carbon atoms, which is preferably a methyl group or an ethyl group, and more preferably a methyl group.

Preferably, at least one of $R^{47}$ and $R^{48}$ is a hydrogen atom. In particular, one of $R^{47}$ and $R^{48}$ is a hydrogen atom and the other is a hydrogen atom or a methyl group.

The alkyl group of $R^{49}$ has preferably 1 to 15 carbon atoms, examples of which include a methyl group, an ethyl group, a propyl group, n-butyl group and a tert-butyl group.

The cyclic alkyl group of $R^{49}$ has preferably 4 to 15 carbon atoms, more preferably 4 to 12 carbon atoms, still more preferably 5 to 10 carbon atoms.

Examples of the cyclic alkyl group include such a group that one hydrogen atom has been removed from a monocycloalkane or a polycycloalkane including a bicycloalkane, a tricycloalkane and a tetracycloalkane. In the cyclic alkyl group, a hydrogen atom can be replaced by a C1 to C5 chain alkyl group, a fluorine atom, or a fluorinated alkyl group.

Specific examples of the cyclic chain alkyl group include a monocyclic one such as a cyclopentyl group and a cyclohexyl group, and a polycyclic one such as an adamantyl group, a norbornyl group, an isobornyl group, a tricyclodecanyl group and a tetracyclododecanyl group.

The cyclic chain alkyl group is preferably a polycyclic one, more preferably an adamantyl group.

Examples of the alkoxycarbonylalkyloxy group as a substituent for the alkylene group include those represented by —O—$R^{50}$—C(=O)—O—$R^{56}$ where $R^{50}$ is a chain alkanediyl group, $R^{56}$ is a tertiary alkyl group; those represented by —O—$R^{50}$—C(=O)—O—$R^{56'}$ where $R^{50}$ is as defined above, $R^{56'}$ is a hydrogen atom, an alkyl group, a fluorinated alkyl group or an alicyclic hydrocarbon group which may have a hetero atom.

In $R^{50}$, the chain alkanediyl group has preferably 1 to 5 carbon atoms. Examples of the alkanediyl group include a methylene group, an ethylene group, a trimethylene group, a tetramethylene group, 1,1-dimethylethylene group.

In $R^{56}$, examples of the tertiary alkyl group include a 2-methyl-2-adamanthyl group, a 2-(2-propyl)-2-adamanthyl group, a 2-ethyl-2-adamanthyl group, a 1-methyl-1-cyclopentylic group, a 1-ethyl-1-cyclopentylic group, a 1-methyl-1-cyclohexyl group, a 1-ethyl-1-cyclohexyl group, a 1-(1-adamanthyl)-1-methylethyl group, a 1-(1-adamanthyl)-1-methylpropyl group, a 1-(1-adamanthyl)-1-methylbutyl group, 1-(1-adamanthyl)-1-methyl pentyl group, a 1-(1-cyclopentyl)-1-methylethyl group, a 1-(1-cyclopentyl)-1-methylpropyl group, a 1-(1-cyclopentyl)-1-methylbutyl group, 1-(1-cyclopentyl)-1-methyl pentyl group; a 1-(1-cyclohexyl)-1-methylethyl group, a 1-(1-cyclohexyl)-1-methylpropyl group, a 1-(1-cyclohexyl)-1-methylbutyl group, a 1-(1-cyclohexyl)-1-methyl pentyl group, a tert-butyl group, a tert-pentyl group, and a tert-hexyl group.

Examples of the alkyl group represented by $R^{56'}$ include the same ones as those represented by $R^{49}$.

Examples of the alkyl group represented by $R^{56'}$ include such a group that a hydrogen atom has been replaced by a fluorine atom in the any one of the alkyl group represented by $R^{49}$ as mentioned above. Examples of the cyclic alkyl group include such a group that one hydrogen atom has been removed from a monocycloalkane or a polycycloalkane including a bicycloalkane, a tricycloalkane and a tetracycloalkane. In the cyclic alkyl group, a hydrogen atom can be replaced by a C1 to C5 chain alkyl group, a fluorine atom, or a fluorinated alkyl group.

Specific examples of the cyclic chain alkyl group include a monocyclic one such as a cyclopentyl group and a cyclohexyl group, and a polycyclic one such as an adamantyl group, a norbornyl group, an isobornyl group, a tricyclodecanyl group and a tetracyclododecanyl group. The cyclic chain alkyl group is preferably a polycyclic one, more preferably an adamantyl group.

As for $R^{56'}$, examples of the aliphatic hydrocarbon group having a hetero atom include an aliphatic hydrocarbon group having a hetero atom within its ring structure, and an aliphatic hydrocarbon group in which a hydrogen atom has been replaced by a hetero atom.

Specific examples of the aliphatic hydrocarbon group having a hetero atom within its ring structure include those as follow:

(L1)

(L2)

(L3)

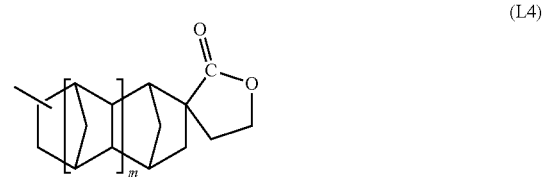
(L4)

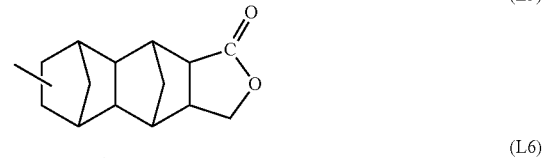
(L5)

(L6)

(S1)

(S2)

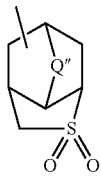
(S3)

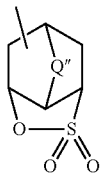
(S4)

where Q" represents an alkanediyl group, —O—, —S—, —O—R$^{94'}$— or —O—R$^{95'}$, R$^{94'}$ and R$^{95'}$ are each independently a C1 to C5 alkanediyl group, and m is an integer of 0 or 1.

Examples of the alkanediyl group represented by Q", R$^{94'}$ and R$^{95'}$ include the same ones as R$^{lll}$.

Specific examples of the aliphatic hydrocarbon group in which a hydrogen atom has been replaced by a hetero atom include those in which a hydrogen atom has been replaced by an oxo group (═O). The hydrocarbon group represented by R$^{7'''}$, R$^{8'''}$ and R$^{9'''}$ may be an aliphatic hydrocarbon group or an aromatic hydrocarbon group, which may have a substituent.

The aliphatic hydrocarbon group represented by R$^{7'''}$, R$^{8'''}$ and R$^{9'''}$ may be an aliphatic saturated hydrocarbon group or an aliphatic unsaturated hydrocarbon group, and may be a linear one, a branched chain one, a cyclic one or any combinations of them.

As for R$^{7'''}$, R$^{8'''}$ and R$^{9'''}$, the linear or branched aliphatic hydrocarbon group has preferably 1 to 25 carbon atoms, more preferably 1 to 15 carbon atoms, and still more preferably 4 to 10 carbon atoms. Examples of the linear aliphatic hydrocarbon group include a methyl group, an ethyl group, a propyl group, a butyl group, a pentyl group, a hexyl group, a heptyl group, an octyl group, a nonyl group, and a decyl group.

Examples of the branched chain aliphatic hydrocarbon group include the same ones as the tertiary alkyl group for R$^{56}$. Another example of it include 1-methylethyl group, 1-methylpropyl group, 2-methylpropyl group, 1-methylbutyl group, 2-methylbutyl group, 3-methylbutyl group, 1-ethylbutyl group, 2-ethylbutyl group, 1-methylpentyl group, 2-methylpentyl group, 3-methylpentyl group and 4-methylpentyl group.

Examples of the substituent for the linear or branched chain aliphatic hydrocarbon group include an alkoxy group, a halogen atom, an alkyl halide group, a hydroxyl group, an oxo group (═O), a cyano group, and a carboxy group.

The alkoxy group as the substituent has preferably 1 to 5 carbon atoms, examples of which include preferably a methoxy group, an ethoxy group, n-propoxy group, an iso-propoxy group, n-butoxy group and a tert-butoxy group, and more preferably a methoxy group and an ethoxy group.

Examples of the halogen atom as the substituent include a fluorine atom, a chlorine atom, a bromine atom and an iodine atom, preferably a fluorine atom.

Examples of the halogenated hydrocarbon group as the substituent include linear or branched chain aliphatic hydrocarbon groups in which a hydrogen atom has been replaced by the halogen atom as mentioned above.

As for R$^{7'''}$, R$^{8'''}$ and R$^{9'''}$, the cyclic aliphatic hydrocarbon group has preferably 3 to 20 carbon atoms.

The cyclic aliphatic hydrocarbon group may be any of a polycyclic group and a monocyclic group, examples of which include cyclic groups in which one hydrogen atom has been removed from a monocycloalkane; and cyclic groups in which one hydrogen atom has been removed from a polycycloalkane such as a bicycloalkane, a tricycloalkane and a tetracycloalkane.

Specific examples of the cyclic aliphatic hydrocarbon group include monocycloalkyl groups such as cyclopentyl group, a cyclohexyl group, a cycloheptyl group and a cyclooctyl group; and polycycloalkyl groups such as an adamantyl group, a norbornyl group, an isobornyl group, a tricyclodecyl group and a tetracyclododecyl group.

In the cyclic aliphatic hydrocarbon group represented by R$^{7'''}$, R$^{8'''}$ and R$^{9'''}$, a carbon atom of the ring can be replaced by a hetero atom, and a hydrogen atom of the ring can be replaced by a substituent. Examples of the cyclic aliphatic hydrocarbon group which has a hetero atom at the ring include cyclic groups in which one hydrogen atom has been removed from a heterocycloalkane, that is the group in which a hydrogen atom has been replaced by a hetero atom including an oxygen atom, a sulfur atom and a nitrogen atom in a monocycloalkane or polycycloalkane.

The cyclic aliphatic hydrocarbon group may have an ester bond (—C(═O)—O—) in its ring structure. Examples of such group include lactone-containing monocyclic groups such as a group in which a hydrogen atom has been removed from γ-butyrolactone; and lactone-containing polycyclic groups such as a group in which a hydrogen atom has been removed from a lactone-containing polycycloalkane such as bicycloalkanes, tricycloalkanes and tetracycloalkanes.

As for R$^{7'''}$, R$^{8'''}$ and R$^{9'''}$, examples of the substituent for the cyclic aliphatic hydrocarbon group include C1 to C5 alkyl groups and the same as that for the above-mentioned linear or branched chain alkyl groups.

As for R$^{7'''}$, R$^{8'''}$ and R$^{9'''}$, examples of the combination of these aliphatic hydrocarbon groups include a cyclic aliphatic hydrocarbon group having a linear or branched chain alkyl group as a substituent; and a linear or branched chain alkyl group having a cyclic alkyl group as a substituent, for example, 1-(1-adamanthyl) methyl group.

As for R$^{7'''}$, R$^{8'''}$ and R$^{9'''}$, the unsaturated aliphatic hydrocarbon groups is preferably a linear or branched chain one. Examples of the linear one include a vinyl group, a propenyl group (allyl group) and a butynyl group. Examples of the branched chain one include 1-methylpropenyl group and 2-methylpropenyl group.

These unsaturated aliphatic hydrocarbon groups may have a substituent examples of which include the same as that for the above-mentioned linear or branched chain alkyl groups.

The aromatic hydrocarbon group represented by R$^{7'}$, R$^{8'''}$ and R$^{9'''}$ is a divalent hydrocarbon group having an aromatic ring, which may has a substituent. The aromatic hydrocarbon group may be any of a monocyclic group and a polycyclic group.

The aromatic hydrocarbon group has preferably 5 to 30 carbon atoms, more preferably 5 to 20 carbon atoms, still more preferably 6 to 15 carbon atoms, further more preferably 6 to 12 carbon atoms, excluding the carbon atoms contained in a substituent on the ring. Examples of the aromatic ring include hydrocarbon rings such as benzene, naphthalene, anthracene, and phenanthrene; and the heterocyclic ring where a carbon atom has been replaced by a hetero atom in any one of these hydrocarbon rings.

Examples of a hetero atom within the heterocyclic ring include an oxygen atom, a sulfur atom and a nitrogen atom. Examples of the heterocyclic ring include a pyridine ring and a thiophene ring. Examples of the aromatic hydrocarbon group include those consisting of the ring where one hydrogen atom has been removed from the above-mentioned hydrocarbon or heterocyclic ring, specifically including an aryl group and a heteroaryl group; and those composed of the ring where one hydrogen atom in an hydrocarbon or heterocyclic ring have been replaced by one alkyl group having preferably 1 to 4, more preferably 1 to 2 carbon atoms, still more preferably one carbon atom, specifically arylalkyl groups such as a benzyl group, a phenethyl group, 1-naphthylmethyl group, 2-naphthylmethyl group, 1-naphthylethyl group or 2-naphthylethyl group.

Examples of the substituent for the aromatic hydrocarbon group include an alkyl group, an alkoxy group, a halogen atom, a halogenated alkyl group, a hydroxyl group and an oxo group (=O).

The alkyl group preferably has 1 to 5 carbon atoms, and is more preferably a methyl group, an ethyl group, a propyl group, an n-butyl group, or a tert-butyl group.

The alkoxy group preferably has 1 to 5 carbon atoms, and is more preferably a methoxy group, an ethoxy group, n-propoxy group, an iso-propoxy group, n-butoxy group, or a tert-butoxy group, still more preferably a methoxy group or an ethoxy group.

Examples of a halogen atom include a fluorine atom, a chlorine atom, a bromine atom and an iodine atom, and preferably a fluorine atom.

Examples of the halogenated alkyl group include those where a hydrogen atom of the above-mentioned alkyl group has been replaced by a halogen atom.

From the viewpoint of obtaining excellent lithography characteristic or excellent photoresist patterns, $R^{7\prime\prime}$, $R^{8\prime\prime}$ and $R^{9\prime\prime}$ is preferably a hydrogen atom, a saturated or unsaturated aliphatic hydrocarbon group, and more preferably a hydrogen atom, a C1 to C15 linear or branched chain aliphatic hydrocarbon group, or a C3 to C20 cyclic aliphatic hydrocarbon group.

—O—$R^{9\prime\prime}$ is preferably a hydrogen atom or a C1 to C5 alkoxy group, and more preferably a methoxy group, an ethoxy group, an n-propoxy group, an iso-propoxy group, an n-butoxy group, a tert-butoxy group. In the viewpoint of costs on synthesis, the aryl group as a substituent for the alkanediyl group represented by $A^{II1}$ has 6 to 10 carbon atoms, examples of which include a phenyl group and a naphthyl group. The aryl group may have a substituent examples of which include the same as those for the aromatic hydrocarbon group as mentioned above.

In the viewpoint of costs on synthesis, the arylene group represented by $A^{II1}$ has preferably 6 to 10 carbon atoms, examples of which include a phenylene group and a naphthylene group. The arylene group may have a substituent examples of which include the same as those for the substituted alkanediyl group as mentioned above.

In formula (I-1), the organic group represented by $R^{II2}$ and $R^{II3}$, which is not particularly limited, include aryl groups which may have a substituent, alkyl groups which may have a substituent, and alkenyl groups which may have a substituent.

In the viewpoint of costs on synthesis, the aryl groups represented by $R^{II2}$ and $R^{II3}$ has preferably 6 to 10 carbon atoms, examples of which include a phenylene group and a naphthylene group. Examples of the substituent for the aryl groups include the same as those for the arylene group as mentioned above.

The alkyl group represented by $R^{II2}$ and $R^{II3}$ may be any of a chain one and cyclic one. In the viewpoint of excellent resolution, the alkyl group has preferably 1 to 10 carbon atoms, examples of which include a methyl group, an ethyl group, n-propyl group, an isopropyl group, n-butyl group, an isobutyl group, an n-pentyl group, a cyclopentylic group, a hexyl group, a cyclohexyl group, a nonyl group and a decyl group.

Examples of the substituent for the alkyl groups include the same as those for the alkanediyl group as mentioned above.

The alkenyl group represented by $R^{II2}$ and $R^{II3}$ may be any of a chain one and cyclic one, which has preferably 2 to 10 carbon atoms, more preferably 2 to 5 carbon atoms, still more preferably 2 to 4 carbon atoms. Examples of the alkenyl group include a vinyl group, a propenyl group (allyl group), a butynyl group, 1-methylpropenyl group and 2-methylpropenyl group.

Examples of the substituent for the alkenyl groups include the same as those for the alkanediyl group as mentioned above.

In formula (II-1), the ring represented by $R^{II2}$, $R^{II3}$ and a sulfur atom together may be any of a monocyclic one and a polycyclic one, and may be any of a saturated one and an unsaturated one.

The ring represented by $R^{II2}$, $R^{II3}$ and a sulfur atom together is preferably a 3 to 10 membered-ring, and more preferably a 5 to 7 membered-ring.

This ring may further have another hetero atom than the sulfur atom bonded to $R^{II2}$ and $R^{II3}$. Examples of the another hetero atom include a sulfur atom, an oxygen atom and a nitrogen atom.

Examples of this ring include a thiophene ring, a thiazole ring, a benzothiophene ring, a thianthrene ring, a dibenzothiophene ring, a 9H-thoxanthene ring, a thioxanthone ring, a phenoxathiin ring, a tetrahydrothiophenium ring and a tetrahydrothiopiranium ring. In formula (II-1), $A^-$ represents a counter anion. Examples of the counter anion include a sulfonic acid anion, a sulfonylimide anion, a sulfonylmethide anion, and a carboxylic acid anion, preferably a sulfonic acid anion, more preferably an anion represented by formula (I-A):

(I-A)

wherein $Q^1$ and $Q^2$ each independently represent a fluorine atom or a C1-C6 perfluoroalkyl group,
$L^{b1}$ represents a single bond or a C1 to C40, preferably C1 to C24, divalent saturated hydrocarbon group where a methylene group can be replaced by an oxygen atom or a carbonyl group and where a hydrogen atom can be replaced by an fluorine atom or a hydroxy group, and Y represents a hydrogen atom or a C3-C18 alicyclic hydrocarbon group where a methylene group can be replaced by an oxygen atom, a sulfonyl group or a carbonyl group and where a hydrogen atom can be replaced by a substituent.

Examples of the perfluoroalkyl group represented by $Q^1$ and $Q^2$ include a trifluoromethyl group, a pentafluoroethyl group, a heptafluoropropyl group, a nonafluorobutyl group, an undecafluoropentyl group and a tridecafluorohexyl group. It is preferred that $Q^1$ and $Q^2$ each independently represent a fluorine atom or a trifluoromethyl group, and it is more preferred that $Q^1$ and $Q^2$ are fluorine atoms.

Examples of the divalent saturated hydrocarbon group represented by $L^{b1}$ include linear alkanediyl groups, branched chain alkanediyl groups, a monocyclic divalent alicyclic hydrocarbon group, a polycyclic divalent alicyclic hydrocarbon group and combinations of them.

Specific examples of them include
linear alkanediyl groups such as a methylene group, an ethylene group, a propane-1,3-diyl group, a butane-1,4-diyl group, a pentane-1, 5-diyl group, a hexane-1, 6-diyl group, a heptane-1, 7-diyl group, an octane-1,8-diyl group, a nonane-1,9-diyl group, a decane-1,10-diyl group, a undecane-1,11-diyl group, a dodecane-1,12-diyl group, a tridecane-1,13-diyl group, a tetradecane-1,14-diyl group, a pentadecane-1,15-diyl group, a hexadecane-1,16-diyl group and heptadecane-1,17-diyl group; branched chain alkanediyl groups such as an ethane-1,1-diyl group, a propane-1,1-diyl group, a propane-1,2-diyl group, a propane-2,2-diyl group, a pentane-2,4-diyl group, a 2-methylpropane-1,3-diyl group, a 2-methylpropane-1,2-diyl group, a pentane-1,4-diyl group and 2-methylbutane-1,4-diyl group; a monocyclic divalent alicyclic hydrocarbon group such as a cyclobutan-1,3-diyl group, cyclopentane-1,3-diyl group, a cyclohexane-1,4-diyl group, and a cyclooctane-1,5-diyl group; and a polycyclic divalent alicyclic hydrocarbon group such as a norbornane-1,4-diyl group, a norbornane-2,5-diyl group, an adamantane-1,5-diyl group and an adamantane-2,6-diyl group.

When $L^{b1}$ represents a divalent saturated hydrocarbon group in which a methylene group has been replaced by an oxygen atom or a carbonyl group, examples of $L^{b1}$ include the moiety represented by any one of formulae (b1-1) to (b1-3) as follow;

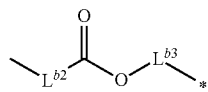

(b1-1)

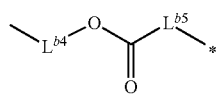

(b1-2)

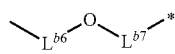

(b1-3)

wherein $L^{b2}$ represents a single bond or a C1 to C22 divalent saturated hydrocarbon group in which a hydrogen atom can be replaced by a fluorine atom, and
$L^{b3}$ represents a single bond or a C1 to C22 divalent saturated hydrocarbon group in which a hydrogen atom can be replaced by a fluorine atom or a hydroxyl group and in which a methylene group can be replaced by an oxygen atom or a carbonyl group, provided that the total number of the carbon atoms in $L^{b2}$ and $L^{b3}$ is up to 22;
$L^{b4}$ represents a single bond or a C1 to C22 divalent saturated hydrocarbon group in which a hydrogen atom can be replaced by a fluorine atom, and $L^{b5}$ represents a single bond or a C1 to C22 divalent saturated hydrocarbon group in which a hydrogen atom can be replaced by a fluorine atom or a hydroxyl group and in which a methylene group can be replaced by an oxygen atom or a carbonyl group, provided that the total number of the carbon atoms in $L^{b4}$ and $L^{b5}$ is up to 22;
$L^{b6}$ represents a C1 to C23 divalent saturated hydrocarbon group in which a hydrogen atom can be replaced by a fluorine atom or a hydroxyl group, and $L^{b7}$ represents a single bond or a C1 to C23 divalent saturated hydrocarbon group in which a hydrogen atom can be replaced by a fluorine atom or a hydroxyl group and in which a methylene group can be replaced by an oxygen atom or a carbonyl group, provided that the total number of the carbon atoms in $L^{b6}$ and $L^{b7}$ is up to 23; and * represents a binding site to Y.

In formula (b1-1) to formula (b1-3), when a methylene group has been replaced by an oxygen atom or a carbonyl group, the carbon number of the saturated hydrocarbon group corresponds to the number of the carbon atom before replacement.

Examples of the divalent saturated hydrocarbon group are the same examples as the divalent saturated hydrocarbon group of $L^{b1}$.

$L^{b2}$ is preferably a single bond.

$L^{b3}$ is preferably a C1 to C4 divalent saturated hydrocarbon group.

$L^{b4}$ is preferably a C1 to C8 divalent saturated hydrocarbon group where a hydrogen atom can be replaced by a fluorine atom.

$L^{b5}$ is preferably a single bond or a C1 to C8 divalent saturated hydrocarbon group.

$L^{b6}$ is preferably a single bond or a C1 to C4 divalent saturated hydrocarbon group where a hydrogen atom can be replaced by a fluorine atom.

$L^{b7}$ is preferably a single bond or a C1 to C18 divalent saturated hydrocarbon group where a hydrogen atom can be replaced by a fluorine atom or a hydroxy group, and where a methylene group can be replaced by an oxygen atom or a carbonyl group.

Among these, the group represented by the formula (b1-1) or the formula (b1-3) is preferred.

Examples of the divalent group represented by the formula (b1-1) include the following groups represented by formula (b1-4) to formula (b1-8):

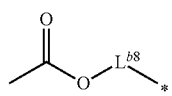

(b1-4)

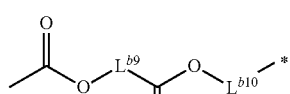

(b1-5)

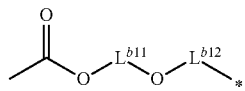

(b1-6)

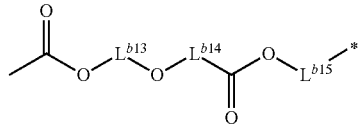

(b1-7)

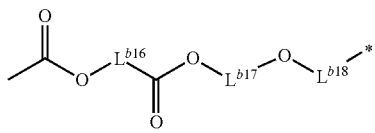

(b1-8)

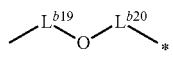

(b1-9)

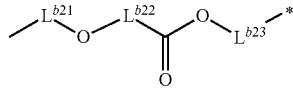

(b1-10)

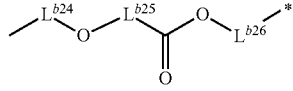

(b1-11)

wherein $L^{b8}$ represents a single bond or a C1 to C22 divalent saturated hydrocarbon group where a hydrogen atom can be replaced by a fluorine atom or a hydroxy group;
$L^{b9}$ represents a C1 to C20 divalent saturated hydrocarbon group, and $L^{b10}$ represents a single bond or a C1 to C19 divalent saturated hydrocarbon group where a hydrogen atom can be replaced by a fluorine atom or a hydroxy group, provided that the total number of carbon atoms contained in the group of $L^{b9}$ and $L^{b10}$ is 20 or less;
$L^{b11}$ represents a C1 to C21 divalent saturated hydrocarbon group, and $L^{b12}$ represents a single bond or a C1 to C20 divalent saturated hydrocarbon group where a hydrogen atom can be replaced by a fluorine atom or a hydroxy group, provided that the total number of carbon atoms contained in the group of $L^{b11}$ and $L^{b12}$ is 21 or less;
$L^{b13}$ represents a C1 to C19 divalent saturated hydrocarbon group, $L^{b14}$ represents a single bond or a C1 to C18 divalent saturated hydrocarbon group, and $L^{b15}$ represents a single bond or a C1 to C18 divalent saturated hydrocarbon group where a hydrogen atom can be replaced by a fluorine atom or a hydroxy group, provided that the total number of carbon atoms contained in the group of $L^{b13}$, $L^{b14}$ and $L^{b15}$ is 19 or less;
$L^{b16}$ represents a C1 to C18 divalent saturated hydrocarbon group, $L^{b17}$ represents a C1 to C18 divalent saturated hydrocarbon group, and $L^{b18}$ represents a single bond or a C1 to C17 divalent saturated hydrocarbon group where a hydrogen atom can be replaced by a fluorine atom or a hydroxy group, provided that the total number of carbon atoms contained in the group of $L^{b16}$, $L^{b17}$ and $L^{b18}$ is 19 or less; and * represents a binding site to Y.

$L^{b8}$ is preferably a C1 to C4 divalent saturated hydrocarbon group.
$L^{b9}$ is preferably a C1 to C8 divalent saturated hydrocarbon group.
$L^{b10}$ is preferably a single bond or a C1 to C19 divalent saturated hydrocarbon group, and more preferably a single bond or a C1 to C8 divalent saturated hydrocarbon group.
$L^{b11}$ is preferably a C1 to C8 divalent saturated hydrocarbon group.
$L^{b12}$ is preferably a single bond or a C1 to C8 divalent saturated hydrocarbon group.
$L^{b13}$ is preferably a C1 to C12 divalent saturated hydrocarbon group.
$L^{b14}$ is preferably a single bond or a C1 to C6 divalent saturated hydrocarbon group.
$L^{b15}$ is preferably a single bond or a C1 to C18 divalent saturated hydrocarbon group, and more preferably a single bond or a C1 to C8 divalent saturated hydrocarbon group.
$L^{b16}$ is preferably a C1 to C12 divalent saturated hydrocarbon group.
$L^{b17}$ is preferably a C1 to C6 divalent saturated hydrocarbon group.
$L^{b18}$ is preferably a single bond or a C1 to C17 divalent saturated hydrocarbon group, and more preferably a single bond or a C1 to C4 divalent saturated hydrocarbon group.

Examples of the divalent group represented by the formula (b1-3) include the following groups represented by formula (b1-9) to formula (b1-11):

wherein $L^{b19}$ represents a single bond or a C1 to C23 divalent saturated hydrocarbon group where a hydrogen atom can be replaced by a fluorine atom, and $L^{b20}$ represent a single bond or a C1 to C23 divalent saturated hydrocarbon group where a hydrogen atom can be replaced by a fluorine atom, a hydroxy group or an acyloxy group, and a methylene group contained in an acyloxy group can be replaced by an oxygen atom or a carbonyl group, and a hydrogen atom contained in an acyloxy group can be replaced by a hydroxy group, provided that the total number of carbon atoms contained in the group of $L^{b19}$ and $L^{b20}$ is 23 or less;
$L^{b21}$ represents a single bond or a C1 to C21 divalent saturated hydrocarbon group where a hydrogen atom can be replaced by a fluorine atom, $L^{b22}$ represents a single bond or a C1 to C21 divalent saturated hydrocarbon group, and $L^{b23}$ represents a single bond or a C1 to C21 divalent saturated hydrocarbon group where a hydrogen atom can be replaced by a fluorine atom, a hydroxy group or an acyloxy group, and a methylene group contained in an acyloxy group can be replaced by an oxygen atom or a carbonyl group, and a hydrogen atom contained in an acyloxy group can be replaced by a hydroxy group, provided that the total number of carbon atoms contained in the group of $L^{b21}$, $L^{b22}$ and $L^{b23}$ is 21 or less;
$L^{b24}$ represents a single bond or a C1 to C20 divalent saturated hydrocarbon group where a hydrogen atom can be replaced by a fluorine atom, $L^{b25}$ represents a single bond or a C1 to C21 divalent saturated hydrocarbon group, and $L^{b26}$ represents a single bond or a C1 to C20 divalent saturated hydrocarbon group where a hydrogen atom can be replaced by a fluorine atom, a hydroxy group or an acyloxy group, and a methylene group contained in an acyloxy group can be replaced by an oxygen atom or a carbonyl group, and a hydrogen atom contained in an acyloxy group can be replaced by a hydroxy group, provided that the total number of carbon atoms contained in the group of $L^{b24}$, $L^{b25}$ and $L^{b26}$ is 21 or less;
and * represents a binding site to Y.

In formula (b1-9) to formula (b1-11), when a hydrogen atom has been replaced by an acyloxy group, the carbon number of the saturated hydrocarbon group corresponds to the number of the carbon atom, CO and O in addition to the carbon number of the saturated hydrocarbon group.

Examples of the acyloxy group include acetyloxy, propionyloxy, butyryloxy, cyclohexyl carbonyloxy and adamantyl carbonyloxy groups.

Examples of the acyloxy group having a substituent include oxoadamantyl carbonyloxy, hydroxyadamantyl carbonyloxy, oxocyclohexyl carbonyloxyandhydroxycyclohexyl carbonyloxy groups. Examples of the group represented by the formula (b1-4) include the following ones:

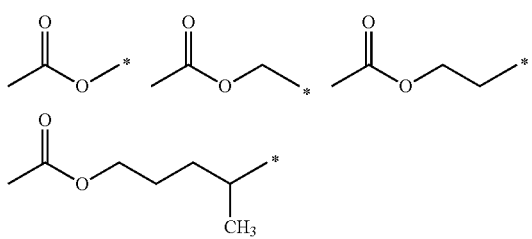
where * represents a binding site to Y.
Examples of the group represented by the formula (b1-5) include the following ones:
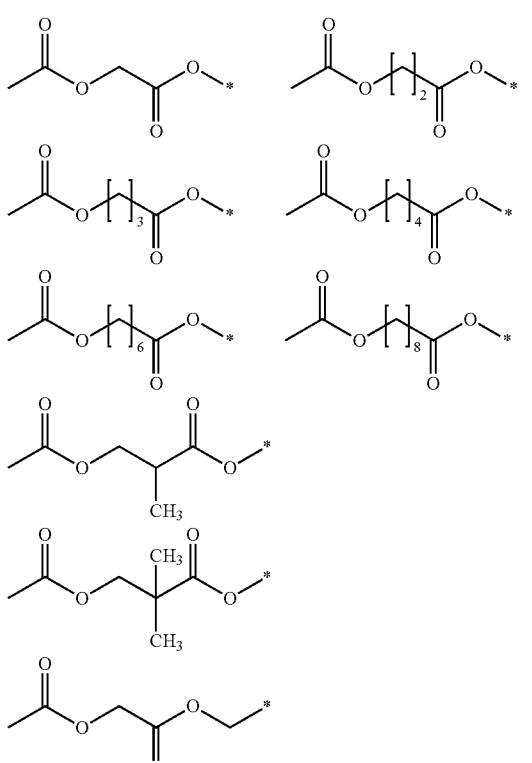
where * represents a binding site to Y.
Examples of the group represented by the formula (b1-6) include the following ones:
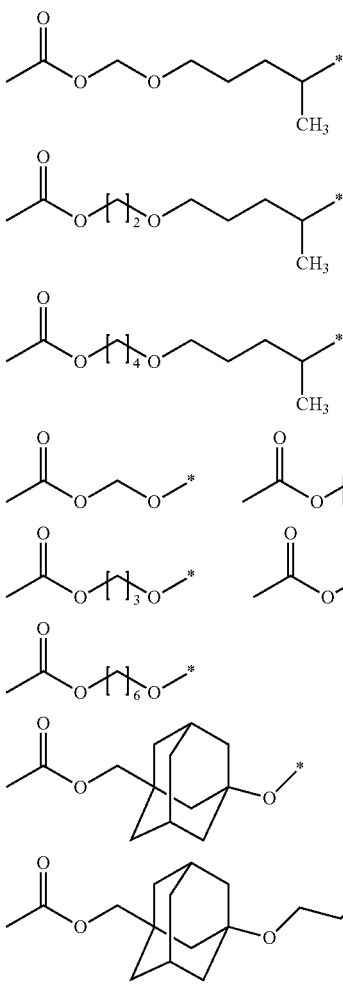
where * represents a binding site to Y.
Examples of the group represented by the formula (b1-7) include the following ones:
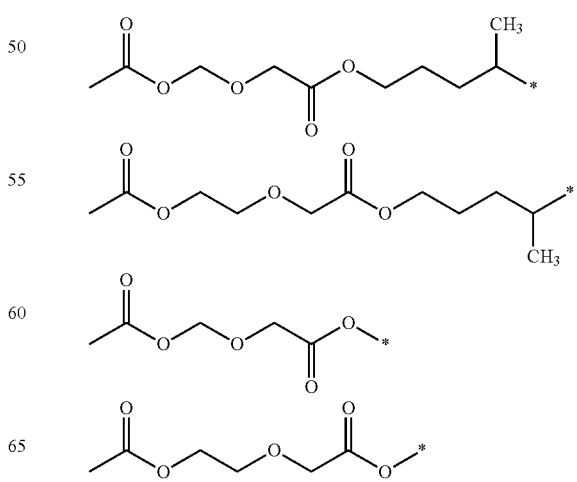

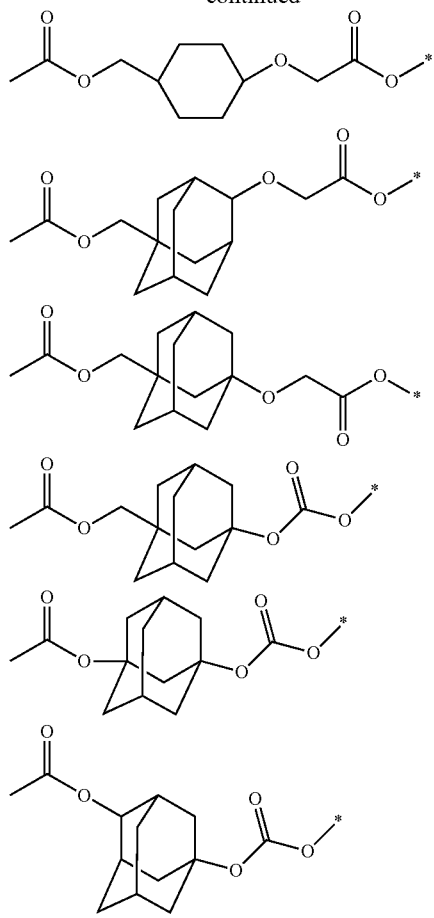
where * represents a binding site to Y.
Examples of the group represented by the formula (b1-8) include the following ones:
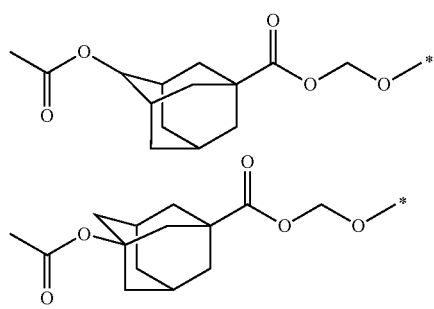
where * represents a binding site to Y.
Examples of the group represented by the formula (b1-2) include the following ones:
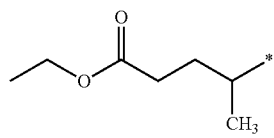
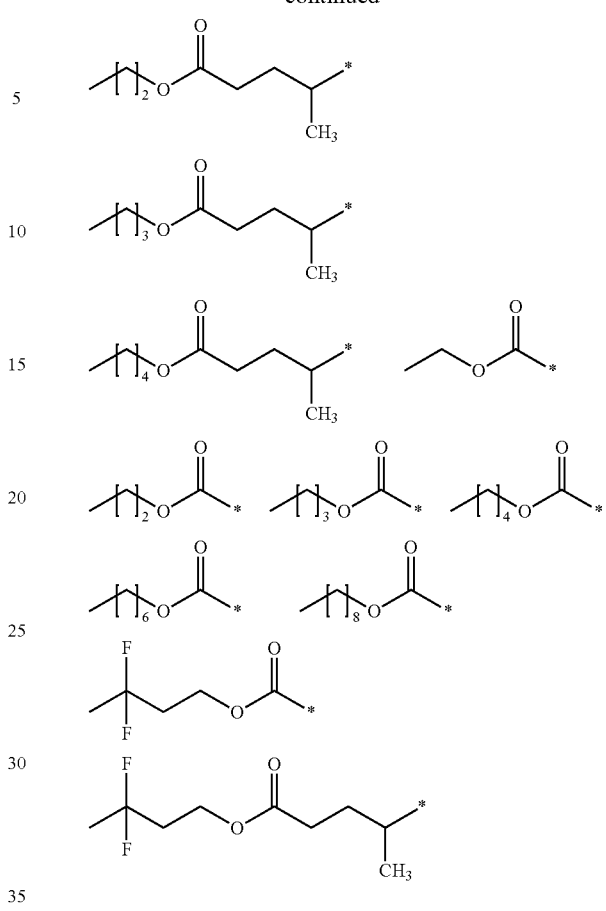
where * represents a binding site to Y.
Examples of the group represented by the formula (b1-9) include the following ones:
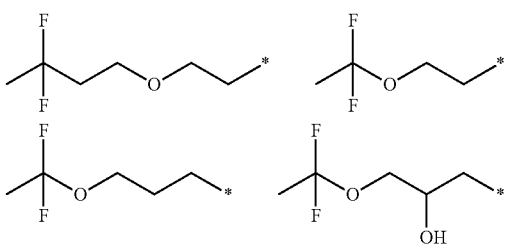

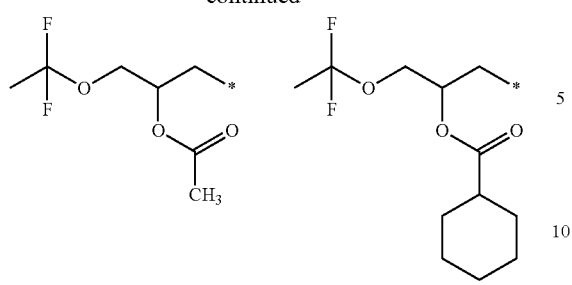
where * represents a binding site to Y.
Examples of the group represented by the formula (b1-10) include the following ones:
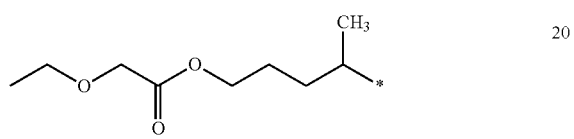
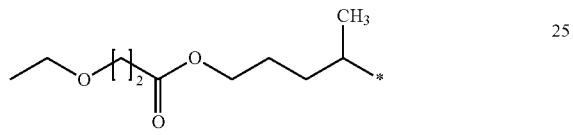
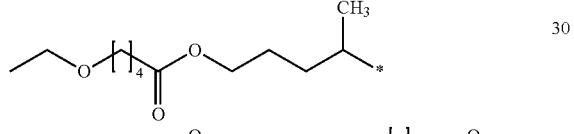
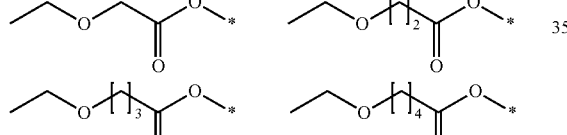
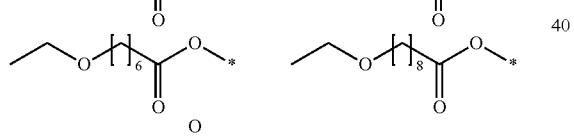
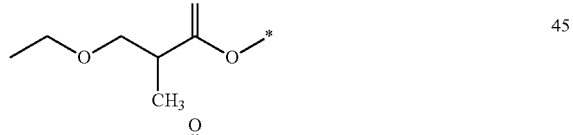
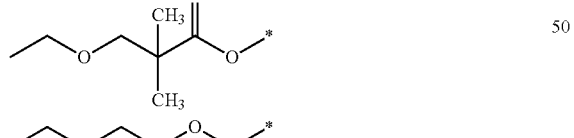
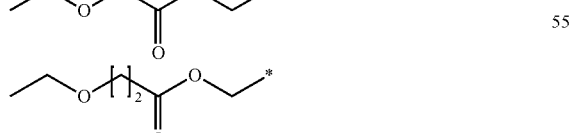
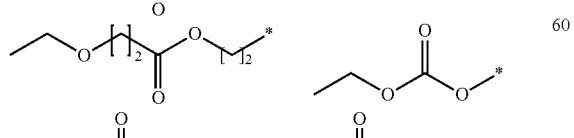
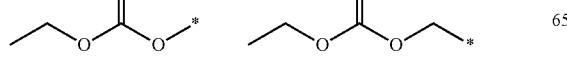
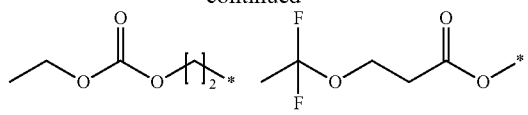
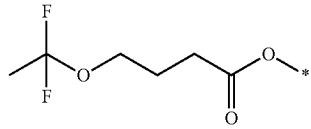
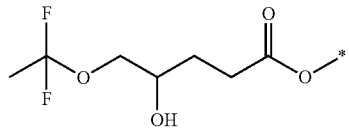
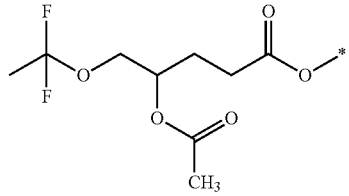
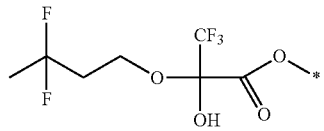
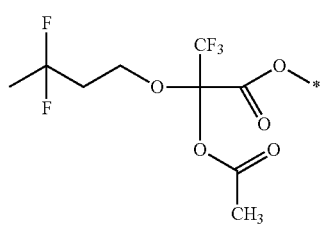
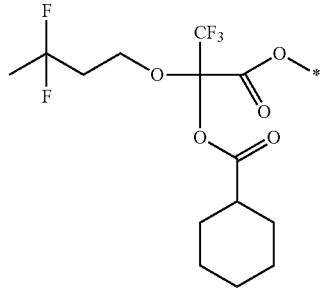
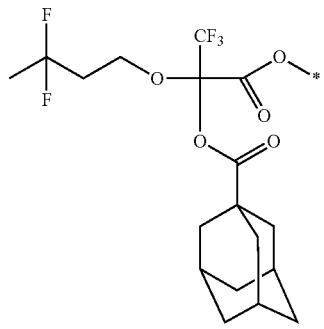

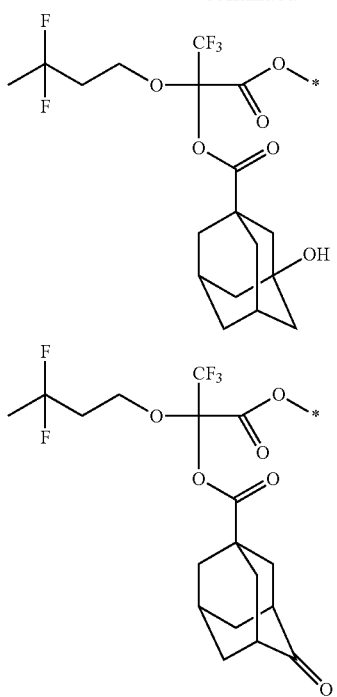
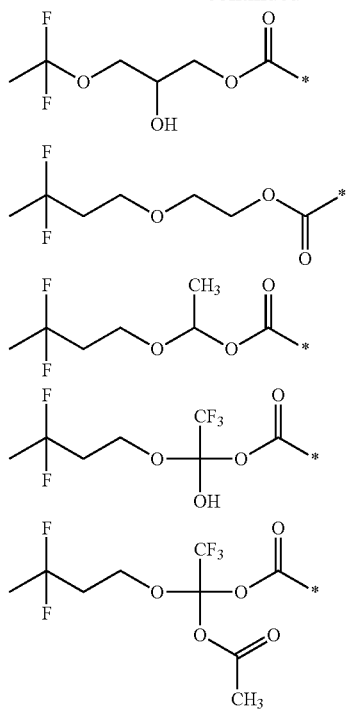
where * represents a binding site to Y.
Examples of the group represented by the formula (b1-11) include the following ones:
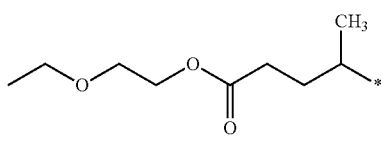
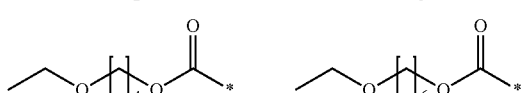
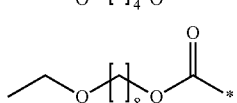
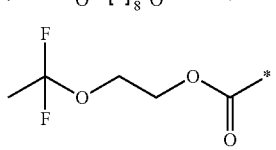
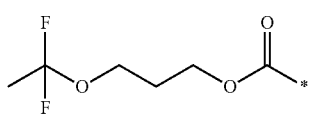
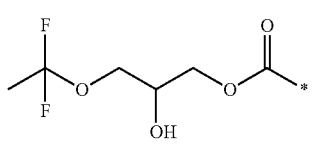
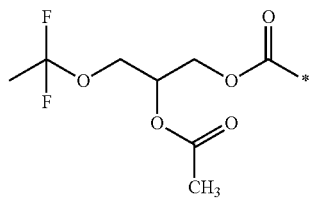
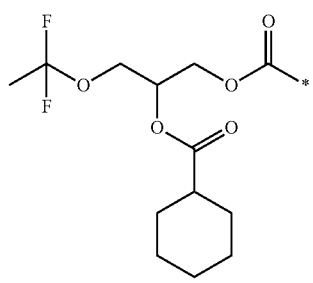
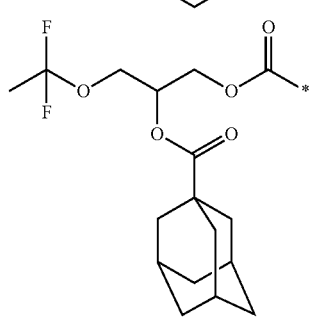

-continued

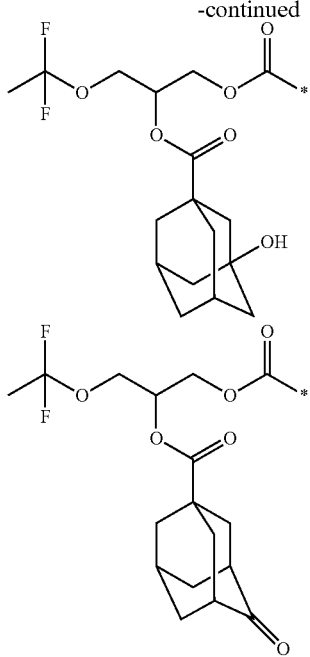

where * represents a binding site to Y.

Examples of the alicyclic hydrocarbon group represented by Y include those represented by formulae (Y1) to (Y11) Examples of the alicyclic hydrocarbon group represented by Y, in which a methylene group can be replaced by an oxygen atom, a sulfonyl group or a carbonyl group, include those represented by formulae (Y12) to (Y27).

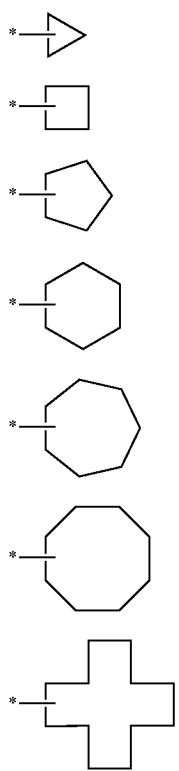

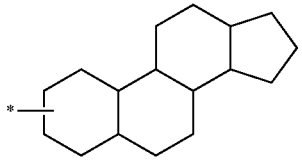 (Y8)

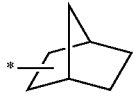 (Y9)

 (Y10)

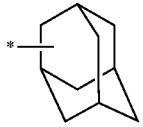 (Y11)

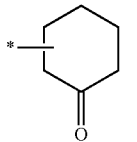 (Y12)

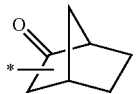 (Y13)

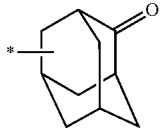 (Y14)

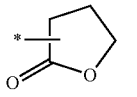 (Y15)

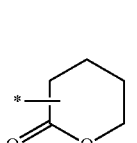 (Y16)

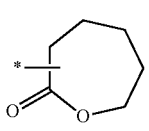 (Y17)

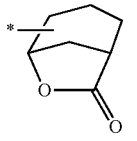 (Y18)

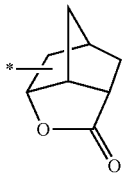 (Y19)

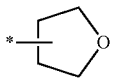 (Y20)

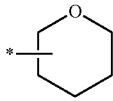 (Y21)

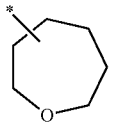 (Y22)

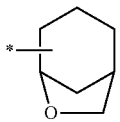 (Y23)

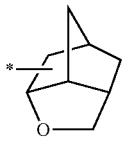 (Y24)

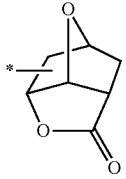 (Y25)

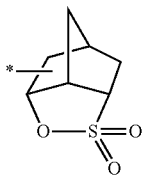 (Y26)

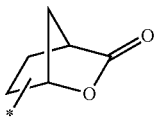 (Y27)

Among them, preferred are those represented by formulae (Y1) to (Y19), more preferred are those represented by formulae (Y11), (Y14), (Y15) and (Y19), and still more preferred are those represented by formulae (Y11) and (Y14).

Examples of the substituents for the alicyclic hydrocarbon group represented by Y include a halogen atom, a hydroxy group, an oxo group, a C1-C12 alkyl group, a C1-C12 hydroxy-containing alkyl group, a C3-C16 alicyclic hydrocarbon group, a C1-C12 alkoxy group, a C6-C18 aromatic hydrocarbon group optionally substituted with a C1-C4 alkyl group, a C7-C21 aralkyl group, a C2-C4 acyl group, a glycidyloxy group, or —$(CH_2)_{j2}$—O—CO—$R_{b1}$ group where $R_{b1}$ represents a C1-C16 alkyl group, a C3-C16 alicyclic hydrocarbon group, or a C6-C18 aromatic hydrocarbon group optionally substituted with a C1-C4 alkyl group. The symbol j2 represents an integer of 0 to 4.

Examples of the halogen atom include a fluorine atom, a chlorine atom, a bromine atom and an iodine atom.

Examples of the hydroxyl-containing methyl group include a hydroxymethyl group and a hydroxyethyl group.

Examples of alkoxy group include a methoxy group, an ethoxy group, a propoxy group, a butoxy group, a pentyloxy group, a hexyloxy group, a heptyloxy group, an octyloxy group, a decyloxy group and a dodecyloxy group.

Examples of an aromatic hydrocarbon group include aryl groups such as a phenyl group, a naphthyl group, a nantolyl group, a p-methylphenyl group, p-tert-butylphenyl group, p-adamantylphenyl group, a tolyl group, a xylyl group, a cumenyl group, a mesityl group, a biphenyl group, a phenanthryl group, a 2,6-diethylphenyl group, 2-methyl-6-ethylphenyl group.

Examples of an aralkyl group include a benzyl group, a phenethyl group, a phenylpropyl group, a naphthylmethyl group and a naphthylethyl group.

Examples of an acyl group include an acetyl group, a propionyl group and a butyryl group.

Examples of the group represented by Y include the following ones.

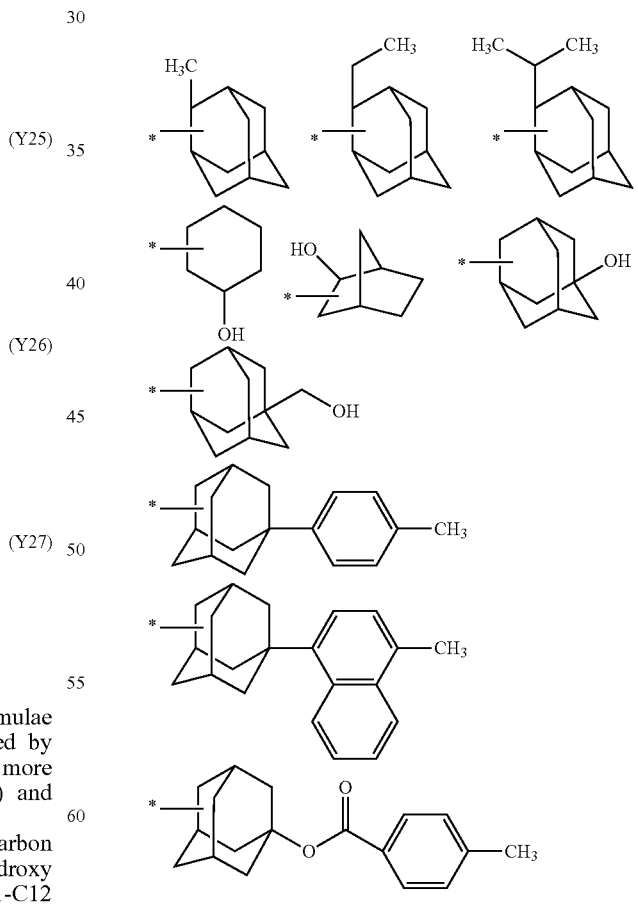

Y is preferably a C3-C18 alicyclic hydrocarbon group which can have a substituent, more preferably an adamantyl group which can have a substituent such as oxo group or a hydroxyl group, more preferably an adamantyl group, a hydroxyadamantyl group, or an oxoadamantyl group.

Examples of the sulfonic acid anion of the salt represented by formula (B1) include an anion represented by formulae (B1-A-1) to (B1-A-31), and more preferably an anions represented by formula (B1-A-1) to formula (B1-A-4), formula (B1-A-9), formula (B1-A-10), formula (B1-A-24) to formula (B1-A-29).

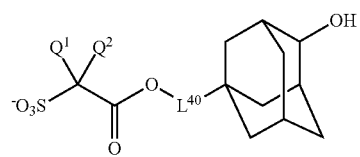
(I-A-1)

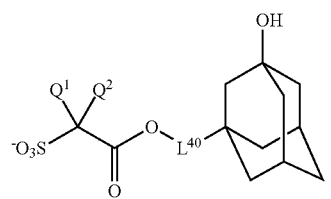
(I-A-2)

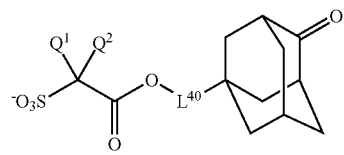
(I-A-3)

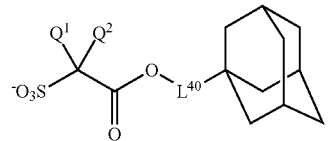
(I-A-4)

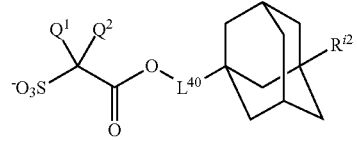
(I-A-5)

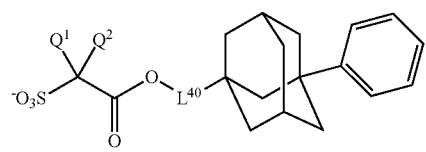
(I-A-6)

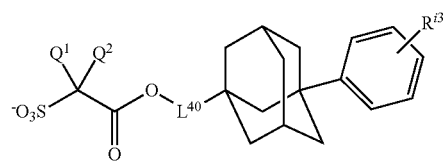
(I-A-7)

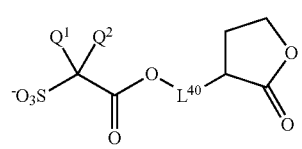
(I-A-8)

-continued

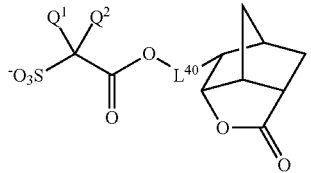
(I-A-9)

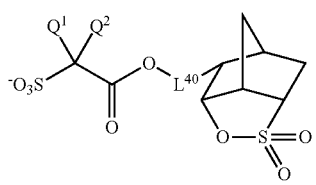
(I-A-10)

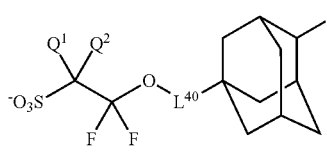
(I-A-11)

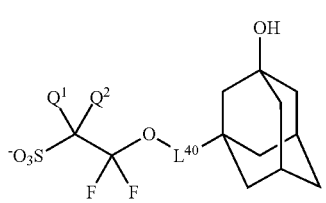
(I-A-12)

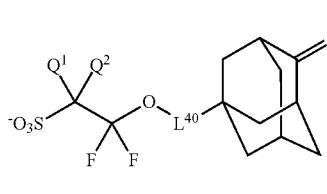
(I-A-13)

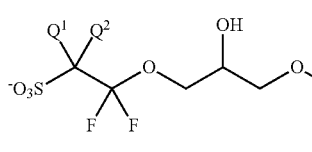
(I-A-14)

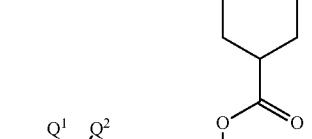
(I-A-15)

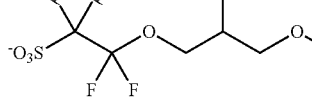

(I-A-16)

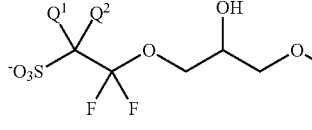

(I-A-17) 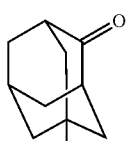 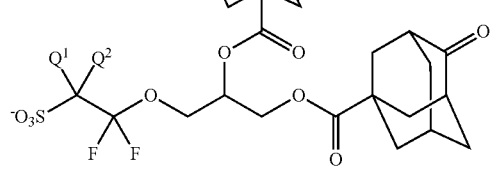
(I-A-18) 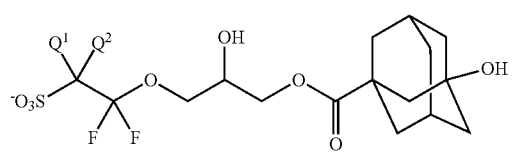
(I-A-19) 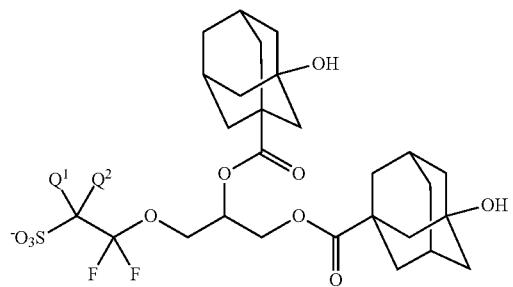
(I-A-20) 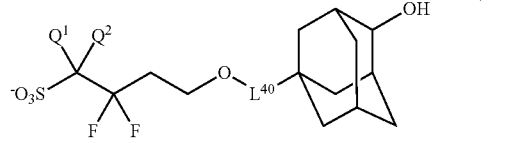
(I-A-21) 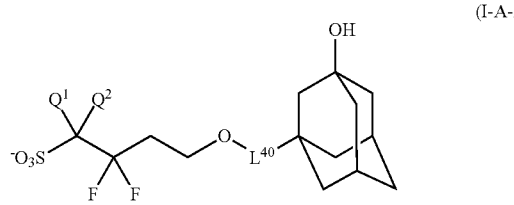
(I-A-22) 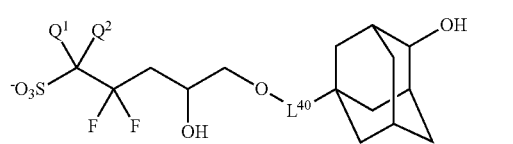
(I-A-23) 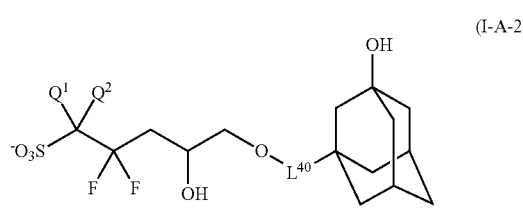
(I-A-24) 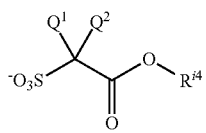
(I-A-25) 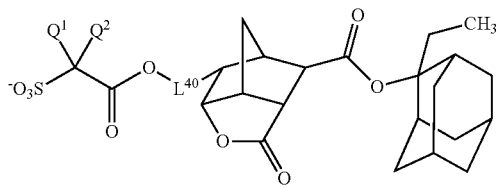
(I-A-26) 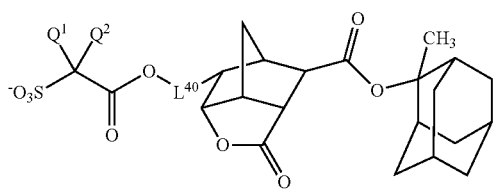
(I-A-27) 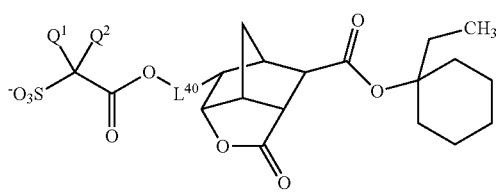
(I-A-28) 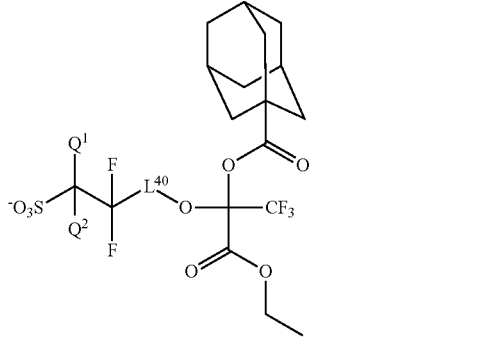
(I-A-29) 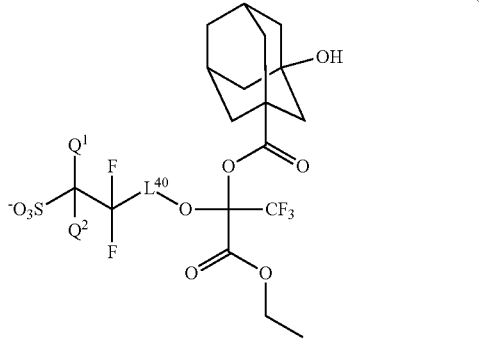

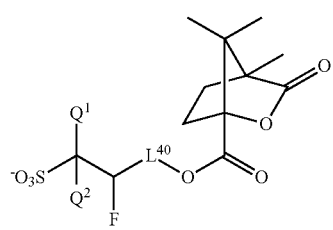
(I-A-30)

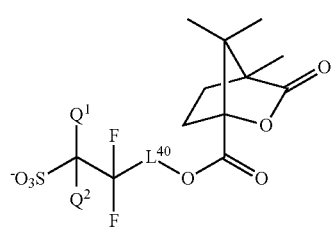
(I-A-31)

In formula (B1-A-1) to formula (B1-A-31), $R^{i2}$ to $R^{i4}$ each independently represent a C1 to C4 alkyl group, and preferably a methyl group.

$L^{40}$ represents a single bond or a C1 to C4 alkanediyl group. $Q^1$ and $Q^2$ represent the same meaning as defined above.

Among these, preferred examples of the sulfonic acid anion for the salt represented by the formula (B1) include anions represented by formulae (Ia-1) to (Ia-11), more preferably anions represented by formulae (Ia-1) to (Ia-3) and (Ia-7) to (Ia-11).

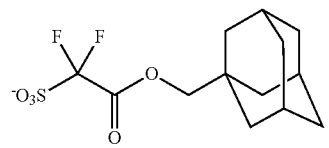
(Ia-1)

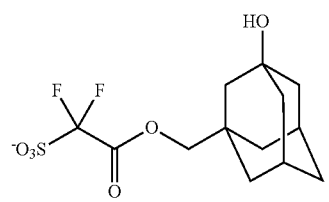
(Ia-2)

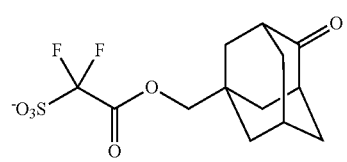
(Ia-3)

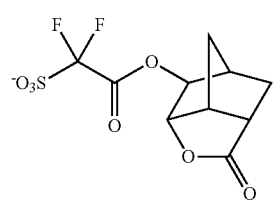
(Ia-4)

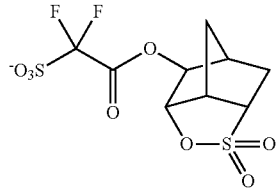
(Ia-5)

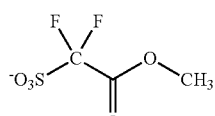
(Ia-6)

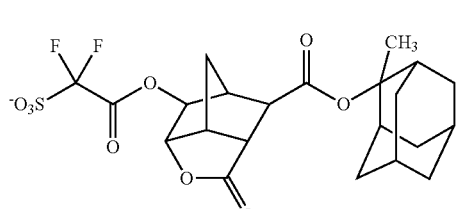
(Ia-7)

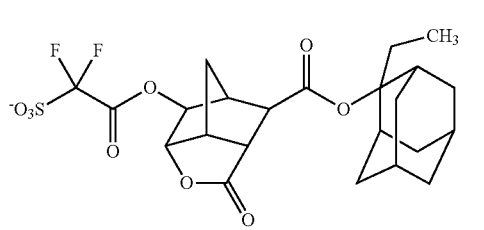
(Ia-8)

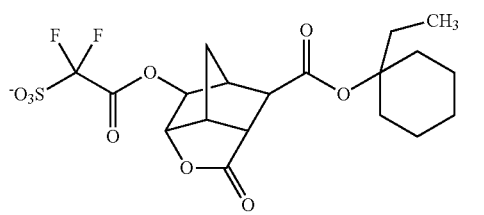
(Ia-9)

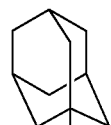
(Ia-10)

(Ia-11)

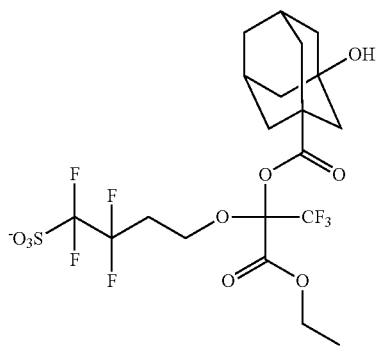

Examples of the sulfonylimide anion represented by A⁻ include the following ones.

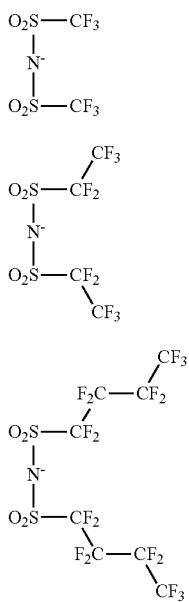

(I-b-1)
(I-b-2)
(I-b-3)
(I-b-4)
(I-b-5)

In formula (II-2), RA⁻ represents an organic group having an anion.

Examples of RA⁻ include organic groups having a sulfonic acid anion, a sulfonylimide anion, a sulfonylmethide anion or a carboxylic acid anion.

The divalent connecting group represented by $A^{II2}$ is preferably a C1 to C24 hydrocarbon group which may have a substituent. In the hydrocarbon group, preferably a hydrogen atom can be replaced by a fluorine atom or a C1 to C6 perfluoroalkyl group. In the hydrocarbon group, preferably a carbon atom can be replaced by an oxygen atom, a carbonyl group or a sulfonyl group.

The organic group represented by RA⁻ has preferably a sulfonic acid anion.

Preferably, the groups represented by formulae (II-1) and (II-2) are bonded directly to a vinyl group, an acryl group, a methacryl group, or an alkanoyl group.

The structural unit having the group represented by formula (II-1) is preferably one represented by formula (II-1-1):

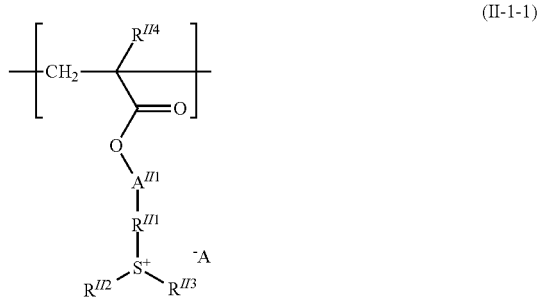

(II-1-1)

in which $R^{II1}$, $R^{II2}$, $R^{II3}$, $A^{II1}$ and A⁻ are as defined above; $R^{II4}$ represents a hydrogen atom, a halogen atom, or a C1 to C6 alkyl group which may have a halogen atom.

In formula (II-1-1), $A^{II1}$ represents preferably a single bond, a C1 to C30 linear or branched chain aliphatic hydrocarbon group, a C3 to C30 alicyclic hydrocarbon group, a C6 to C36 aromatic hydrocarbon group, any combination of them. In these hydrocarbon groups, a methyl group can be replaced by an oxygen atom, a sulfur atom, a carbonyl group or a sulfonyl group. $A^{II1}$ represents more preferably a single bond, a C1 to C12 linear or branched chain aliphatic hydrocarbon group, or a C3 to C24 alicyclic hydrocarbon group, still more preferably a single bond, a C1 to C8 linear or branched chain aliphatic hydrocarbon group, or a C3 to C12 alicyclic hydrocarbon group. In these hydrocarbon groups, a methyl group can be replaced by an oxygen atom, a sulfur atom, a carbonyl group or a sulfonyl group.

$R^{II4}$ represents preferably a hydrogen atom or a C1 to C4 alkyl group, and more preferably a hydrogen atom or a methyl group.

In the structural unit represented by formula (II-1-1), examples of its cation include the following ones.

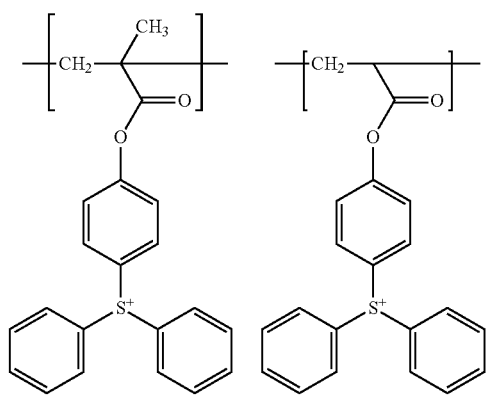

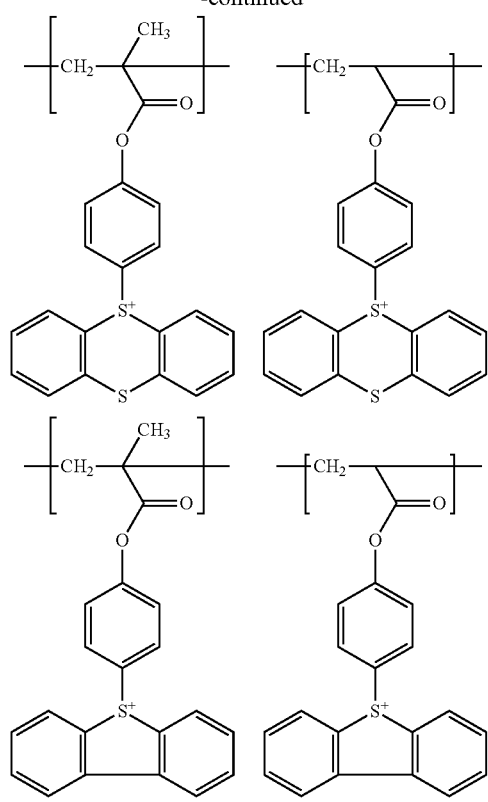
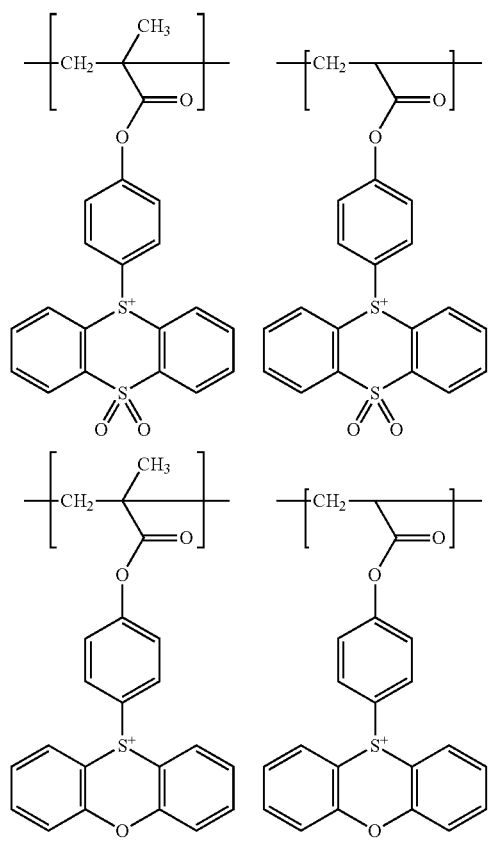
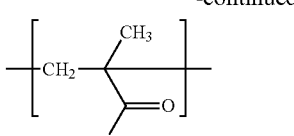
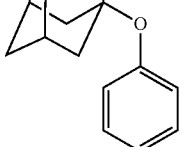
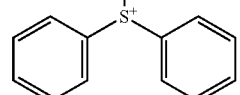
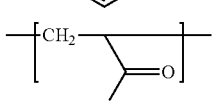
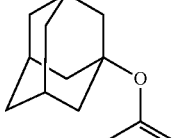
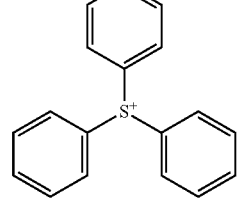
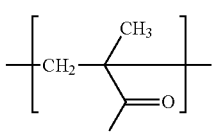
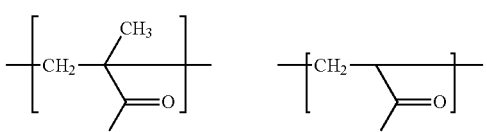
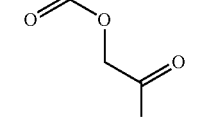
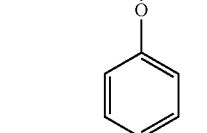
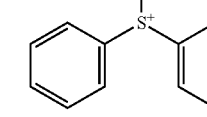

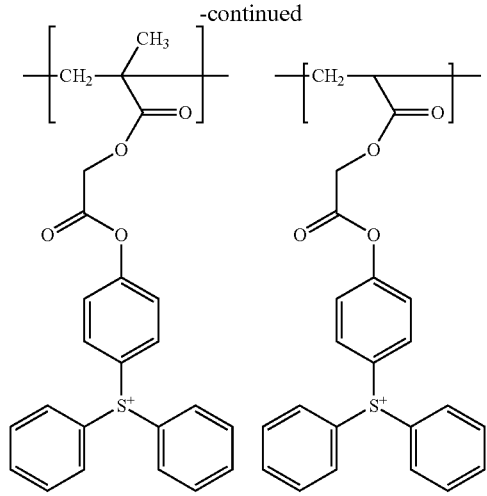
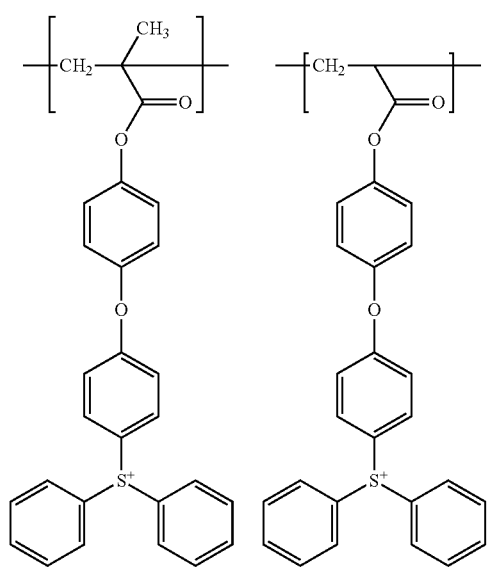
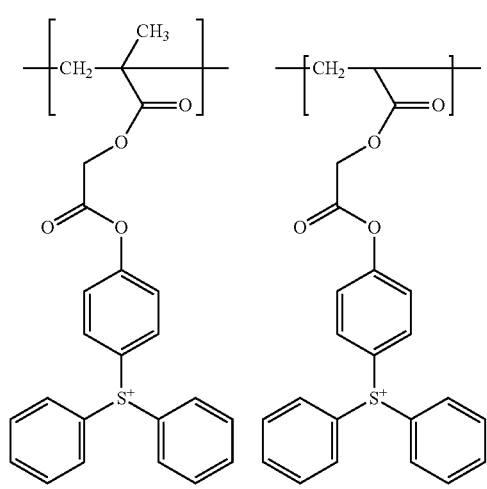
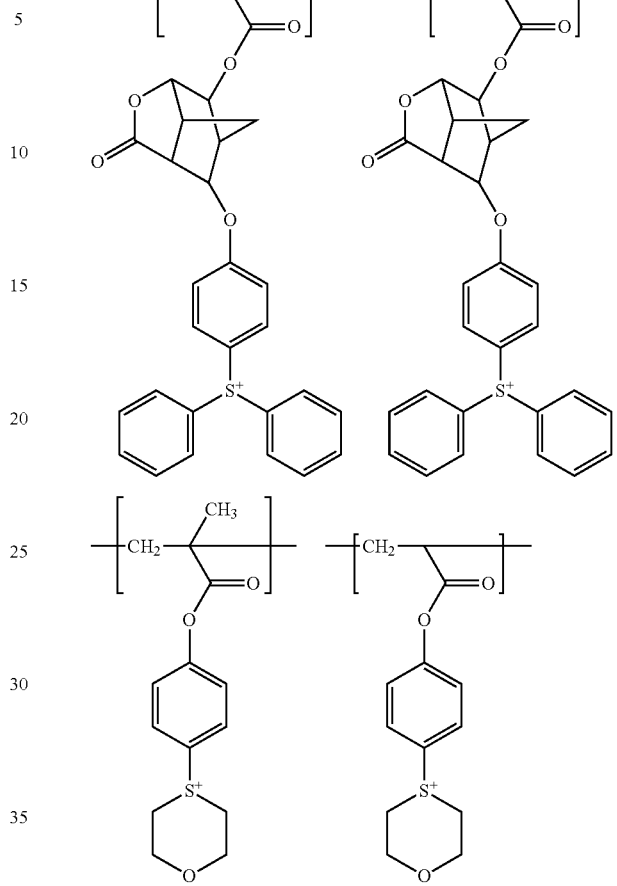
Examples of the structural unit represented by formula (II-1-1) include the following ones.
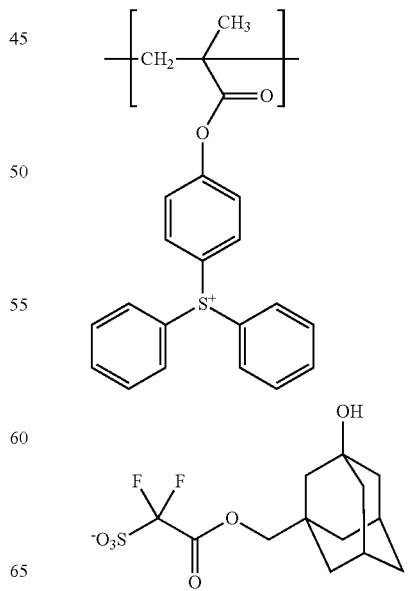

87
-continued
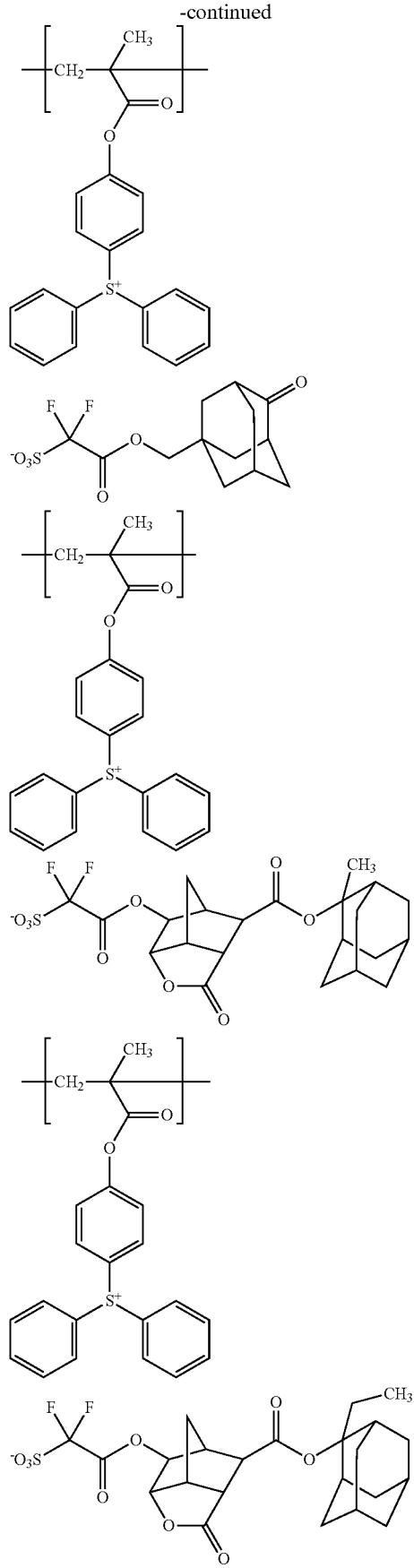
88
-continued
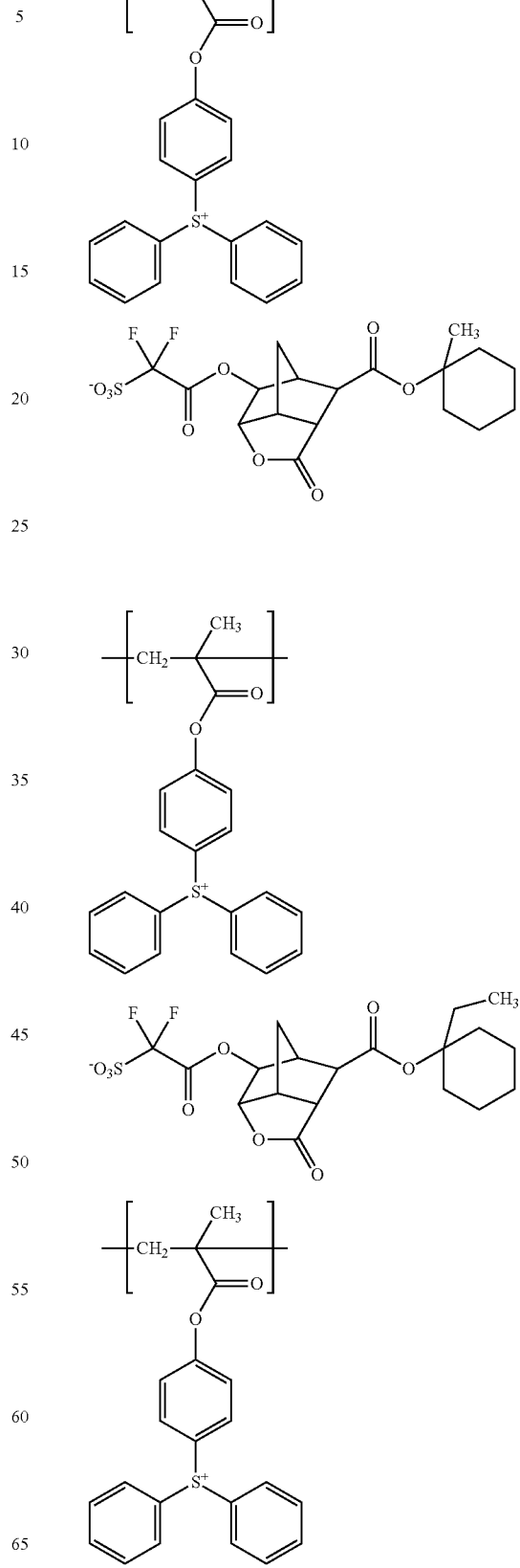

-continued

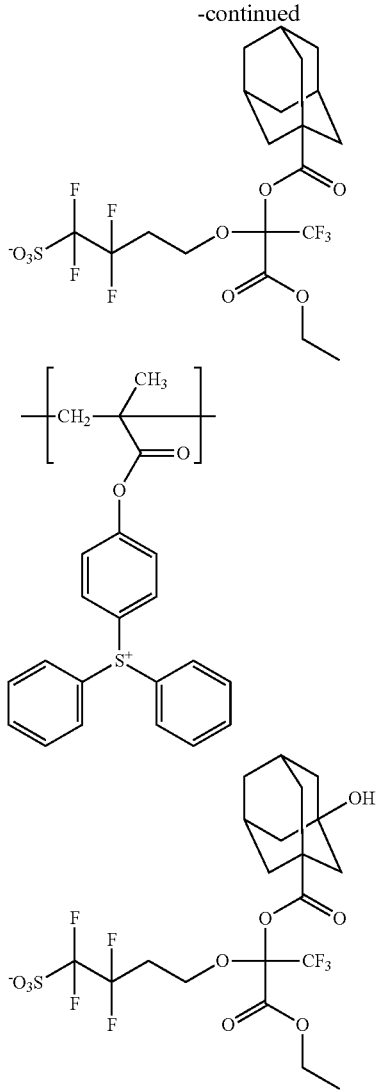

The structural unit having the group represented by formula (II-2) is preferably one represented by formula (II-2-AT):

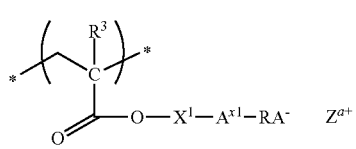

in which
$X^1$ represents a C1 to C17 straight or branched divalent saturated hydrocarbon group in which a carbon atom can be replaced by a carbonyl group, an oxygen atom or a sulfur atom and in which a hydrogen atom can be replaced by a halogen atom, a hydroxy group, or a C1 to C6 alkyl group optionally having a halogen atom;
$R^3$ represents a halogen atom or a C1 to C6 alkyl group optionally having a halogen atom;
$A^{x1}$ represents a C1 to C8 straight or branched alkanediyl group in which a hydrogen atom can be replaced by a fluorine atom or a C1-C6 perfluoroalkyl group;

$RA^-$ represents an organic group having an anion; and
$Z^{a+}$ represents an organic cation.

The structural unit having the group represented by formula (II-2-A') is preferably one represented by formula (II-2-A):

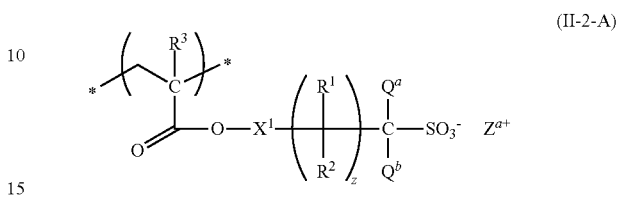

in which $R^3$, $X^1$ and $Z^{a+}$ are as defined above;
$Q^a$ and $Q^b$ each independently represent a fluorine atom or a C1 to C6 perfluoroalkyl group;
$R^1$ and $R^2$ each independently represent a hydrogen atom, a fluorine atom or a C1 to C6 perfluoroalkyl group; and
Z represents an integer of 0 to 6.

Examples of the perfluoroalkyl group represented by $Q^a$, $Q^b$, $R^1$ and $R^2$ include a trifluoromethyl group, a perfluoroethyl group, a perfluoro(n-propyl) group, a perfluoro(iso-propyl) group, a perfluoro(n-butyl) group, a perfluoro(sec-butyl) group, a perfluoro(tert-butyl) group, a perfluoropentyl group and a perfluorohexyl group.

Examples of the halogen atoms for $R^3$ include a fluorine atom, a chlorine atom, a bromine atom, and an iodine atom.

Examples of the alkyl group include a methyl group, an ethyl group, an n-propyl group, an iso-propyl group, an n-butyl group, a sec-butyl group, a tert-butyl group, n-pentyl group, and n-hexyl group. For $R^3$, examples of the alkyl group which may have halogen atom include a trifluoromethyl group, a pentafluoroethyl group, a perfluorobutyl group, a 1,1,1-trifluoroethyl group, and a 2,2-difluoroethyl group.

Examples of the divalent saturated hydrocarbon group represented by $X^1$ include linear alkanediyl groups, branched chain alkanediyl groups, a monocyclic divalent alicyclic hydrocarbon group, a polycyclic divalent alicyclic hydrocarbon group and combinations of them.

Specific examples of them include
linear alkanediyl groups such as a methylene group, an ethylene group, a propane-1,3-diyl group, a butane-1,4-diyl group, a pentane-1, 5-diyl group, a hexane-1, 6-diyl group, a heptane-1, 7-diyl group, an octane-1,8-diyl group, a nonane-1,9-diyl group, a decane-1,10-diyl group, a undecane-1,11-diyl group, a dodecane-1,12-diyl group;
branched chain alkanediyl groups such as a butane-1,3-diyl group, a2-methylpropane-1, 3-diyl group, a2-methylpropane-1, 2-diyl group, a pentane-1,4-diyl group, a 2-methyl butane-1,4-diyl group; a monocyclic divalent alicyclic hydrocarbon group such as a cyclobutan-1,3-diyl group, cyclopentane-1,3-diyl group, a cyclohexane-1,4-diyl group, and a cyclooctane-1,5-diyl group; and a polycyclic divalent alicyclic hydrocarbon group such as a norbornane-1,4-diyl group, a norbornane-2,5-diyl group, an adamantane-1,5-diyl group and an adamantane-2,6-diyl group.

Examples of the groups in which a carbon atom of the saturated hydrocarbon group has been replaced by a carbonyl group, an oxygen atom or a sulfur atom include the following divalent group represented by formulae (X1) to (X53)
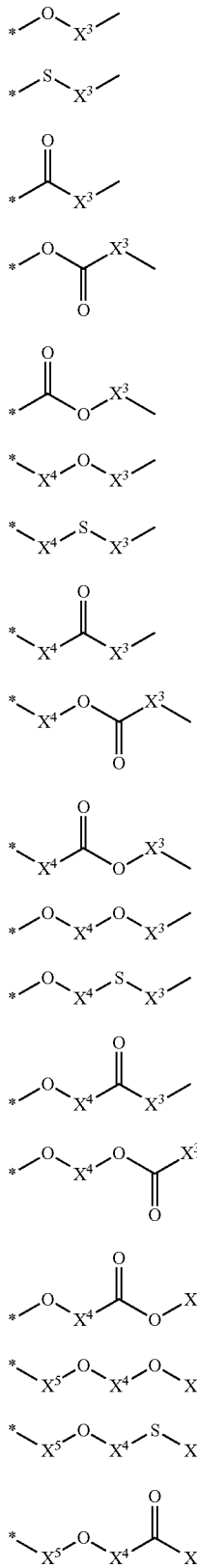
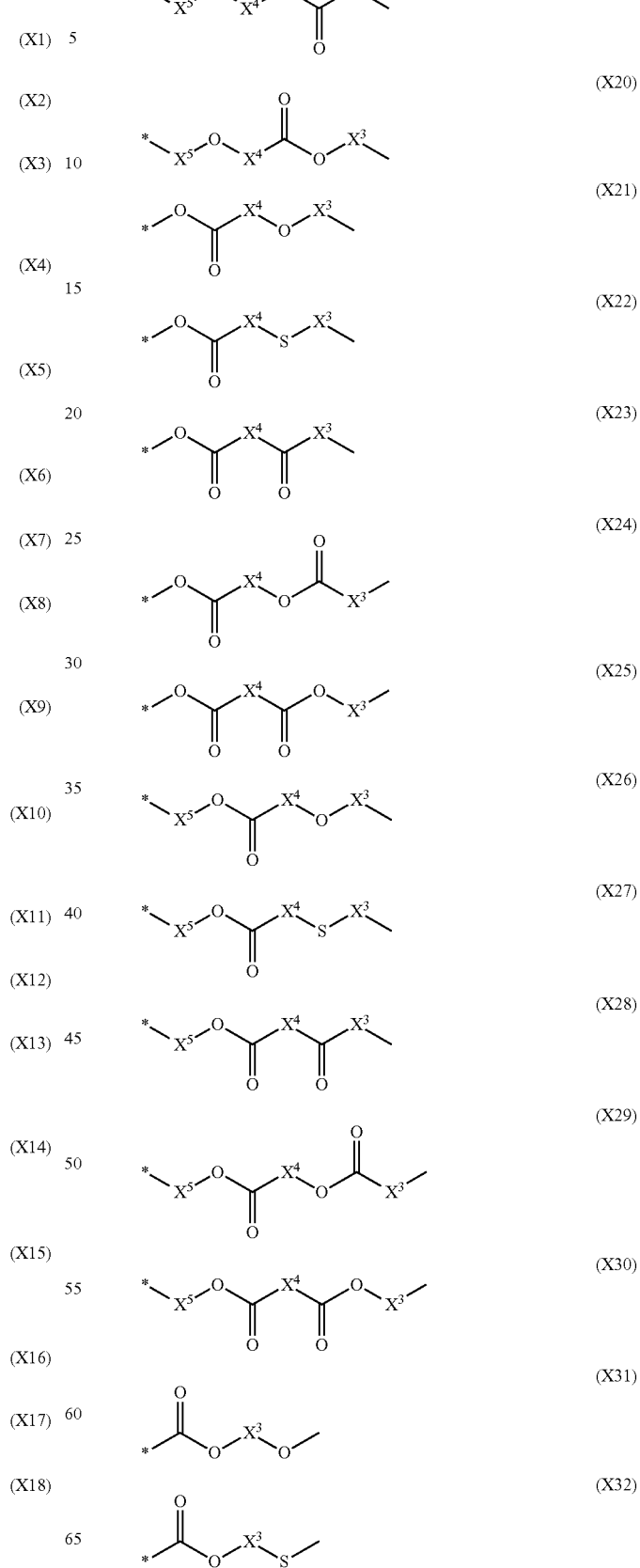

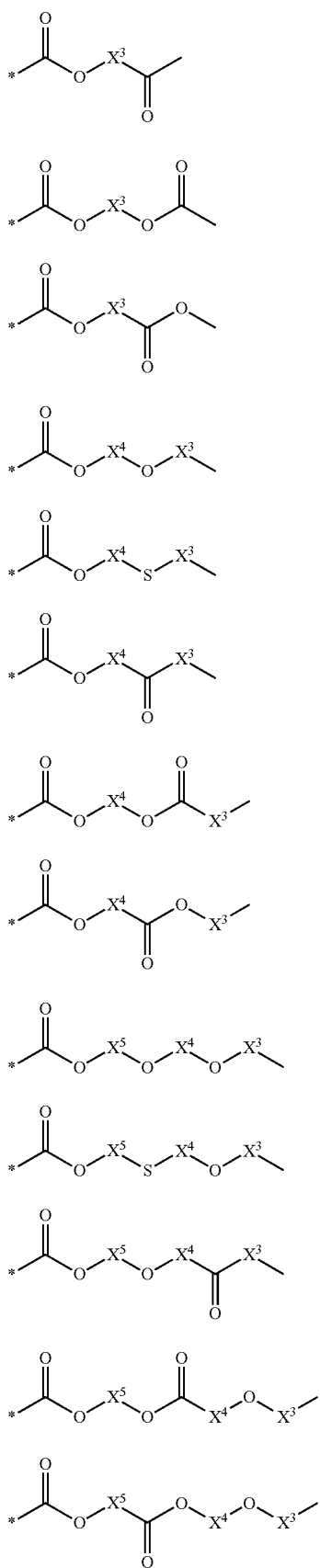

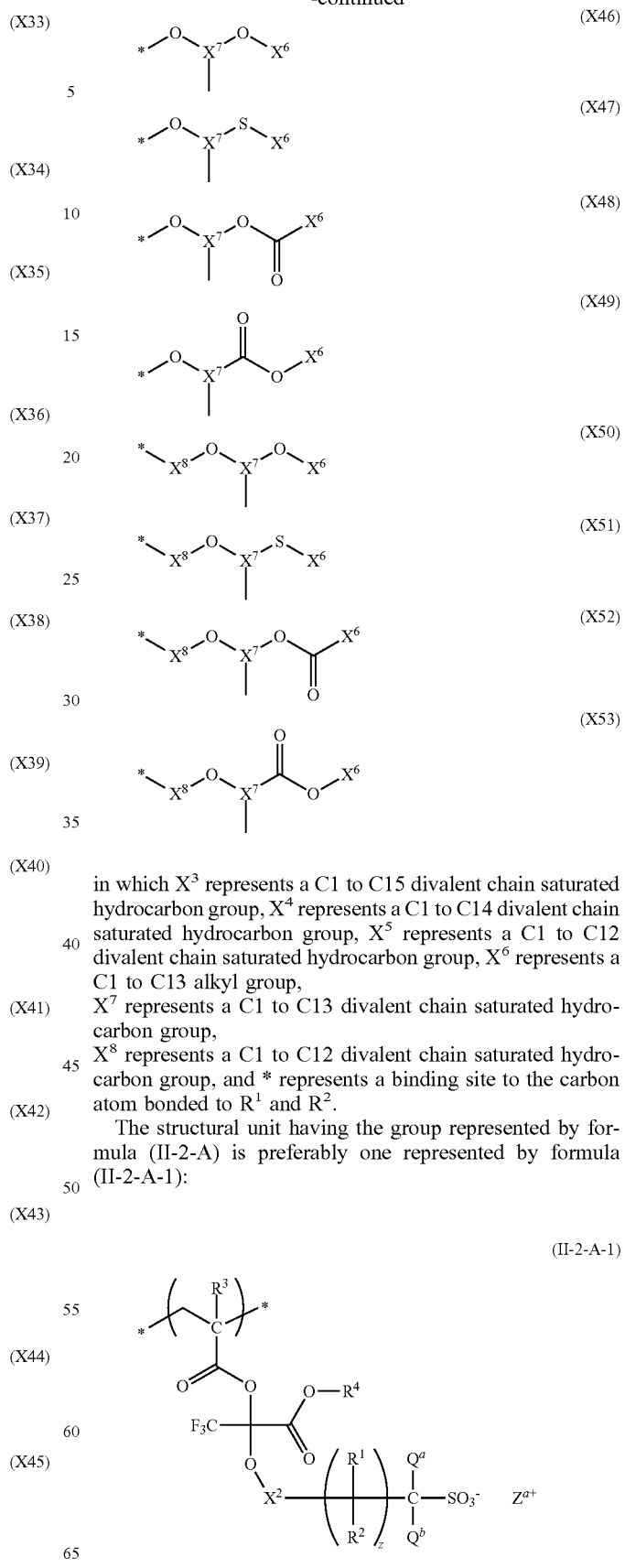

in which $X^3$ represents a C1 to C15 divalent chain saturated hydrocarbon group, $X^4$ represents a C1 to C14 divalent chain saturated hydrocarbon group, $X^5$ represents a C1 to C12 divalent chain saturated hydrocarbon group, $X^6$ represents a C1 to C13 alkyl group, $X^7$ represents a C1 to C13 divalent chain saturated hydrocarbon group, $X^8$ represents a C1 to C12 divalent chain saturated hydrocarbon group, and * represents a binding site to the carbon atom bonded to $R^1$ and $R^2$.

The structural unit having the group represented by formula (II-2-A) is preferably one represented by formula (II-2-A-1):

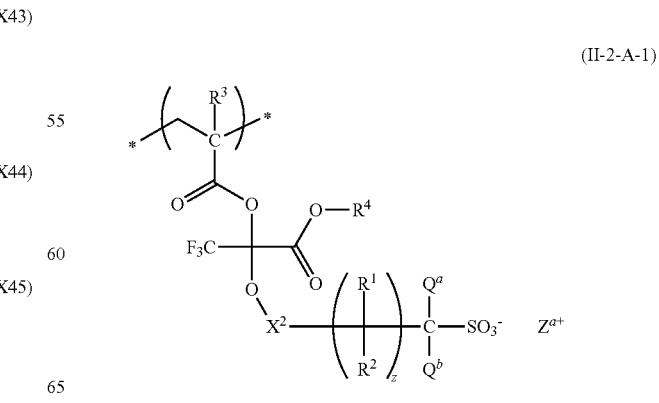

in which $R^1$, $R^2$, $R^3$, $Q^a$, $Q^b$, z and $Z^{a+}$ are as defined above;

$R^4$ represents a C1 to C12 linear or branched chain saturated hydrocarbon group; and $X^2$ represents a C1 to C12 linear or branched chain divalent saturated hydrocarbon group where a carbon atom can be replaced by a carbonyl group, an oxygen atom or a sulfur atom and in which a hydrogen atom can be replaced by a halogen atom or a hydroxy group;

$R^3$ represents a halogen atom or a C1-C6 alkyl group optionally having a halogen atom.

Examples of the saturated hydrocarbon group represented by $R^4$ include linear alkyl groups and branched chain alkyl groups.

Examples of the divalent saturated hydrocarbon group include linear alkanediyl groups and branched chain alkanediyl group.

As to $X^2$, examples of the groups in which a carbon atom of the saturated hydrocarbon group has been replaced by a carbonyl group, an oxygen atom or a sulfur atom include the divalent group represented by formulae (X1) to (X53).

The structural unit having the group represented by formula (II-2-A) is more preferably one represented by formula (II-2-A-2):

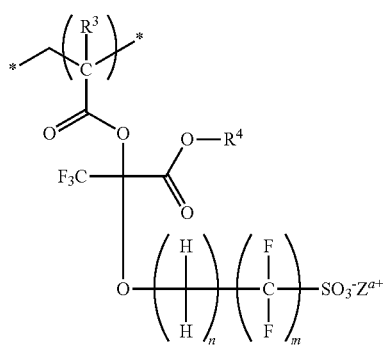

(II-2-A-2)

in which $R^3$, $R^4$ and $Z^{a+}$ are as defined above; and

"m" and "n" each independently represent 1 or 2.

Examples of the structural unit represented by formula (II-2-A-1) include the following ones and those recited in US2013/20993A1.

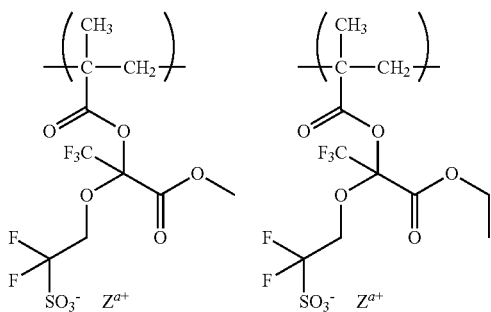

-continued

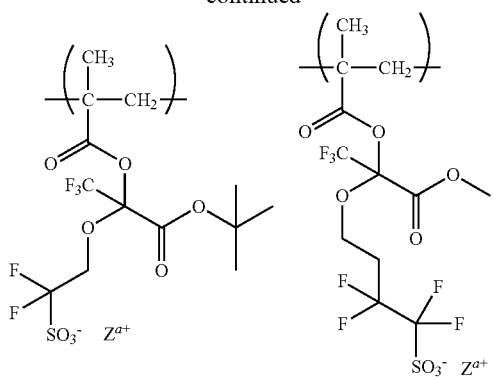

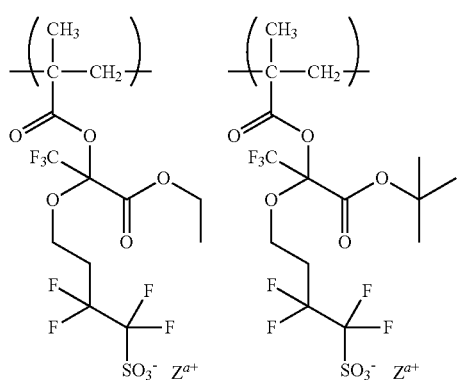

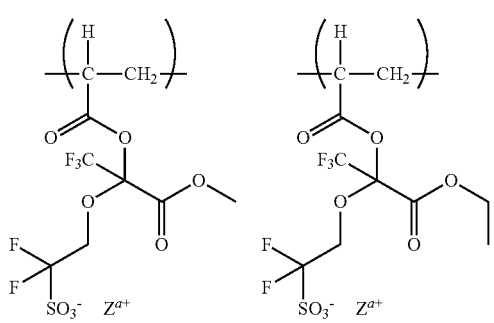

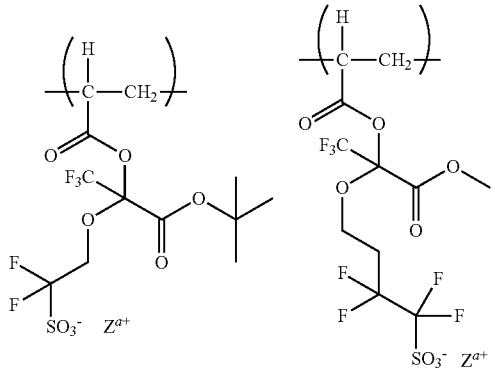

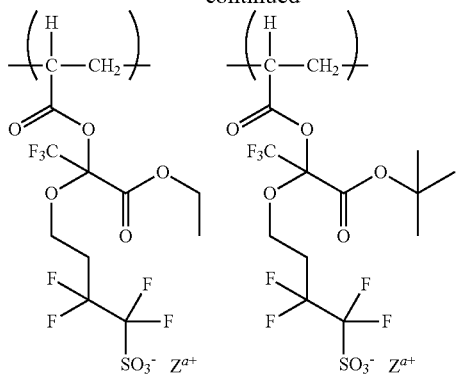

In each formula, $Z^{a+}$ is as defined above.

Examples of the structural unit represented by formula (II-2-A-2) include the following ones.

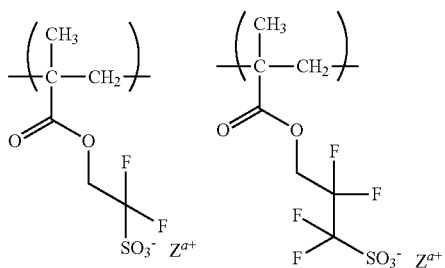

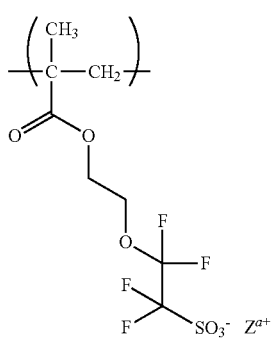

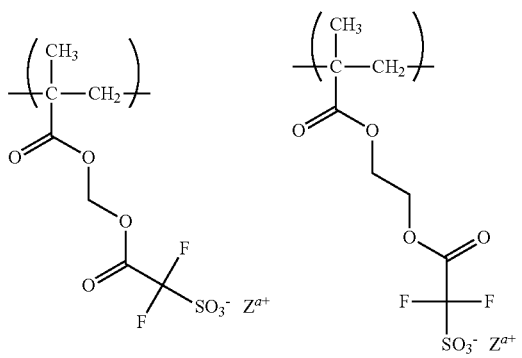

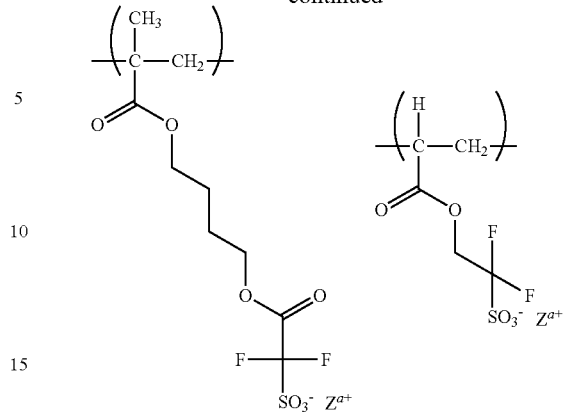

In each formula, $Z^{a+}$ is as defined above.

In the group represented by formula (II-2-A') and the other formulae having a group of formula (11-2), $Z^{a+}$ represents an organic cation. Examples of the organic cation include an organic onium cation such as an organic sulfonium cation, an organic iodonium cation, an organic ammonium cation, a benzothiazolium cation and an organic phosphonium cation. As $Z^+$, an organic sulfonium cation and an organic iodonium cation are preferred, and an arylsulfonium cation is more preferred. Herein, the arylsulfonium includes those having one, two or three aryl groups.

Preferable examples of the organic cation include the organic cations represented by the formulae (b2-1) to (b2-4)

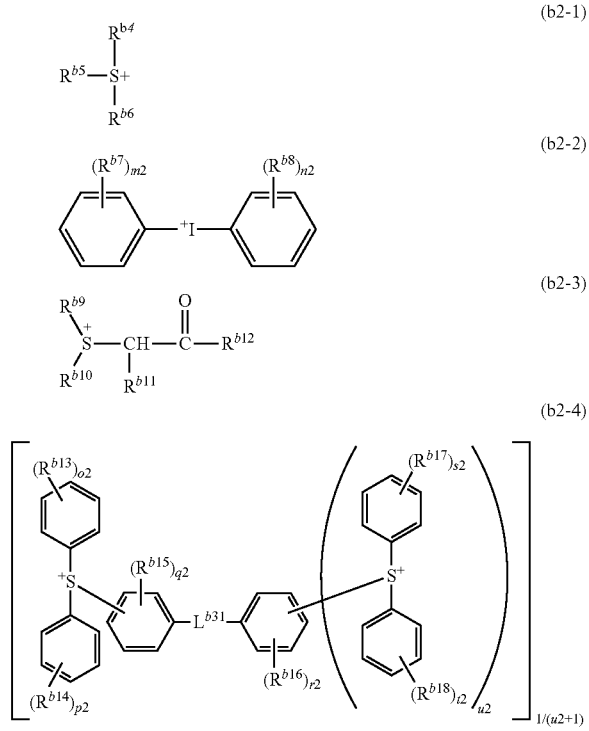

wherein $R^{b4}$, $R^{b5}$ and $R^{b6}$ independently represent a C1-C30 aliphatic hydrocarbon group in which a hydrogen atom can be replaced by a hydroxy group, a C1-C12 alkoxy group or a C6-C18 alicyclic hydrocarbon group, a C3-C36 alicyclic hydrocarbon group in which a hydrogen atom can be replaced by a halogen atom, a C2-C4 acyl group or a glycidyloxy group, or a C6-C36 aromatic hydrocarbon group in which a hydrogen atom can be replaced by a halogen atom, a hydroxy group, or C1-C12 alkoxy group; and $R^{b4}$ and $R^{b5}$, $R^{b4}$ and $R^{b6}$, or $R^{b5}$ and $R^{b6}$ can be bonded each other to form a ring containing S';

$R^{b7}$ and $R^{b8}$ are independently in each occurrence a hydroxy group, a C1-C12 alkyl group or a C1-C12 alkoxy group;

m2 and n2 independently represents an integer of 0 to 5;

$R^{b9}$ and $R^{b10}$ independently represent a C1-C36 aliphatic hydrocarbon group or a C3-C36 alicyclic hydrocarbon group, or $R^{b9}$ and $R^{b10}$ are bonded each other to form a ring together with the adjacent —S$^+$—, and one or more —CH$_2$— in the ring can be replaced by an oxygen atom, sulfur atom or carbonyl group; and $R^{b11}$ represents a hydrogen atom, a C1-C36 aliphatic hydrocarbon group, a C3-C36 alicyclic hydrocarbon group, or a C6-C18 aromatic hydrocarbon group, and $R^{b12}$ represents a C1-C12 aliphatic hydrocarbon group where a hydrogen atom can be replaced by a C6-C18 aromatic hydrocarbon group, a C3-C18 alicyclic hydrocarbon group, and a C6-C18 aromatic hydrocarbon group optionally substituted with C1-C12 alkoxy group or C1-C12 alkylcarbonyloxy group; or $R^{b11}$ and $R^{b12}$ are bonded each other to form a C1-C10 divalent alicyclic hydrocarbon group which forms a 2-oxo-cycloalkyl group together with the adjacent —CHCO—, and one or more —CH$_2$— in the group can be replaced by an oxygen atom, sulfur atom or carbonyl group; and $R^{b13}$, $R^{b14}$, $R^{b15}$, $R^{b16}$, $R^{b17}$ and $R^{b18}$ independently represent a hydroxy group, a C1-C12 alkyl group or a C1-C12 alkoxy group;

$L^{b31}$ represents —S— or —O—; and o2, p2, s2 and t2 each independently represents an integer of 0 to 5;

q2 and r2 each independently represents an integer of 0 to 4; and u2 represents 0 or 1.

Examples of the aliphatic hydrocarbon group represented by each substituent include an alkyl group such as a methyl group, an ethyl group, a propyl group, an isopropyl group, a butyl group, a sec-butyl group, a tert-butyl group, a pentyl group, a hexyl group, an octyl group, and a 2-ethylhexyl group. The aliphatic hydrocarbon group represented by $R^{b9}$ to $R^{b12}$ is preferably a C1-C18 alkyl group, more preferably a C1-C12 alkyl group.

Examples of the alkyl group where a hydrogen atom has been replaced by an alicyclic hydrocarbon group include 1-(adamantane-1-yl) alkane-1-yl group.

The alicyclic hydrocarbon group represented by each substituent may be any of a monocyclic one and a polycyclic one, a hydrogen atom of which can be replaced by an alkyl group. When a hydrogen atom of it has been replaced by an alkyl group, the total number of carbon atoms is 30 or less.

Examples of the monocyclic alicyclic hydrocarbon group include a cycloalkyl group such as a cyclopropyl group, a cyclobutyl group, a cyclopentyl group, a cyclohexyl group, a cycloheptyl group, a cyclodecyl group.

Examples of the polycyclic alicyclic hydrocarbon group include a decahydronaphtyl group, an adamantyl group, a norbornyl group, and the following ones.

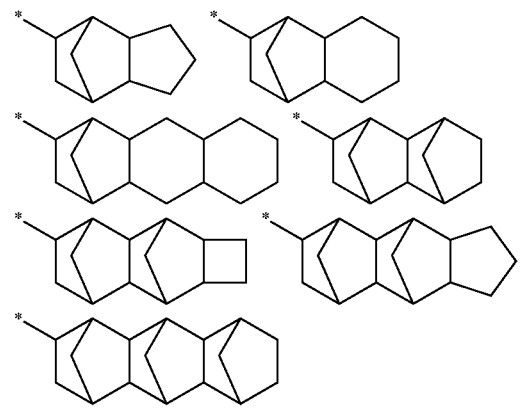

The alicyclic hydrocarbon group represented by $R^{b9}$ to $R^{b12}$ has preferably 3 to 18, more preferably 4 to 12, carbon atoms. Examples of the alicyclic hydrocarbon group where a hydrogen atom has been replaced by an alkyl group include a methylcyclohexyl group, a 2-alkyladamantane-2-yl group, a methylnorbornyl group, and an isobornyl group.

Preferable examples of the aromatic hydrocarbon group include substituted or unsubstituted phenyl group such as a phenyl group, a tolyl group, a xylyl group, a cumenyl group, a mesityl group, a 4-ethylphenyl group, 4-tert-butylphenyl group, 4-cyclohexylphenyl group, a 4-adamantylphenyl group, a 2, 6-diethylphenyl group, a 2-methyl-6-ethylphenyl group; a biphenyl group, a naphtyl group, a phenanthryl group.

Preferred examples of the aromatic hydrocarbon group where a hydrogen atom has been replaced by an alkoxy group include 4-methoxyphenyl group.

Preferred examples of the alkyl group where a hydrogen atom has been replaced by an aromatic hydrocarbon group, i.e., an aralkyl group, include a benzyl group, a phenethyl group, a phenylpropyl group, a trityl group, a naphthylmethyl group and a naphthylethyl group.

When the aromatic hydrocarbon group has an alkyl group or an alicyclic hydrocarbon group as a substituent, the substituent is preferably a C1 to C12 alkyl group or a C3 to C18 alicyclic hydrocarbon group. Examples of the alkoxy group include a methoxy group, an ethoxy group, a propoxy group, a butoxy group, a pentyloxy group, a hexyloxy group, a heptyloxy group, an octyloxy group, a decyloxy group and a dodecyloxy group.

Examples of the C2-C4 acyl group include an acetyl group, a propyonyl group and a butyryl group.

Examples of the halogen atom include a fluorine atom, a chlorine atom, a bromine atom and an iodine atom.

Preferable examples of the alkylcarbonyloxy group include a methylcarbonyloxy group, an ethylcarbonyloxy group, n-propylcarbonyloxy group, an isopropylcarbonyloxy group, n-butylcarbonyloxy group, sec-butylcarbonyloxy group, a tert-butylcarbonyloxy group, a pentylcarbonyloxy group, a hexylcarbonyloxy group, an octylcarbonyloxy group and 2-ethyl hexylcarbonyloxy group.

The ring containing $S^+$ formed by bonding $R^{b4}$ and $R^{b5}$, $R^{b4}$ and $R^{b6}$, or $R^{b5}$ and $R^{b6}$ each other may be a monocyclic ring, a polycyclic ring, an aromatic ring, a non-aromatic ring, a saturated ring or a unsaturated ring. The ring can contain a sulfur atom or oxygen atom in addition to S. The ring preferably has 3 to 18 carbon atoms, and more preferably has 4 to 13 carbon atoms. Examples of such ring include, 3 to 12-membered rings, preferably 3 to 7-membered rings, specifically the following ones.

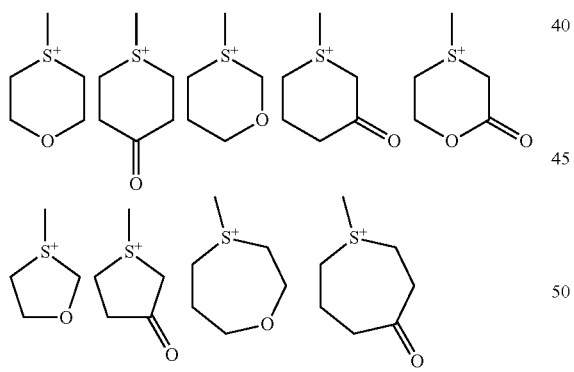

Examples of the ring group formed by bonding $R^{b9}$ and $R^{b10}$ together with the adjacent $S^+$ and the divalent alicyclic hydrocarbon group include, 3 to 12-membered rings, preferably 3 to 7-membered rings, specifically a thiolan-1-ium ring (tetrahydrothiphenium ring), a thian-1-ium ring and a 1,4-oxathian-4-ium ring.

Examples of the ring group formed by bonding $R^{b11}$ and $R^{b12}$ include 3 to 12-membered rings, preferably 3 to 7-membered rings, specifically oxocyclopentane ring, oxocyclohexane ring, oxonorbornane ring and oxoadamantane ring.

Among the above-mentioned cations, preferred is the cation represented by the formula (b2-1).

Examples of the cation represented by the formula (b2-1) include the following ones.

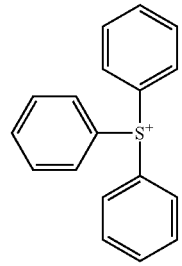

(b2-c-1)

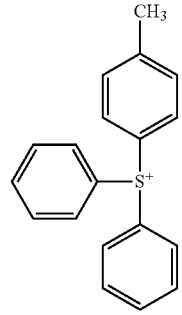

(b2-c-2)

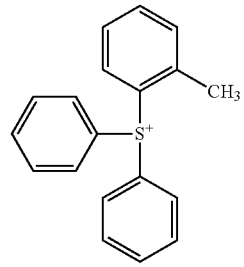

(b2-c-3)

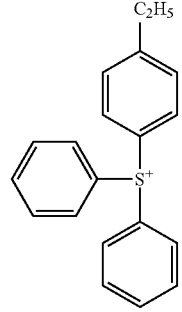

(b2-c-4)

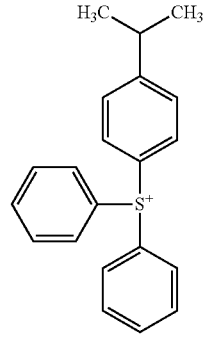

(b2-c-5)

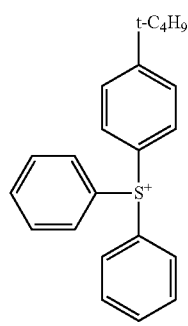 (b2-c-6)
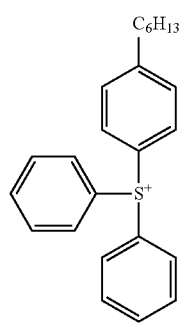 (b2-c-7)
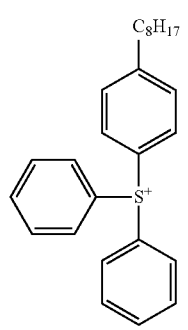 (b2-c-8)
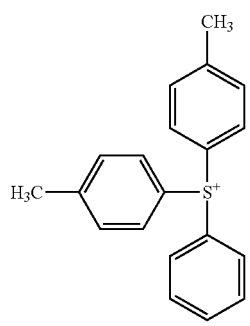 (b2-c-9)
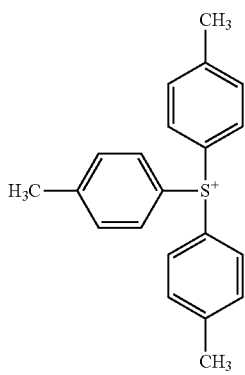 (b2-c-10)
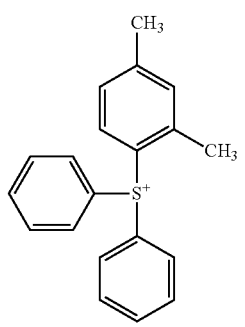 (b2-c-11)
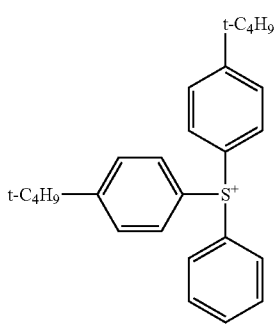 (b2-c-12)
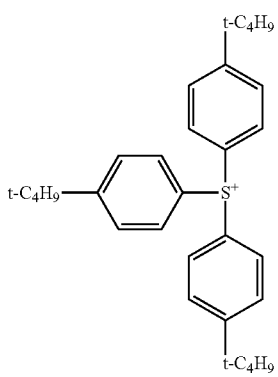 (b2-c-13)
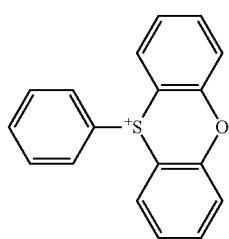 (b2-c-14)

105
-continued
(b2-c-15)
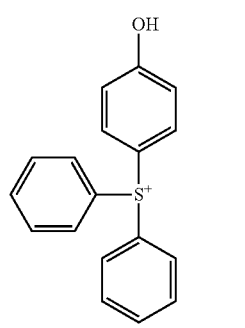
(b2-c-16)
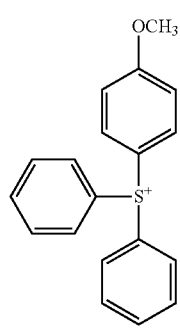
(b2-c-17)
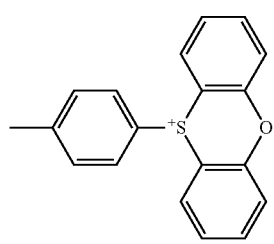
(b2-c-18)
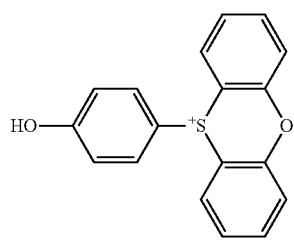
(b2-c-19)
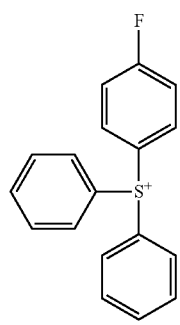
106
-continued
(b2-c-20)
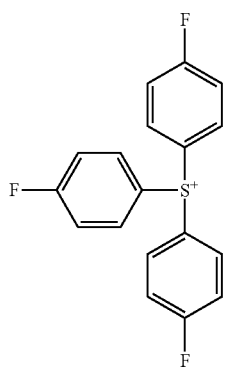
(b2-c-21)
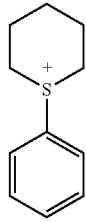
(b2-c-22)
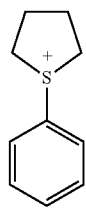
(b2-c-23)
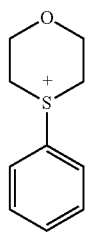
(b2-c-24)
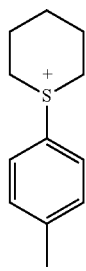
(b2-c-25)
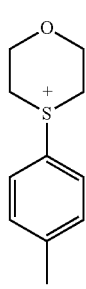

-continued
(b2-c-26)
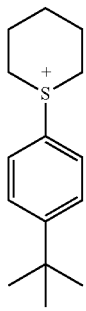
(b2-c-27)
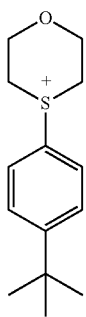
Examples of the cation represented by the formula (b2-2) include the following ones.
(b2-c-28)
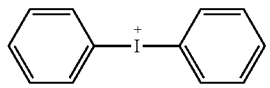
(b2-c-29)
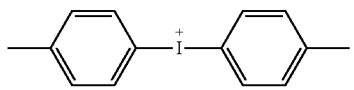
(b2-c-30)
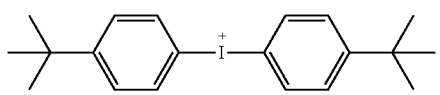
Examples of the cation represented by the formula (b2-3) include the following ones.
(b2-c-31)
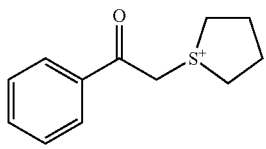
(b2-c-32)
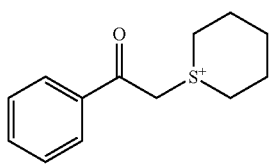
-continued
(b2-c-33)
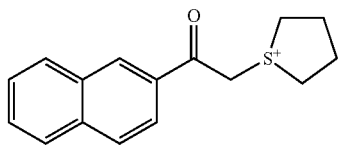
(b2-c-34)
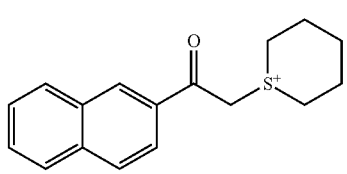
Examples of the cation represented by the formula (b2-4) include the following ones.
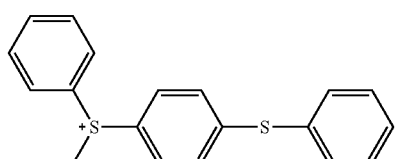
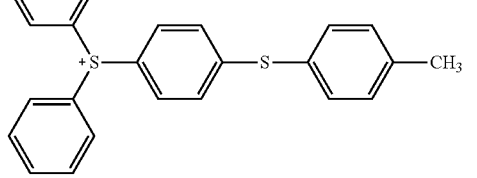
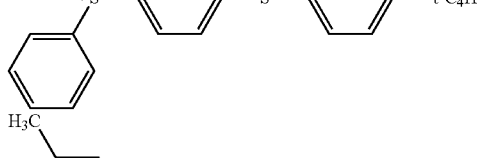
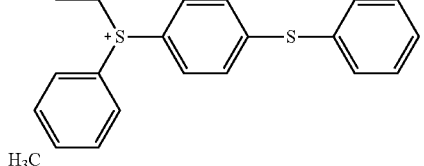
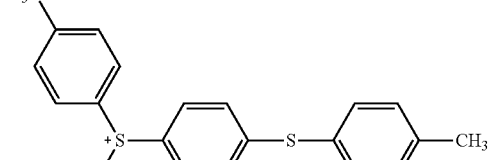

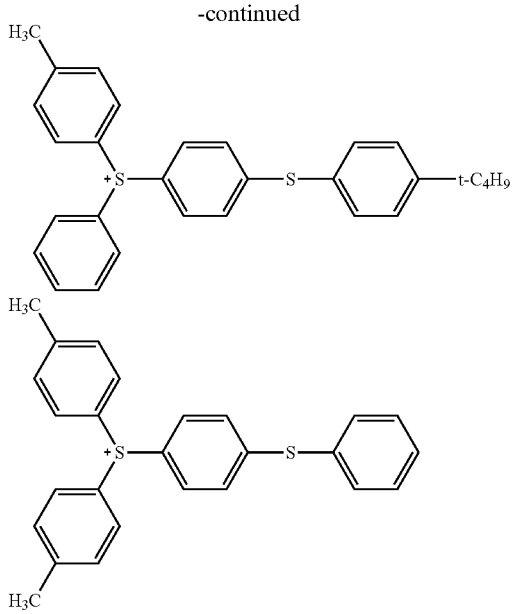
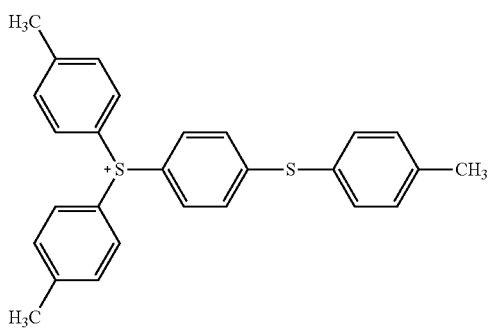
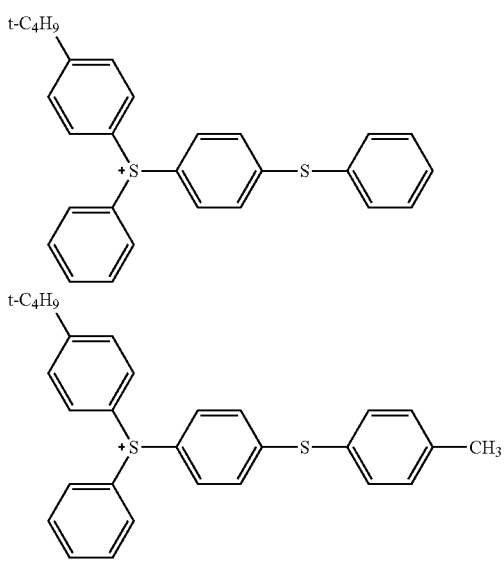
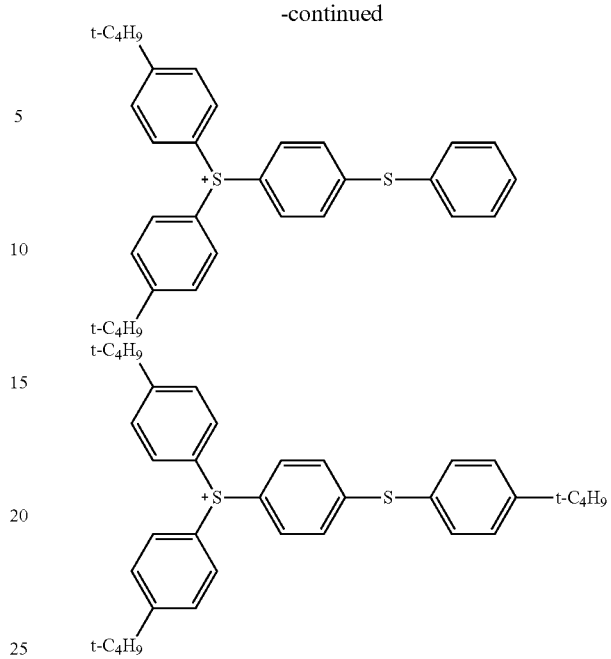

When the resin (A) further has the structural unit (11), the content thereof is preferably 1 to 20% by mole, more preferably 2 to 15% by mole, and still more preferably 3 to 10% by mole, based on all the structural units of the resin.

The structural unit (s) is derived from a monomer having no acid-labile group.

As to a monomer having no acid-labile group, monomers which have been known to in the art can be used as such monomer, and they are not limited to any specific one provided that it has no acid-labile group.

The structural unit having no acid-labile group preferably has a hydroxyl group or a lactone ring. When the resin (A) has the structural unit derived from the monomer having no acid-labile group and having a hydroxyl group or a lactone ring, a photoresist composition capable of providing a photoresist film with good resolution and adhesiveness of photoresist to a substrate can be obtained.

Hereinafter, the structural unit having no acid-labile group and having a hydroxy group is referred to as "structural unit (a2)", and the structural unit having no acid-labile group and having a lactone ring is referred to as "structural unit (a3)".

The resin (A) which further has the structural unit (a2) or (a3) can provide a photoresist composition with improved resolution of the pattern and improved adhesiveness to a substrate The hydroxy group which the structural unit (a2) has may be an alcoholic hydroxy group or a phenolic hydroxy group.

Resin (A) may have one or more of the structural units (a2).

Examples of the structural unit (a2) having a phenolic hydroxy group include one represented by the formula (a2-A).

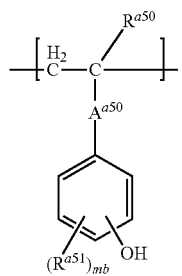

(a2-A)

In formula (a2-A), $R^{a50}$ represents a hydrogen atom, a halogen atom, a C1 to C6 alkyl group or a C1 to C6 halogenated alkyl group; $R^{a51}$ is independently in each occurrence a halogen atom, a hydroxyl group, a C1 to C6 alkyl group, a C1 to C6 alkoxy group, a C2 to C4 acyl group, a C2 to C4 acyloxy group, an acryloyl group or a methacryloyl group;
$A^{a50}$ represents a single bond or *—$X^{a51}$-($A^{a52}$-$X^{a52}$)$_{na}$—, where * represents a binding site to the carbon atom bonded to $R^{a50}$; $A^{a52}$ represents a C1 to C6 alkanediyl group, $X^{a51}$ and $X^{a52}$ each independently represent —O—, —CO—O— or —O—CO— and "na" represents 0 or 1; and
"mb" represents an integer of 0 to 4.

The structural unit represented by the formula (a2-A) is sometimes referred to as "structural unit (a2-A)".

In the formula (a2-A), examples of the halogen atom include a fluorine atom, a chlorine atom, a bromine atom or iodine atom.

Examples of the C1 to C6 alkyl group include a methyl group, an ethyl group, a propyl group, an isopropyl group, a butyl group, an isobutyl group, a sec-butyl group, a tert-butyl group, a pentyl group and a hexyl group.

Examples of the C1 to C6 halogenated alkyl group include a trifluoromethyl group, a pentafluoroethyl group, a heptafluoropropyl group, a heptafluoroisopropyl group, a nonafluorobutyl group, a nonafluoro-sec-butyl group, a nonafluoro-tert-butyl group, a perfluoropentyl group and a perfluorohexyl group.

$R^{a50}$ is preferably a hydrogen atom or a C1 to C4 alkyl group, more preferably a C1 to C2 alkyl group.

Examples of the C1 to C6 alkoxy group include a methoxy group, an ethoxy group, a propoxy group, an isopropoxy group, a butoxy group, an isobutoxy group, a sec-butoxy group, a tert-butoxy group, a pentyloxy group and a hexyloxy group, and a C1 to C4 alkoxy group is preferred and a C1 to C2 alkoxy group is more preferred and a methoxy group is especially preferred.

Examples of the C2 to C4 acyl group include an acetyl group, a propyonyl group and a butyryl group, and examples of the C2 to C4 acyloxy group include an acetyloxy group, a propyonyloxy group and a butyryloxy group.

$R^{a50}$ is preferably a C1 to C6 alkyl group, more preferably a methyl group.

Examples of *—$X^{a51}$-($A^{a52}$-$X^{a52}$)$_{na}$— include *—O—, *—CO—O—, *—O—CO—, *—CO—O-$A^{a52}$-CO—O—, *—O—CO-$A^{a52}$-O— *—O-$A^{a52}$-CO—O— *—CO—O-$A^{a52}$-O—CO— and *—O—CO-$A^{a52}$-O—CO—, preferably *—CO—O—, *—CO—O-$A^{a52}$-CO—O— or *—O-$A^{a52}$-CO—O—.

$R^{a50}$ is preferably a C1 to C4 alkylanediyl group, more preferably a methylene group or an ethylene group.

$A^{a50}$ is preferably a single bond, *—CO—O—, *—O—, or *—CO—O— $A^{a52}$-CO—O—, more preferably a single bond, *—CO—O— or *—CO—O—CH$_2$—CO—O—, and still more preferably a single bond or *—CO—O—.

In the formula (a2-A), "mb" is preferably 0, 1 or 2, and is more preferably 0 or 1, and especially preferably 0.

In the formula (a2-A), a hydroxy group is presented at preferably o-positioned or p-positioned, more preferably p-positioned. Examples of the monomer from which the structural unit (a2-A) is derived include compounds mentioned in JP2010-204634A1 and JP2012-12577A1.

Examples of the structural unit represented by the formula (a2-A) include one represented by the formula (a2-0).

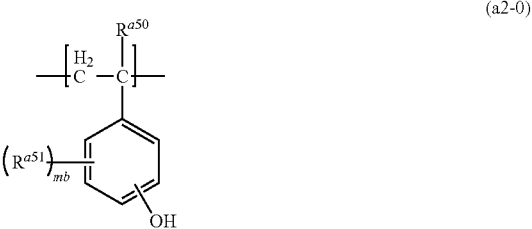

(a2-0)

In formula (a2-0), $R^{a50}$, $R^{a51}$ and "ma" are as defined above. Examples of the monomer from which the structural unit (a2-0) is derived include compounds mentioned in JP2010-204634A1. Among them, the structural units represented by formulae (a2-0-1), (a2-0-2), (a2-0-3) and (a2-0-4) are preferred as the structural unit represented by formula (a2-0), and those represented by formulae (a2-0-1) and (a2-0-2) are more preferred.

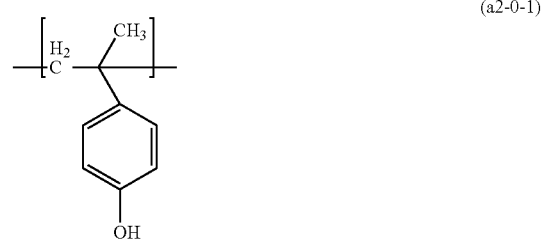

(a2-0-1)

(a2-0-2)

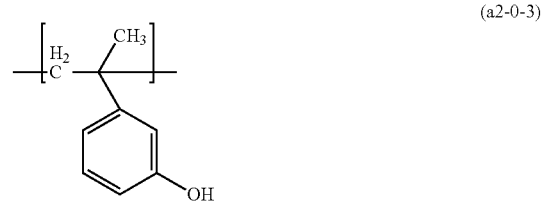

(a2-0-3)

-continued

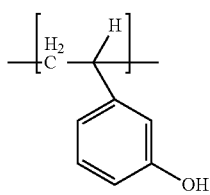
(a2-0-4)

Resin (A) which has a structural unit represented by formula (a2-0) can be produced, for example, by polymerizing a monomer where its phenolic hydroxyl group has been protected with a suitable protecting group, followed by deprotection. Examples of the protecting group for a phenolic hydroxyl group include an acetyl group.

When Resin (A) has the structural unit represented by formula (a2-A), its content is usually 5 to 80% by mole and preferably 10 to 70% by mole and more preferably 15 to 65% by mole based on all the structural units of the resin.

Examples of the structural unit (a2) having an alcoholic hydroxy group include one represented by the formula (a2-1):

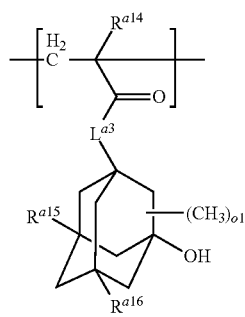
(a2-1)

wherein $R^{a14}$ represents a hydrogen atom or a methyl group, $R^{a15}$ and $R^{a16}$ each independently represent a hydrogen atom, a methyl group or a hydroxyl group, $L^{a3}$ represents *—O— or *—O—$(CH_2)_{k2}$—CO—O— in which * represents a binding site to —CO—, and k2 represents an integer of 1 to 7, and "o1" represents an integer of 0 to 10. Hereinafter, the structural unit represented by formula (a2-1) is referred to as "structural unit (a2-1)".

In the formula (a2-1), $R^{a14}$ is preferably a methyl group. $R^{a15}$ is preferably a hydrogen atom. $R^{a16}$ is preferably a hydrogen atom or a hydroxyl group. $L^{a3}$ is preferably *—O— or *—O—$(CH_2)_{f2}$—CO—O— in which * represents a binding site to —CO—, and "f2" represents an integer of 1 to 4, is more preferably *—O— and *—O—$CH_2$—CO—O—, and is still more preferably *—O—, and "o1" is preferably 0 to 3 and is more preferably 0 or 1.

Preferred examples of the structural unit represented by formula (a2-1) include those represented by formulae (a2-1-1) to (a2-1-6).

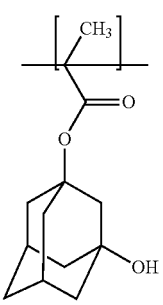
(a2-1-1)

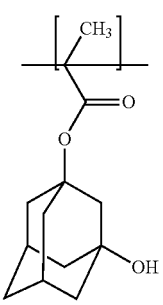
(a2-1-2)

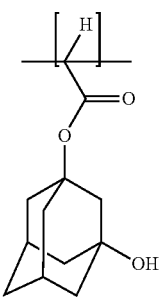
(a2-1-3)

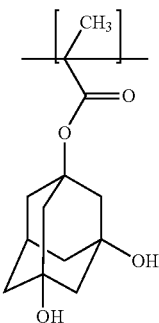
(a2-1-4)

(a2-1-5)
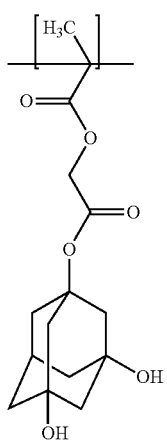

(a2-1-6)
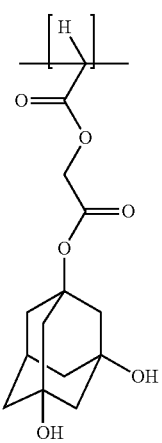

(a3-1)
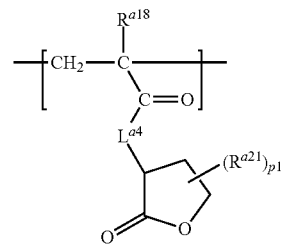

(a3-2)
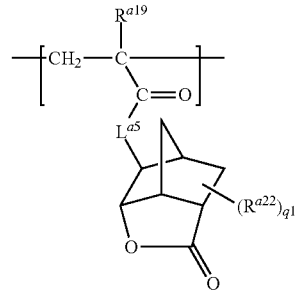

(a3-3)
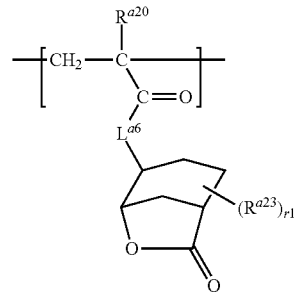

(a3-4)
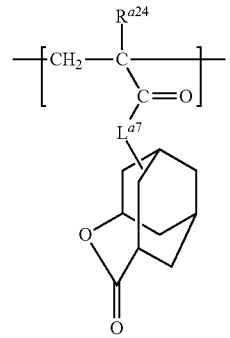

Among them, more preferred are those represented by formulae (a2-1-1), (a2-1-2), (a2-1-3) and (a2-1-4), still more preferred are those represented by formulae (a2-1-1) and (a2-1-3). Examples of monomers from which the structural unit represented by formula (a2-1) is derived include compounds mentioned in JP2010-204646A.

When Resin (A) further has the structural unit represented by formula (a2-1), its content is usually 1 to 45% by mole, preferably 1 to 40% by mole, and more preferably 1 to 35% by mole, and especially preferably 2 to 20% by mole, based on all the structural units of the resin.

Examples of the lactone ring contained in the structural unit (a3) include a monocyclic lactone ring such as β-propiolactone ring, γ-butyrolactone ring and γ-valerolactone ring, and a condensed ring formed from a monocyclic lactone ring and the other ring. Among them, preferred are γ-butyrolactone ring and a condensed lactone ring formed from γ-butyrolactone ring and the other ring.

Preferable examples of the structural unit (a3) include those represented by the formulae (a3-1), (a3-2), (a3-3) and (a3-4).

In formulae, $L^{a4}$, $L^{a5}$ and $L^{a6}$ each independently represent *—O— or *—O—$(CH_2)_{k3}$—CO—O— in which * represents a binding site to —CO— and k3 represents an integer of 1 to 7, $R^{a18}$, $R^{a19}$ and $R^{a20}$ each independently represent a hydrogen atom or a methyl group, $R^{a21}$ represents a C1-C4 aliphatic hydrocarbon group, $R^{a22}$ and $R^{a23}$ are independently in each occurrence a carboxyl group, a cyano group or a C1-C4 aliphatic hydrocarbon group, $R^{a24}$ each independently represent a hydrogen atom, a halogen atom, or a C1-C6 alkyl group which may have a halogen atom, $L^{a7}$ represents a single bond, $*^1$-$L^{a8}$-CO—O—, $*^1$-$L^{a8}$-CO—O—, $*^1$-$L^{a8}$-CO—O-$L^{a9}$-CO—O— or $*^1$-$L^{a8}$-CO—O-$L^{a9}$-O— in which $L^{a8}$ and $L^{a9}$ each independently represent C1-C6 alkanediyl group, $*^1$ represents a binding site to —CO—, and p1 represents an integer of 0 to 5, q1 and r1 independently each represent an integer of 0 to 3. Examples of halogen atom represented by $R^{a24}$ include a fluorine atom, a chlorine atom, a bromine atom and an iodine atom.

Examples of the alkyl group represented by $R^{a24}$ include a methyl group, an ethyl group, a propyl group, a butyl group, a pentyl group, and a hexyl group, preferably a C1-C4 alkyl group, and more preferably a methyl group and an ethyl group.

As to $R^{a24}$, examples of the alkyl group which has an halogen atom include a trifluoromethyl group, a pentafluoroethyl group, a heptafluoropropyl group, a heptafluoroisopropyl group, a nonafluorobutyl group, a nonafluoro-sec-butyl group, a nonafluoro-tert-butyl group, a perfluoropentyl group, a perfluorohexyl group, a trichloromethyl group, a tribromomethyl group, and a triiodomethyl group.

As to $L^{a5}$ and $L^{a9}$, examples of the alkanediyl group include a methylene group, an ethylene group, a propane-1,3-diyl group, abutane-1,4-diyl group, a pentane-1,5-diyl group and a hexane-1,6-diyl group, a butane-1,3-diyl group, 2-methylpropane-1,3-diyl group, a 2-methylpropane-1,2-diyl group, a pentane-1,4-diyl group and a 2-methylbutane-1,4-diyl group.

It is preferred that L", $L^{a5}$ and $L^{a6}$ each independently represent *—O— or *—O—$(CH_2)_n$—CO—O— in which * represents a binding site to —CO— and d1 represents an integer of 1 to 4, and it is more preferred that L", $L^{a5}$ and $L^{a6}$ are *—O— and *—O—$CH_2$—CO—O—, and it is still more preferred that $L^{a4}$, $L^{a5}$ and $L^{a6}$ are *—O—.

$R^{a18}$, $R^{a19}$ and $R^{a20}$ are preferably methyl groups. $R^{a21}$ is preferably a methyl group. It is preferred that $R^{a22}$ and $R^{a23}$ are independently in each occurrence a carboxyl group, a cyano group or a methyl group.

It is preferred that p1, q1 and r1 each independently represent an integer of 0 to 2, and it is more preferred that p1, q1 and r1 each independently represent 0 or 1.

$R^{a24}$ is preferably a hydrogen atom or a C1-C4 alkyl group, more preferably a hydrogen atom, a methyl group or an ethyl group, and still more preferably a hydrogen atom or a methyl group.

$L^{a7}$ represents preferably a single bond or *¹-$L^{a8}$-CO—O—, more preferably a single bond, *¹—$CH_2$—CO—O— or *¹—$C_2H_4$—CO—O—.

Examples of the monomer from which the structural unit (a3) is derived include those mentioned in JP2010-204646A, JP2000-122294A and JP2012-41274A. As the structural unit (a3), preferred are those represented by the formulae (a3-1-1) to (a3-1-4), the formulae (a3-2-1) to (a3-2-4), the formulae (a3-3-1) to (a3-3-4) and the formulae (a3-4-1) to (a3-4-12), more preferred are those represented by the formulae (a3-1-1), (a3-1-2), (a3-2-3), (a3-2-4) and (a3-4-1) to (a3-4-12), still more preferred are those represented by the formulae (a3-4-1) to (a3-4-12), and further still more preferred are those represented by the formulae (a3-4-1) to (a3-4-6).

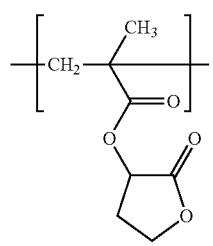
(a3-1-1)

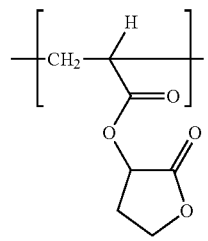
(a3-1-2)

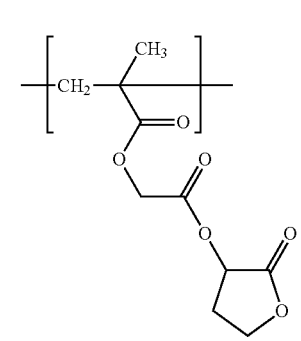
(a3-1-3)

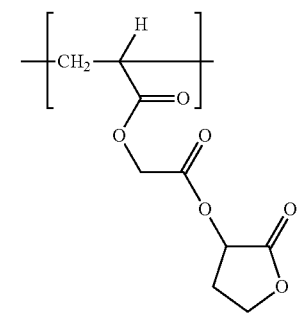
(a3-1-4)

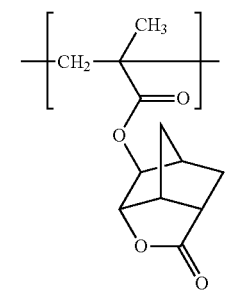
(a3-2-1)

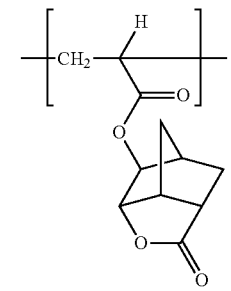
(a3-2-2)

(a3-2-3)
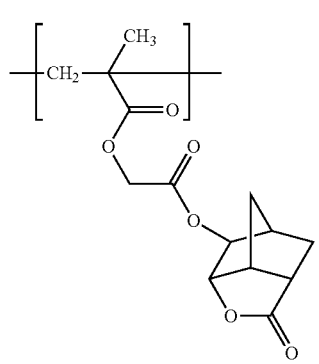
(a3-2-4)
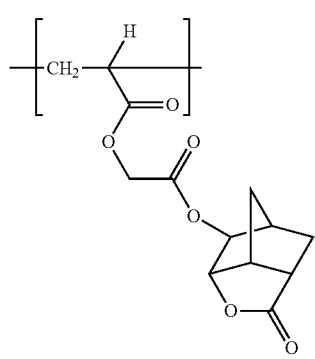
(a3-3-1)
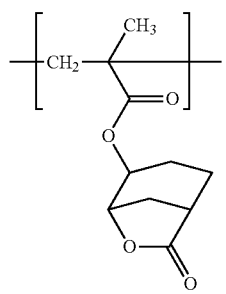
(a3-3-2)
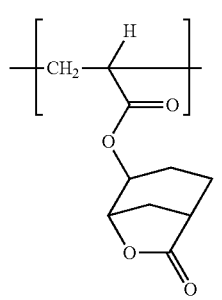
(a3-3-3)
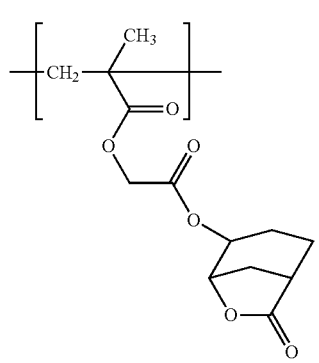
(a3-3-4)
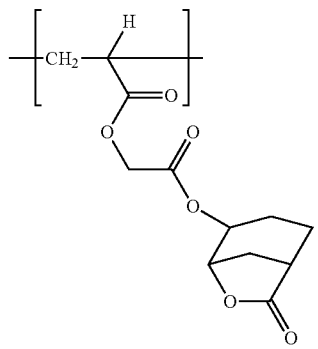
(a3-4-1)
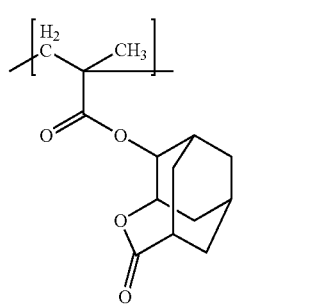
(a3-4-2)
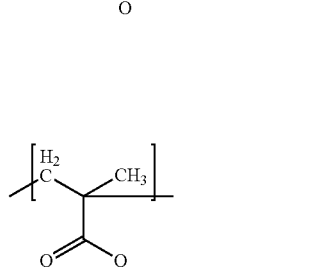
(a3-4-3)
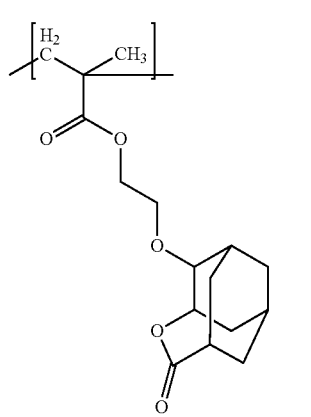

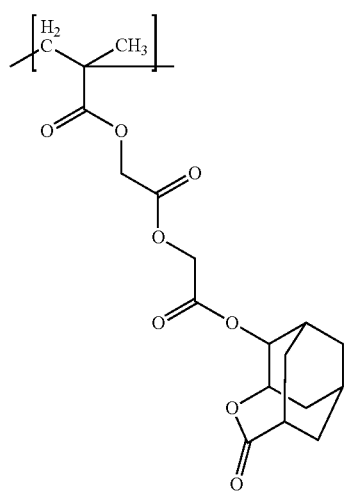
(a3-4-4)
(a3-4-5)
(a3-4-6)
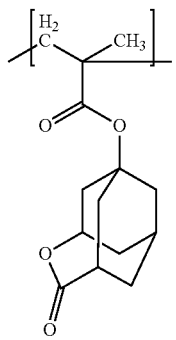
(a3-4-7)
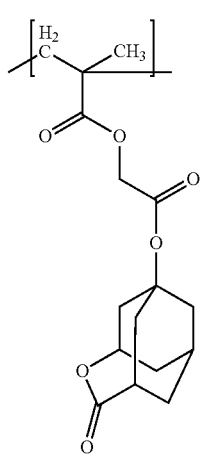
(a3-4-8)
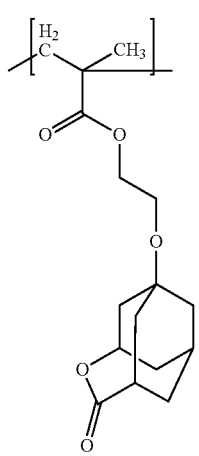
(a3-4-9)

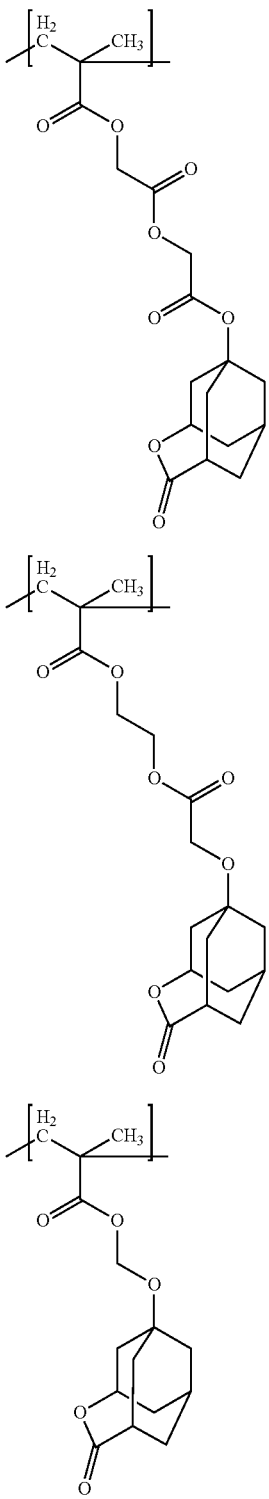

(a3-4-10)

(a3-4-11)

(a3-4-12)

Specific examples of the structural unit (a3) include those where methyl groups of formulae (a3-4-1) to (a3-4-6) have been replaced by hydrogen atoms.

When Resin (A) has the structural unit (a3), its content thereof is preferably 5 to 70% by mole, and more preferably 10 to 65% by mole and more preferably 10 to 60% by mole, based on all the structural units of the resin.

When Resin (A) has the structural unit represented by formula (a3-1), (a3-2), (a3-3) or (a3-4), the total content of them is preferably 5 to 60% by mole, and more preferably 5 to 50% by mole and more preferably 10 to 50% by mole, based on all the structural units of the resin.

Examples of another structural unit having no acid-labile group include a structural unit having a halogen atom and a structural unit which has a hydrocarbon not being removed therefrom by action of an acid. Herein, these structural units include no structural unit (II) described later, which generally has neither a cation nor an anion.

Examples of the structural unit having a halogen atom, which is sometimes referred to as "structural unit (a4)", include a structural unit represented by formula (a4-0).

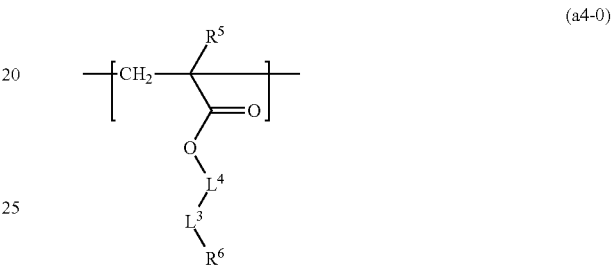

(a4-0)

In the formula (a4-0), $R^5$ represents a hydrogen atom or a methyl group, $L^4$ represents a single bond or a $C_1$ to $C_4$ saturated aliphatic hydrocarbon group, $L^3$ represents a $C_1$ to $C_8$ perfluoroalkanediyl group, or a $C_3$ to $C_{12}$ perfluorocycloalkanediyl group, and $R^6$ represents a hydrogen atom or a fluorine atom.

Examples of the saturated aliphatic hydrocarbon group for $L^4$ include C1 to C4 alkanediyl group, i.e., a linear alkanediyl group such as methylene, ethylene, propane-1,3-diyl, butane-1,4-diyl; and a branched alkanediyl group such as ethane-1,1-diyl, propane-1,2-diyl, butane-1,3-diyl, 2-methylpropane-1,3-diyl and 2-methylpropane-1,2-diyl groups.

$L^4$ is preferably a single bond, methylene or ethylene group, and more preferably a single bond or methylene group. Examples of the perfluoroalkanediyl group for $L^3$ include difluoromethylene, perfluoroethylene, perfluoroethyl fluoromethylene, perfluoropropane-1,3-diyl, a perfluoropropane-1,2-diyl, perfluoropropane-2,2-diyl, perfluorobutane-1,4-diyl, perfluorobutane-2,2-diyl, perfluorobutane-1,2-diyl, perfluoropentane-1,5-diyl, perfluoropentane-2,2-diyl, perfluoropentane-3,3-diyl, perfluorohexane-1,6-diyl, perfluorohexane-2,2-diyl, perfluorohexane-3,3-diyl, perfluoroheptane-1,7-diyl, perfluoroheptane-2,2-diyl, perfluoroheptane-3,4-diyl, perfluoroheptane-4,4-diyl, perfluorooctan-1,8-diyl, perfluorooctan-2,2-diyl, perfluorooctan-3,3-diyl and perfluorooctan-4,4-diyl groups.

Examples of the perfluoro cycloalkanediyl group for $L^3$ include perfluorocyclohexanediyl, perfluorocyclopentanediyl, perfluorocycloheptanediyl and perfluoroadamantanediyl groups.

$L^3$ is preferably a C1 to C6 perfluoroalkanediyl group, more preferably a C1 to C3 perfluoroalkanediyl group.

Examples of the structural unit represented by formula (a4-0) include those as follow.

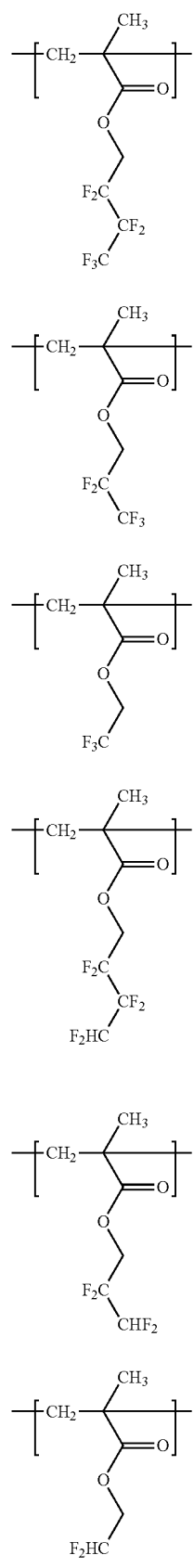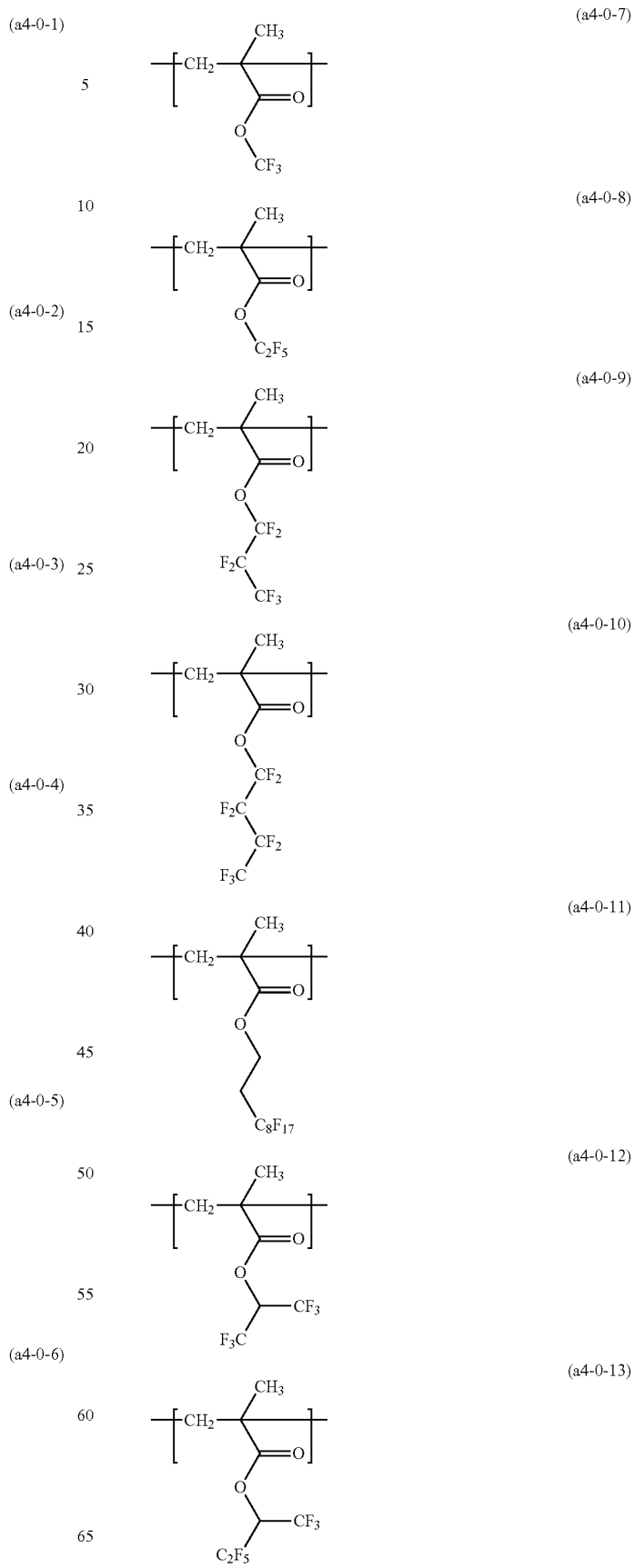

-continued (a4-0-14)

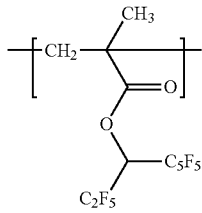

(a4-0-15)

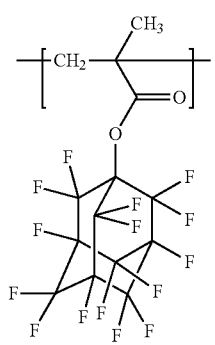

(a4-0-16)

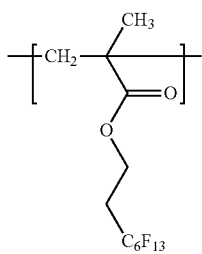

Examples of the structural unit represented by formula (a4-0) include the structural units represented by the above formulae in which a methyl group corresponding to $R^5$ has been replaced by a hydrogen atom.

Examples of the structural unit (a4) include those represented by formula (a4-1):

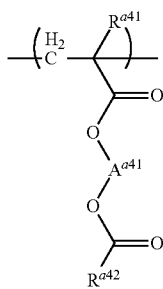

(a4-1)

wherein $R^{a41}$ represents a hydrogen atom or a methyl group, $R^{a42}$ represents an optionally substituted C1 to C20 hydrocarbon group where a methylene group can be replaced by an oxygen atom or a carbonyl group, and $A^{a41}$ represents an optionally substituted C1 to C6 alkanediyl group or a group represented by formula (a-g1), $$*\text{-}A^{a42}\text{-}(\text{-}X^{a41}\text{-}A^{a43}\text{-})_s X^{a42}\text{-}A^{a44}\text{-}*$$ (a-g1)

wherein s represents 0 or 1, $A^{a42}$ and $A^{a44}$ each independently represent an optionally substituted C1 to C5 aliphatic hydrocarbon group, $A^{a43}$ represents a single bond or an optionally substituted C1 to C5 aliphatic hydrocarbon group, and $X^{a41}$ and $X^{a42}$ each independently represent —O—, —CO—, —CO—O— or —O—CO—, provided that the total number of the carbon atoms contained in the group of $A^{a42}$, $A^{a43}$, $A^{a44}$, $X^{a41}$ and $X^{a42}$ is 7 or less, at least one of $A^{a41}$ and $R^{a42}$ has a halogen atom as a substituent, and

* and ** represent a binding site, and * represents a binding site to —O—CO—$R^{a42}$.

The hydrocarbon group for $R^{a42}$ may be a chain aliphatic hydrocarbon group, a cyclic aliphatic hydrocarbon group, an aromatic hydrocarbon group and a combination thereof.

The chain aliphatic hydrocarbon group and the cyclic aliphatic hydrocarbon group may have a carbon-carbon unsaturated bond, and is preferably a chain saturated aliphatic hydrocarbon group and a cyclic saturated aliphatic hydrocarbon group. Examples of the saturated aliphatic hydrocarbon group include a linear or branched alkyl group, a monocyclic or polycyclic alicyclic hydrocarbon group, and an aliphatic hydrocarbon group formed by combining the alkyl group and the alicyclic hydrocarbon group.

Examples of the chain aliphatic hydrocarbon group include an alkyl group such as methyl, ethyl, propyl, butyl, pentyl, hexyl, heptyl, octyl, decyl, dodecyl and hexadecyl groups.

Examples of the alicyclic hydrocarbon group include a cycloalkyl group such as cyclopentyl, cyclohexyl, cycloheptyl, cyclooctyl groups; and polycyclic hydrocarbon groups such as decahydronaphtyl, adamantyl and norbornyl groups as well as groups below. * represents a binding site.

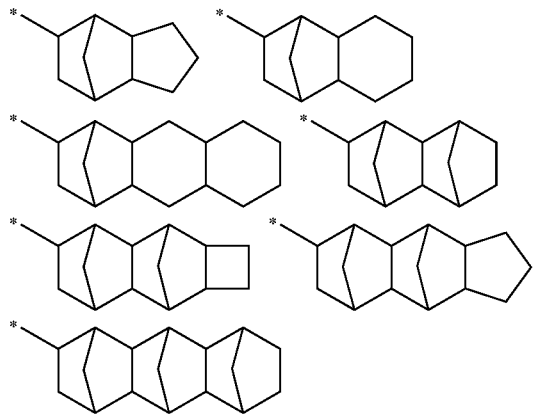

Examples of the aromatic hydrocarbon group include an aryl group such as phenyl, naphthyl, anthryl, biphenyl, phenanthryl and fluorenyl groups.

The hydrocarbon group for $R^{a42}$ is preferably a chain saturated aliphatic hydrocarbon group, a cyclic aliphatic hydrocarbon group, and a combination thereof. The hydrocarbon group may have a carbon-carbon unsaturated bond, is preferably a chain and a cyclic saturated aliphatic hydrocarbon groups, and a combination thereof.

Examples of the substituent for $R^{a42}$ include a halogen atom or a group represented by formula (a-g3):

$$*\text{—}X^{a43}\text{-}A^{a45}$$ (a-g3)

wherein $X^{a43}$ represent an oxygen atom, a carbonyl group, a carbonyloxy group or an oxycarbonyl group; $A^{a45}$ represents a C1 to C17 aliphatic hydrocarbon group that has a halogen atom; and * represents a binding site.

Examples of the halogen atom include a fluorine atom, a chlorine atom, a bromine atom and an iodine atom, and preferably a fluorine atom.

Examples of the aliphatic hydrocarbon group for $A^{a45}$ include the same ones as those for $R^{a42}$.

$R^{a42}$ is preferably an aliphatic hydrocarbon group that may have a halogen atom, and more preferably an alkyl group having a halogen atom and/or an aliphatic hydrocarbon group having the group represented by the formula (a-g3).

When $R^{a42}$ is an aliphatic hydrocarbon group having a halogen atom, an aliphatic hydrocarbon group having a fluorine atom is preferred, a perfluoroalkyl group or a perfulorocycloalkyl group are more preferred, a C1 to C6 perfluoroalkyl group is still more preferred, a C1 to C3 perfluoroalkyl group is particularly preferred Examples of the perfluoroalkyl group include perfluoromethyl, perfluoroethyl, perfluoropropyl, perfluorobutyl, perfluoropentyl, perfluorohexyl, perfluoroheptyl and perfluorooctyl groups. Examples of the perfluorocycloalkyl group include perfluorocyclohexyl group.

When $R^{a42}$ is an aliphatic hydrocarbon group having the group represented by the formula (a-g3), the total number of the carbon atoms contained in the aliphatic hydrocarbon group including the group represented by the formula (a-g3) is preferably 15 or less, more preferably 12 or less. The number of the group represented by the formula (a-g3) is preferably one when the group represented by the formula (a-g3) is the substituent.

The aliphatic hydrocarbon group having the group represented by the formula (a-g3) is more preferably a group represented by formula (a-g2):

-$A^{a46}$-$X^{a44}$-$A^{a47}$-  (a-g2)

wherein $A^{a46}$ represents a C1 to C17 aliphatic hydrocarbon group that may have a halogen atom, $X^{a44}$ represent a carbonyloxy group or an oxycarbonyl group, $A^{a47}$ represents a C1 to C17 aliphatic hydrocarbon group that may have a halogen atom, provided that the total number of the carbon atoms contained in the group of $A^{a46}$, $X^{a44}$ and $A^{a47}$ is 18 or less, at least one of $A^{a46}$ and $A^{a47}$ has a halogen atom, and

* represents a binding site to a carbonyl group.

The aliphatic hydrocarbon group for $A^{a46}$ has preferably 1 to 6 carbon atoms, more preferably 1 to 3 carbon atoms.

The aliphatic hydrocarbon group for $A^{a47}$ has preferably 4 to 15 carbon atoms, more preferably 5 to 12 carbon atoms. $A^{a47}$ is more preferably a cyclohexyl group or an adamantyl group. Preferred examples of *-$A^{a46}$-$X^{a44}$-$A^{a47}$ include the following ones.

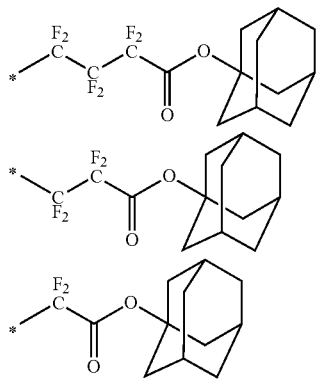

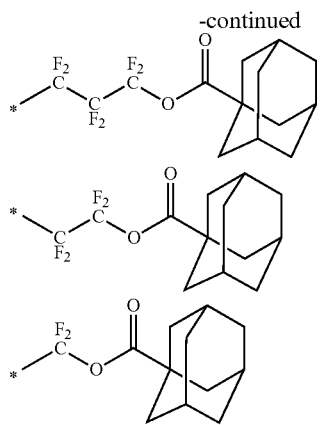

Examples of the alkanediyl group for $A^{a41}$ include a linear alkanediyl group such as methylene, ethylene, propane-1,3-diyl, butane-1,4-diyl, pentane-1,5-diyl and hexane-1,6-diyl groups; and a branched alkanediyl group such as propane-1,2-diyl, butan-1,3-diyl, 2-methylpropane-1,2-diyl, 1-methylbutane-1,4-diyl, 2-methylbutane-1,4-diyl groups.

Examples of the substituent on the alkanediyl group for $A^{a41}$ include a hydroxy group and a C1 to C6 alkoxy group.

$A^{a41}$ is preferably a C1 to C4 alkanediyl group, more preferably a C2 to C4 alkanediyl group, and still more preferably an ethylene group.

In the group represented by the formula (a-g1) (which is sometimes referred to as "group (a-g1)"), examples of the aliphatic hydrocarbon group for $A^{a42}$, $A^{a43}$ and $A^{a44}$ include methylene, ethylene, propane-1,3-diyl, propane-1,2-diyl, butane-1,4-diyl, 1-methylpropane-1,3-diyl, 2-methylpropane-1,3-diyl and 2-methylpropane-1,2-diyl groups.

Examples of the substituent on the aliphatic hydrocarbon group for $A^{a42}$, $A^{a43}$ and $A^{a44}$ include a hydroxy group and a C1 to C6 alkoxy group.

"s" is preferably 0.

Examples of the group (a-g1) in which $X^{a42}$ represents an oxygen atom, a carbonyl group, a carbonyloxy group, or an oxycarbonyl group include the following ones. In the formula, * and  each represent a binding site, and  represents a binding site to —O—CO—$R^{a42}$.

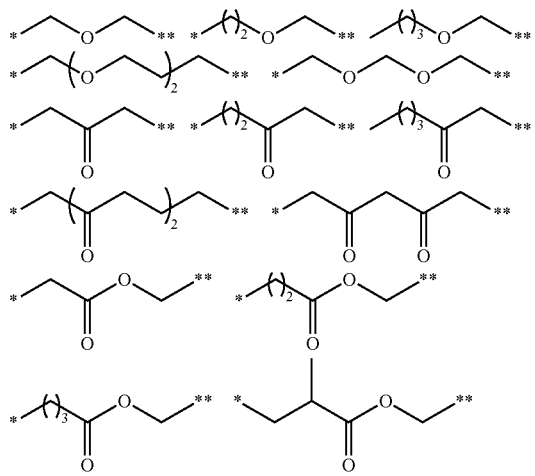

-continued

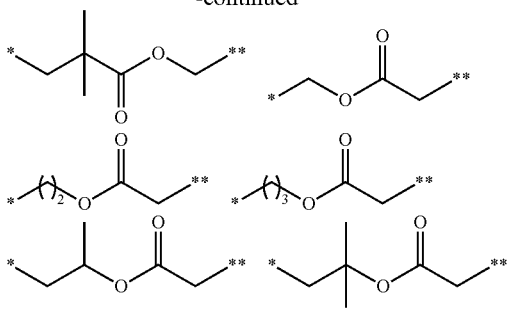

The structural unit represented by the formula (a4-1) is preferably structural units represented by formula (a4-2) and formula (a4-3):

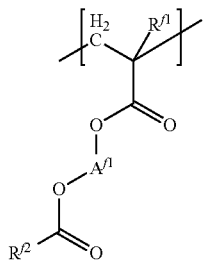

(a4-2)

wherein $R^{f1}$ represents a hydrogen atom or a methyl group,
$A^{f1}$ represent a C1 to C6 alkanediyl group, and
$R^{f2}$ represents a C1 to C10 hydrocarbon group that has a fluorine atom:

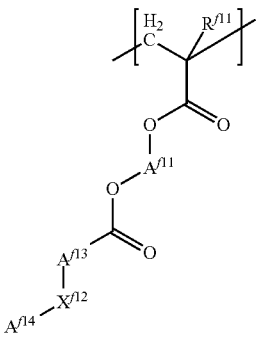

(a4-3)

where $R^{f11}$ represents a hydrogen atom or a methyl group,
$A^{f11}$ represent a C1 to C6 alkanediyl group,
$A^{f13}$ represents a C1 to C18 aliphatic hydrocarbon group that may have a fluorine atom,
$X^{f12}$ represents an oxycarbonyl group or a carbonyloxy group,
$A^{f14}$ represents a C1 to C17 aliphatic hydrocarbon group that may have a fluorine atom, and
provided that at least one of $A^{f12}$ and $A^{f14}$ represents an aliphatic hydrocarbon group having a fluorine atom.

Examples of the alkanediyl group for $A^{f1}$ include a linear alkanediyl group such as methylene, ethylene, propane-1,3-diyl, propane-1,2-diyl, butane-1,4-diyl, pentane-1,5-diyl and hexane-1,6-diyl groups;

a branched alkanediyl group such as 1-methylpropane-1,3-diyl, 2-methylpropane-1,3-diyl, 2-methylpropane-1,2-diyl, 1-methylbutane-1,4-diyl and 2-methylbutane-1,4-diyl groups.

The hydrocarbon group for $R^{f2}$ includes an aliphatic hydrocarbon group and an aromatic hydrocarbon group. The aliphatic hydrocarbon group includes chain and cyclic groups, and a combination thereof.

The aliphatic hydrocarbon group is preferably an alkyl group and a cyclic aliphatic hydrocarbon group.

Examples of the alkyl group include methyl, ethyl, n-propyl, isopropyl, n-butyl, sec-butyl, tert-butyl, n-pentyl, n-hexyl, n-heptyl, n-octyl and 2-ethylhexyl groups.

Examples of the cyclic aliphatic hydrocarbon group include any of a monocyclic group and a polycyclic group. Examples of the monocyclic alicyclic hydrocarbon group include a cycloalkyl group such as cyclopropyl, cyclobutyl, cyclopentyl, cyclohexyl, methylcyclohexyl, dimethylcyclohexyl, cycloheptyl, cyclooctyl, and cyclodecyl groups. Examples of the polycyclic hydrocarbon groups includes decahydronaphthyl, adamantyl, 2-alkyladamantane-2-yl, 1-(adamantane-1-yl)alkane-1-yl, norbornyl, methylnorbornyl and isobornyl groups.

Examples of the hydrocarbon group having a fluorine atom for $R^{f2}$ include an alkyl group having a fluorine atom and an alicyclic hydrocarbon group having a fluorine atom.

Specific examples of an alkyl group having a fluorine atom include a fluorinated alkyl group such as difluoromethyl, trifluoromethyl, 1,1-difluoroethyl, 2,2-difluoroethyl, 2,2,2-trifluoroethyl, perfluoroethyl, 1,1,2,2-tetrafluoropropyl, 1,1,2,2,3,3-hexafluoropropyl, perfluoroethylmethyl, 1-(trifluoromethyl)-1,2,2,2-tetrafluoroethyl, perfluoropropyl, 1-(trifluoromethyl)-2,2,2-trifluoroethyl, perfluoropropyl, 1,1,2,2-tetrafluorobutyl, 1,1,2,2,3,3-hexafluorobutyl, 1,1,2,2,3,3,4,4-octafluorobutyl, perfluorobutyl, 1,1-bis(trifluoro)methyl-2,2,2-trifluoroethyl, 2-(perfluoropropyl)ethyl, 1,1,2,2,3,3,4,4-octafluoropentyl, perfluoropentyl, 1,1,2,2,3,3,4,4,5,5-decafluoropentyl, 1,1-bis(trifluoromethyl)2,2,3,3,3-pentafluoropropyl, 2-(perfluorobutyl)ethyl, 1,1,2,2,3,3,4,4,5,5-decafluorohexyl, 1,1,2,2,3,3,4,4,5,5,6,6-dodecafluorohexyl, perfluoropentylmethyl and perfluorohexyl groups.

Examples of the alicyclic hydrocarbon group having a fluorine atom include a fluorinated cycloalkyl group such as perfluorocyclohexyl and perfluoroadamantyl groups.

In the formula (a4-2), $A^{f1}$ is preferably a C2 to C4 alkanediyl group, and more preferably an ethylene group.

$R^{f2}$ is preferably a C1 to C6 fluorinated alkyl group.

Examples of the alkanediyl group for $A^{f11}$ include the same ones as those for $A^{f1}$.

Examples of the aliphatic hydrocarbon group for $A^{f13}$ include any of a divalent chain or cyclic aliphatic hydrocarbon group, or a combination thereof. The aliphatic hydrocarbon group may have a carbon-carbon unsaturated bond, and is preferably a saturated aliphatic hydrocarbon group.

The aliphatic hydrocarbon group that may have a fluorine atom for $A^{f13}$ is preferably the saturated aliphatic hydrocarbon group that may have a fluorine atom, and more preferably perfluoroalkandiyl group.

Examples of the divalent chain aliphatic hydrocarbon that may have a fluorine atom include an alkanediyl group such as methylene, ethylene, propanediyl, butanediyl and pentanediyl groups; a perfluoroalkanediyl group such as difluoromethylene, perfluoroethylene, perfluoropropanediyl, perfluorobutanediyl and perfluoropentanediyl groups.

The divalent cyclic aliphatic hydrocarbon group that may have a fluorine atom is any of monocyclic group and a polycyclic group.

Examples of the monocyclic aliphatic hydrocarbon group include cyclohexanediyl and perfluorocyclohexanediyl groups.

Examples of the polycyclic aliphatic hydrocarbon group include adamantanediyl, norbornanediyl andperfluoroadamantanediyl groups.

Examples of the aliphatic hydrocarbon group for $A'^{14}$ include a chain aliphatic hydrocarbon group, a cyclic aliphatic hydrocarbon group, and a combination thereof. The aliphatic hydrocarbon group may have a carbon-carbon unsaturated bond, and is preferably a saturated aliphatic hydrocarbon group.

The aliphatic hydrocarbon group that may have a fluorine atom for $A'^{14}$ is preferably the saturated aliphatic hydrocarbon group that may have a fluorine atom.

Examples of the chain aliphatic hydrocarbon group that may have a halogen atom include trifluoromethyl, difluoromethyl, methyl, perfluoromethyl, 1,1,1-trifluoroethyl, 1,1,2,2-tetrafluoroethyl, ethyl, perfluoropropyl, 1,1,1,2,2-pentafluoropropyl, propyl, perfluorobutyl, 1,1,2,2,3,3,4,4-octafluorobutyl, butyl, perfluoropentyl, 1,1,1,2,2,3,3,4,4-nonafluoropentyl, pentyl, hexyl, perfluorohexyl, hepthyl, perfluoroheptyl, octyl and perfluorooctyl groups.

The cyclic aliphatic hydrocarbon group that may have a fluorine atom may be any of a monocyclic hydrocarbon group and a polycyclic hydrocarbon group. Examples of the group containing the monocyclic aliphatic hydrocarbon group include cyclopropylmethyl, cyclopropyl, cyclobutylmethyl, cyclopentyl, cyclohexyl and perfluorocyclohexyl groups. Examples of the group containing the polycyclic aliphatic hydrocarbon group include adamantyl, adamantylmethyl, norbornyl, norbornylmethyl, perfluoroadamantyl and perfluoroadamantylmethyl groups.

In the formula (a4-3), $A'^{11}$ is preferably an ethylene group.

The aliphatic hydrocarbon group for $A'^{13}$ is preferably a C1 to C6 aliphatic hydrocarbon group, more preferably a C2 to C3 aliphatic hydrocarbon group.

The aliphatic hydrocarbon group for $A'^{13}$ is preferably a C3 to C12 aliphatic hydrocarbon group, more preferably a C3 to C10 aliphatic hydrocarbon group. Among these, $A'^{14}$ is preferably a group containing a C3 to C12 alicyclic hydrocarbon group, more preferably cyclopropylmethyl, cyclopentyl, cyclohexyl, norbornyl and adamantyl groups.

Examples of the structural unit represented by formula (a4-2) include structural units represented by formula (a4-1-1) to formula (a4-1-22).

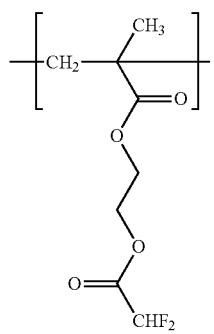

(a4-1-1)

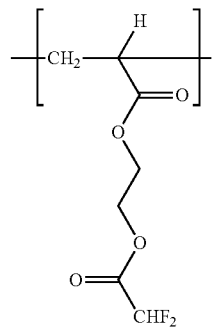

(a4-1-2)

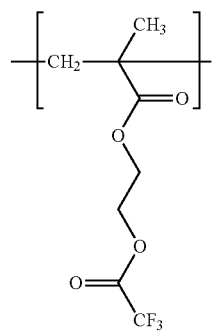

(a4-1-3)

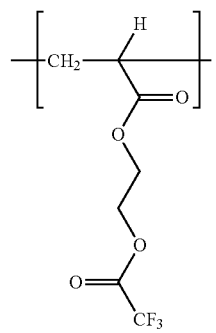

(a4-1-4)

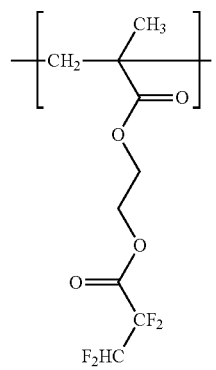

(a4-1-5)

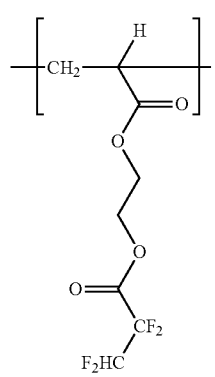
(a4-1-6)
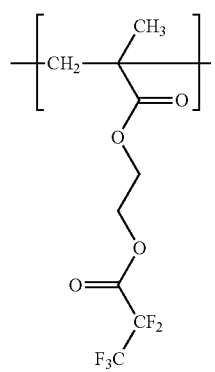
(a4-1-7)
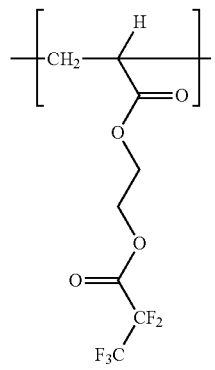
(a4-1-8)
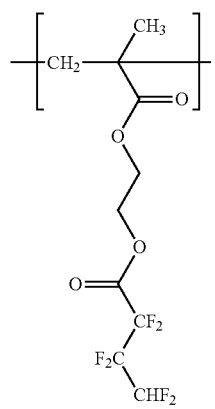
(a4-1-9)
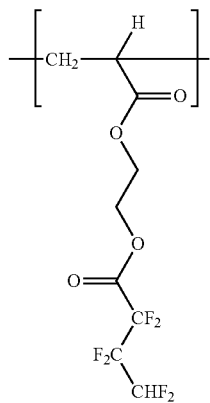
(a4-1-10)
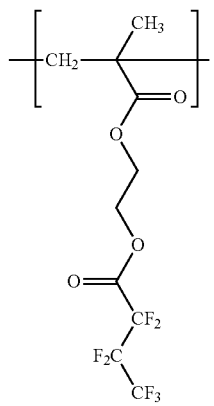
(a4-1-11)
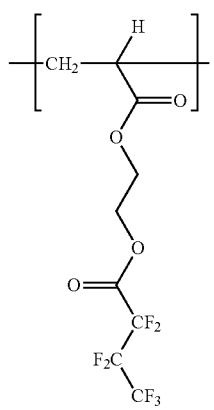
(a4-1-12)
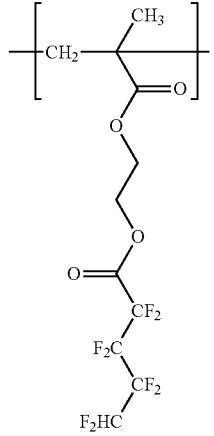
(a4-1-13)

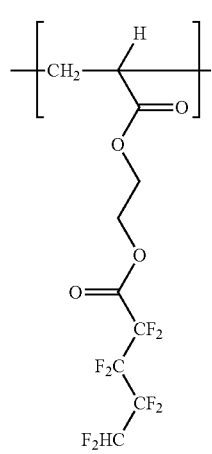
(a4-1-14)
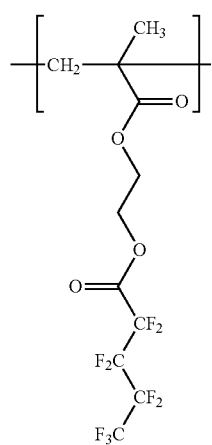
(a4-1-15)
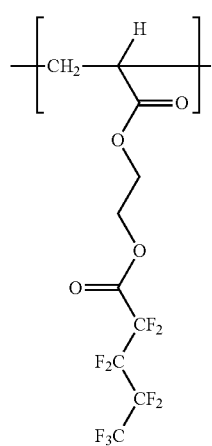
(a4-1-16)
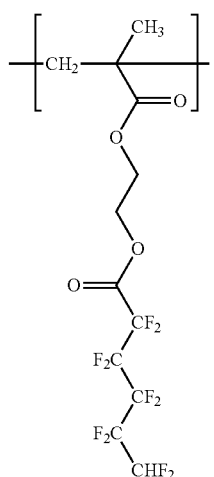
(a4-1-17)
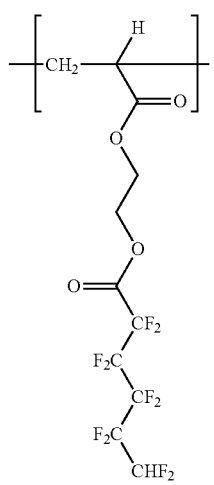
(a4-1-18)
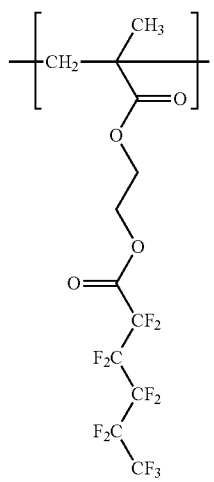
(a4-1-19)

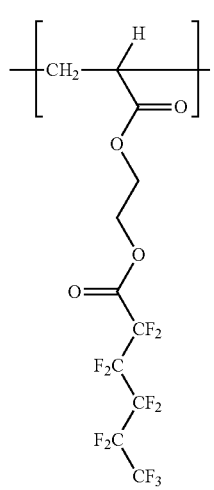
(a4-1-20)
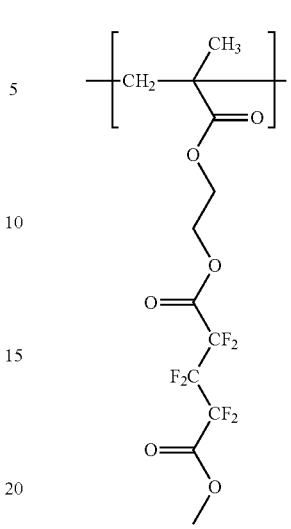
(a4-1'-1)
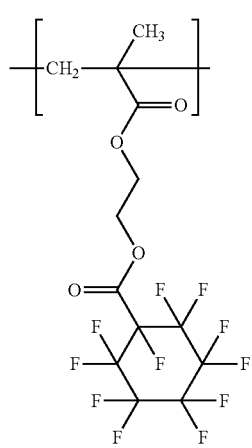
(a4-1-21)
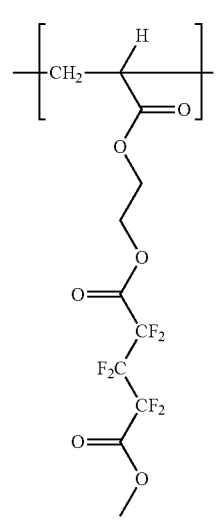
(a4-1'-2)
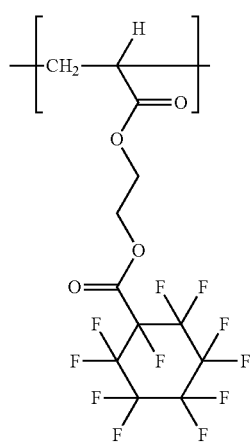
(a4-1-22)
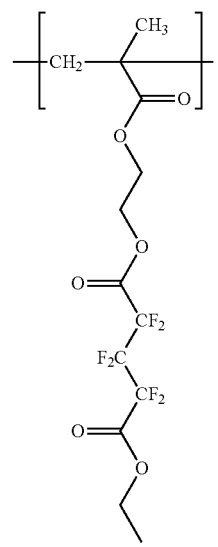
(a4-1'-3)
Examples of the structural unit represented by formula (a4-3) include structural units represented by formula (a4-1'-1) to formula (a4-1'-22).

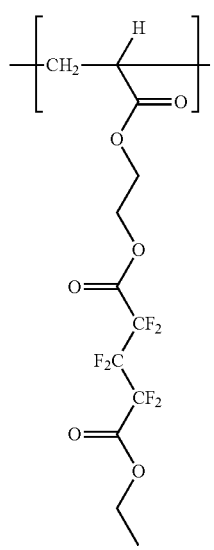
(a4-1'-4)
(a4-1'-5)
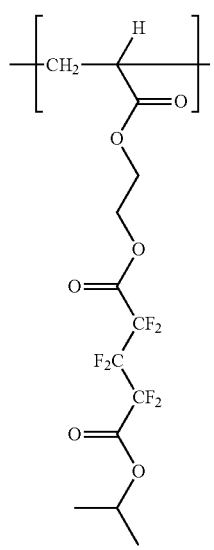
(a4-1'-6)
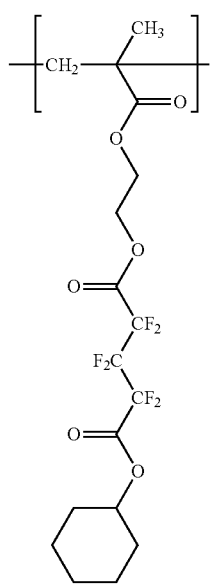
(a4-1'-7)
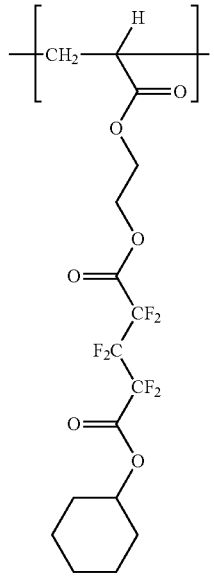
(a4-1'-8)

(a4-1'-9)

(a4-1'-11)

(a4-1'-10)

(a4-1'-12)

(a4-1'-13)
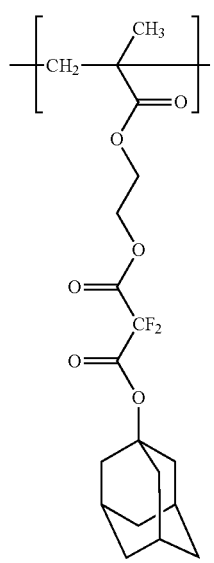
(a4-1'-14)
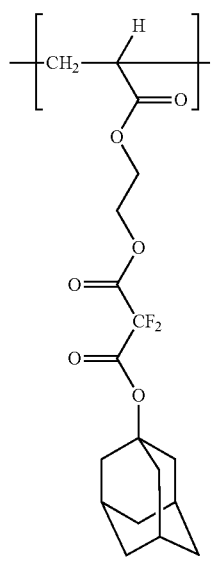
(a4-1'-15)
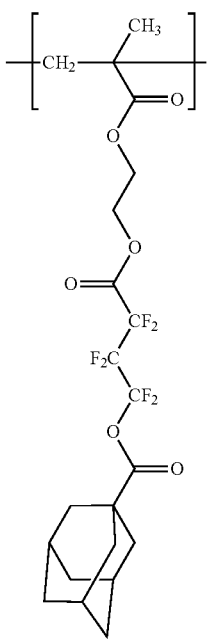
(a4-1'-16)
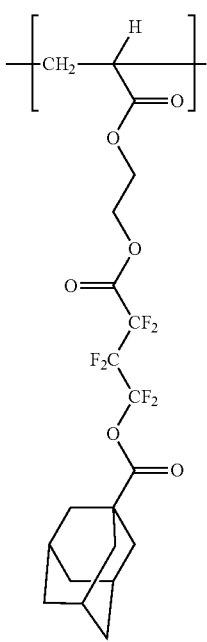

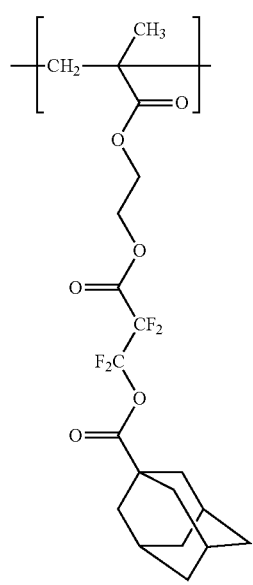 (a4-1'-17)
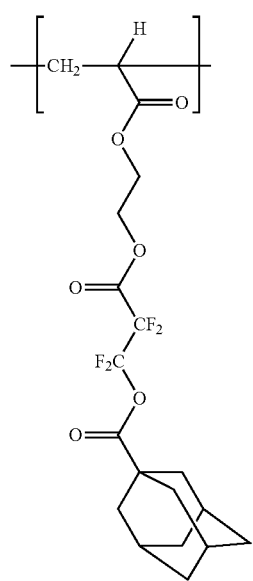 (a4-1'-18)
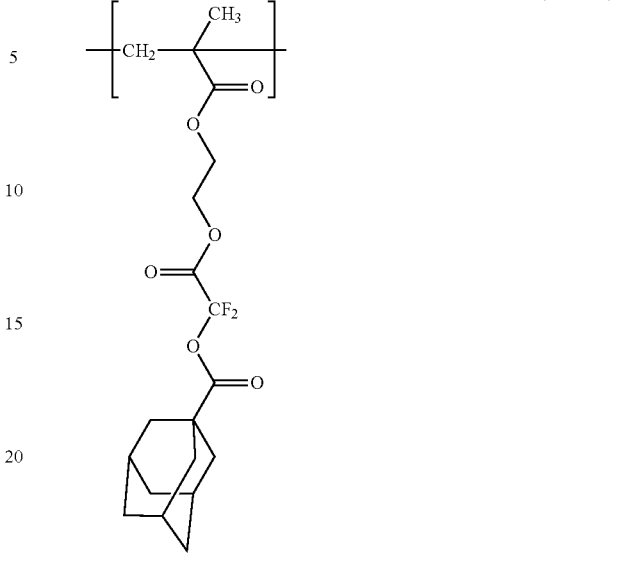 (a4-1'-19)
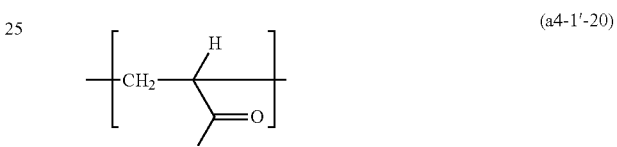 (a4-1'-20)
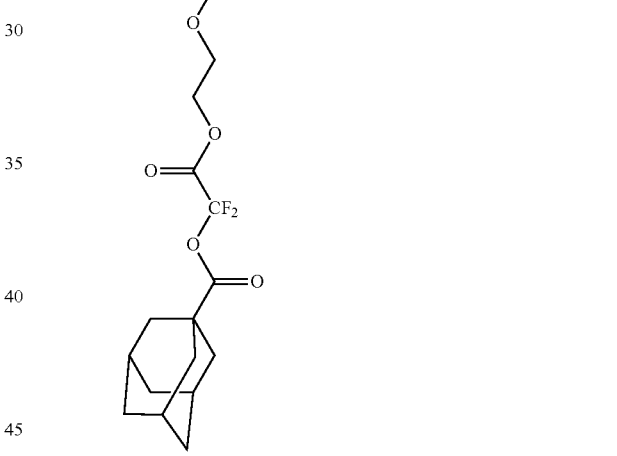 (a4-1'-21)

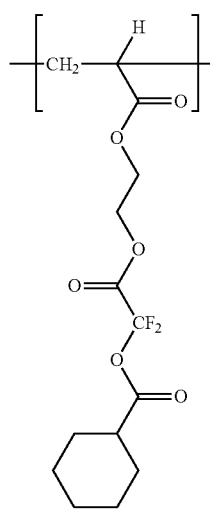

(a4-1'-22)

Examples of the structural unit (a4) include a structural unit represented by formula (a4-4):

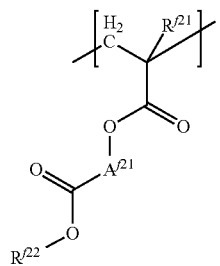

(a4-4)

wherein $R^{/21}$ represents a hydrogen atom or a methyl group; $A^{/21}$ represents *—$(CH_2)_{j1}$—, *—$(CH_2)_{j2}$—O—$(CH_2)_{j3}$— or *—$(CH_2)_{j4}$—CO—O—$(CH_2)_{j5}$—, where * represents a binding site to an oxygen atom; j1 to j5 each independently represents an integer of 1 to 6; and $R^{/22}$ represents a C1 to C10 hydrocarbon group having a fluorine atom.

Examples of the hydrocarbon group having a fluorine atom for $R^{/22}$ include the same ones as those for $R^2$ in the formula (a4-2). $R^{/22}$ is preferably a C1 to C10 alkyl group having a fluorine atom or a C3 to C10 alicyclic hydrocarbon group having a fluorine atom, more preferably a C1 to C10 alkyl group having a fluorine atom, and still more preferably a C1 to C6 alkyl group having a fluorine atom.

In the formula (a4-4), $A^{/21}$ is preferably —$(CH_2)_{j1}$—, more preferably a methylene group or an ethylene group, and still more preferably a methylene group.

Examples of the structural unit represented by the formula (a4-4) include the following ones.

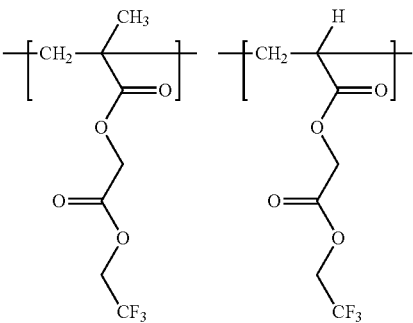

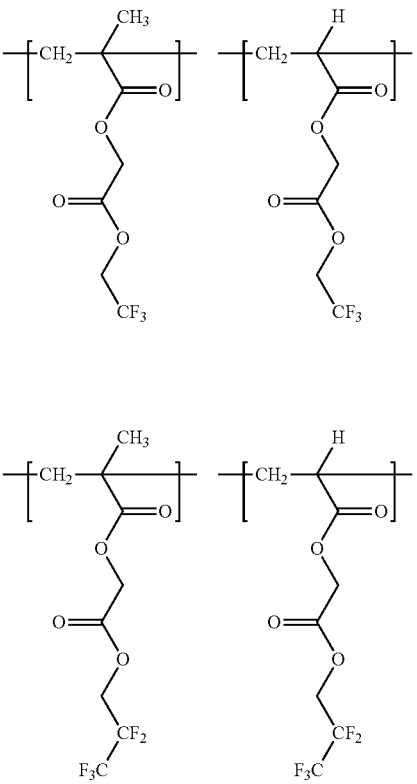

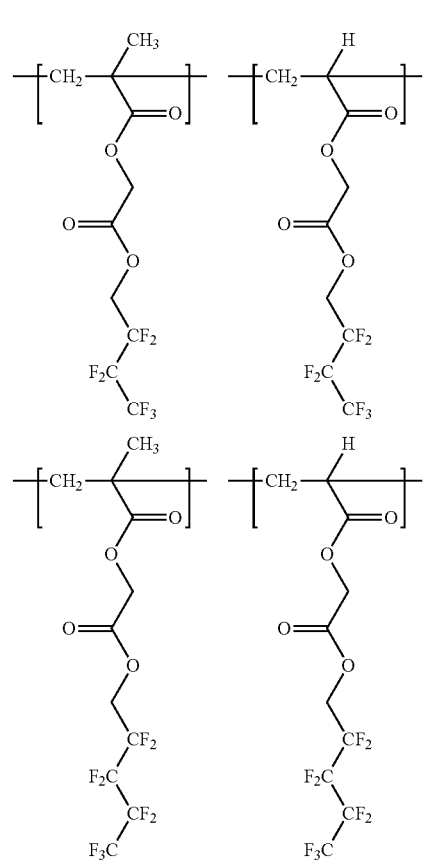

151
-continued
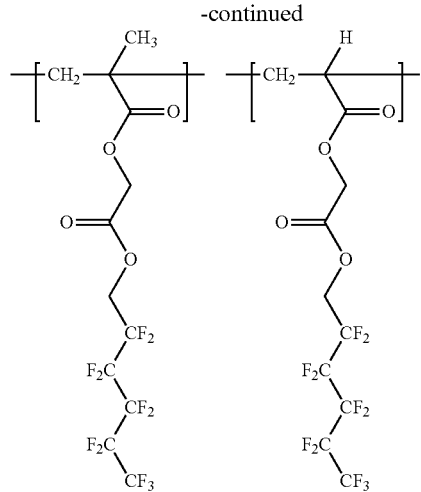
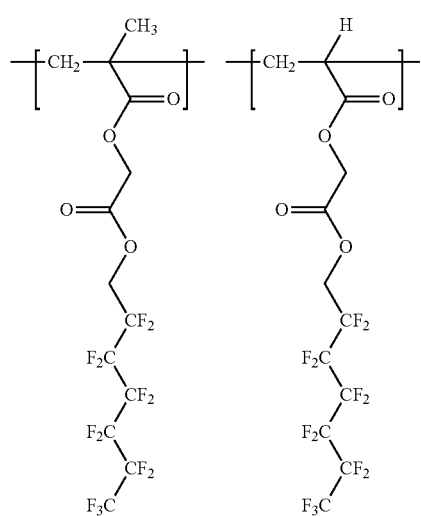
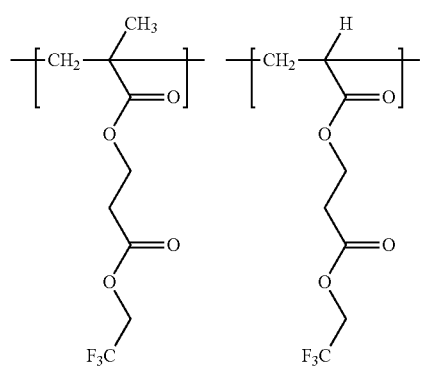
152
-continued
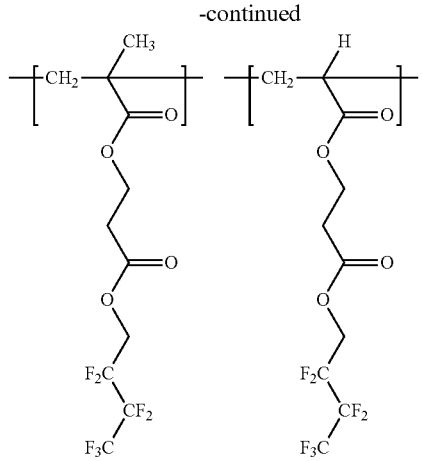
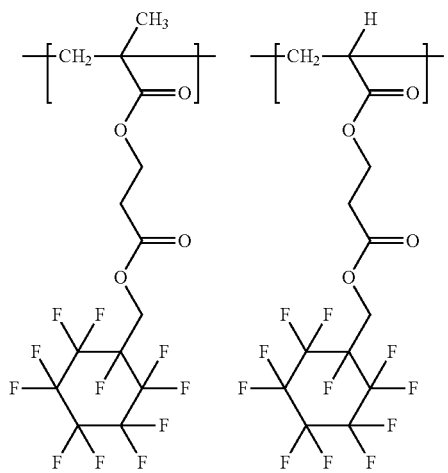
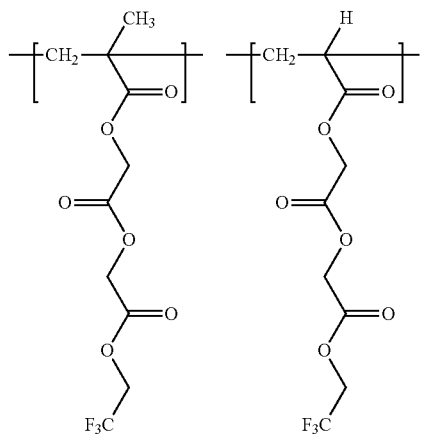

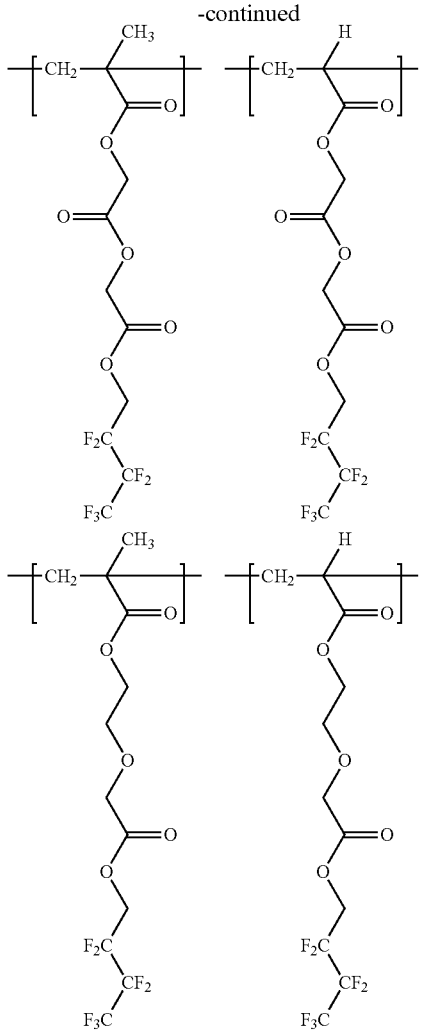

When Resin (A) has the structural unit (a4), the content thereof is usually 1 to 20% by mole, preferably 2 to 15% by mole, and more preferably 3 to 10% by mole, based on all the structural units of the resin.

The structural unit which has a hydrocarbon not being removed therefrom by action of an acid may have a linear, branched or cyclic hydrocarbon, preferably an alicyclic hydrocarbon group.

Examples of the structural unit having a hydrocarbon group not being removed therefrom by action of an acid include one represented by formula (a5-1):

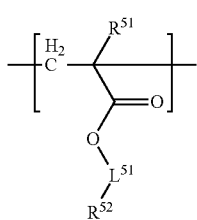
(a5-1)

where $R^{51}$ represents a hydrogen atom or a methyl group; $R^{52}$ represents a C3 to C18 alicyclic hydrocarbon group, provided that the alicyclic hydrocarbon group has no substituent on the carbon atom bonded to $L^{51}$; and $L^{51}$ represents a single bond or a C1 to C8 alkanediyl group where a methylene group can be replaced by an oxygen atom or carbonyl group.

The alicyclic hydrocarbon group represented by $R^{52}$ may be monocyclic or polycyclic one.

Examples of the alicyclic hydrocarbon group include a monocyclic hydrocarbon group such as a C3 to C18 cycloalkyl group (e.g. a cyclopropyl group, a cyclobutyl group, a cyclopentyl group, a cyclohexyl group) and a polycyclic alicyclic hydrocarbon group such as an adamantyl group, or a norbornyl group.

Examples of the alicyclic hydrocarbon group having a substituent include a 3-hydroxyadamantyl group, and a 3-methyladamantyl group. Examples of the C1 to C8 aliphatic hydrocarbon group include an alkyl group such as methyl, ethyl, n-propyl, isopropyl, n-butyl, sec-butyl, tert-butyl, n-pentyl, n-hexyl, n-heptyl, 2-ethylhexyl and n-octyl groups.

Examples of the alicyclic hydrocarbon group having a substituent for $R^{52}$ include 3-hydroxyadamantyl group and 3-methyladamantyl group. $R^{52}$ is preferably an unsubstituted C3 to C18 alicyclic hydrocarbon group, and more preferably an adamantyl, norbornyl or cyclohexyl group.

Examples of the divalent saturated hydrocarbon group for $L^{51}$ include a divalent saturated aliphatic hydrocarbon group and a divalent saturated alicyclic hydrocarbon group, and a divalent saturated aliphatic hydrocarbon group is preferred.

Examples of the divalent saturated aliphatic hydrocarbon group include an alkanediyl group such as methylene, ethylene, propanediyl, butanediyl and pentanediyl groups.

Examples of the divalent saturated alicyclic hydrocarbon group include any of a monocyclic group and a polycyclic group. Examples of the monocyclic group include a cycloalkanediyl group such as cyclopentanediyl and cyclohexanediyl groups. Examples of the polycyclic group include adamantanediyl and norbornanediyl groups.

Examples of the saturated hydrocarbon group in which a methylene group has been replaced by an oxygen atom or a carbonyl group include groups represented by formula (L1-1) to formula (L1-4). In formula (L1-1) to formula (L1-4), * represents a binding site to an oxygen atom.

(L1-1)

(L1-2)

(L1-3)

(L1-4)

In the formulae, $X^{x1}$ represents an oxycarbonyl group or a carbonyloxy group, $L^{x1}$ represents a C1 to C16 divalent saturated aliphatic hydrocarbon group, $L^{x2}$ represents a single bond or a C1 to C15 divalent saturated aliphatic hydrocarbon group, provided that the total number of the carbon atoms contained in the groups of $L^{X1}$ and $L^{X2}$ is 16 or less;

$L^{X3}$ represents a single bond or a C1 to C17 divalent saturated aliphatic hydrocarbon group, $L^{X4}$ represents a single bond or a C1 to C16 divalent saturated aliphatic hydrocarbon group, provided that the total number of the carbon atoms contained in the groups of $L^{X3}$ and $L^{X4}$ is 17 or less;

$L^{X5}$ represents a C1 to C15 divalent saturated aliphatic hydrocarbon group, $L^{X6}$ and $L^{X7}$ each independently represent a single bond or a C1 to C14 divalent saturated aliphatic hydrocarbon group, provided that the total number of the carbon atoms contained in the groups of $L^{X5}$, $L^{X6}$ and $L^{X7}$ is 15 or less;

$L^{X8}$ and $L^{X9}$ each independently represent a single bond or a C1 to C12 divalent saturated aliphatic hydrocarbon group, $W^{X1}$ represents a C3 to C15 divalent saturated alicyclic hydrocarbon group, provided that the total number of the carbon atoms contained in the groups of $L^{X8}$, $L^{X9}$ and $W^{X1}$ is 15 or less.

$L^{X1}$ is preferably a C1 to C8 divalent saturated aliphatic hydrocarbon group, and more preferably a methylene group or an ethylene group.

$L^{X2}$ is preferably a single bond or a C1 to C8 divalent saturated aliphatic hydrocarbon group, and more preferably a single bond.

$L^{X3}$ is preferably a C1 to C8 divalent saturated aliphatic hydrocarbon group.

$L^{X4}$ is preferably a single bond or a C1 to C8 divalent saturated aliphatic hydrocarbon group.

$L^{X5}$ is preferably a C1 to C8 divalent saturated aliphatic hydrocarbon group, and more preferably a methylene group or an ethylene group.

$L^{X6}$ is preferably a single bond or a C1 to C8 divalent saturated aliphatic hydrocarbon group, and more preferably a methylene group or an ethylene group.

$L^{X7}$ is preferably a single bond or a C1 to C8 divalent saturated aliphatic hydrocarbon group.

$L^{X8}$ is preferably a single bond or a C1 to C8 divalent saturated aliphatic hydrocarbon group, and more preferably a single bond or a methylene group.

$L^{X9}$ is preferably a single bond or a C1 to C8 divalent saturated aliphatic hydrocarbon group, and more preferably a single bond or a methylene group.

$W^{X1}$ is preferably a C3 to C10 divalent saturated alicyclic hydrocarbon group, and more preferably a cyclohexanediyl or adamantanediyl group.

Examples of the group represented by the formula (L1-1) include the following ones.

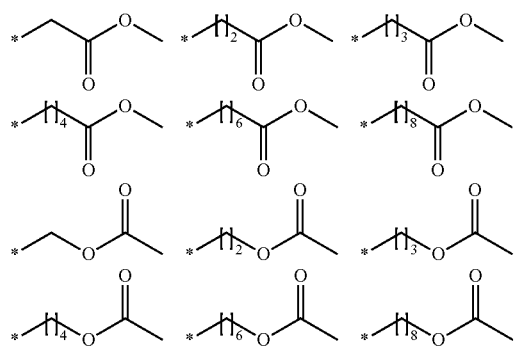

Examples of the group represented by the formula (L1-2) include the following ones.

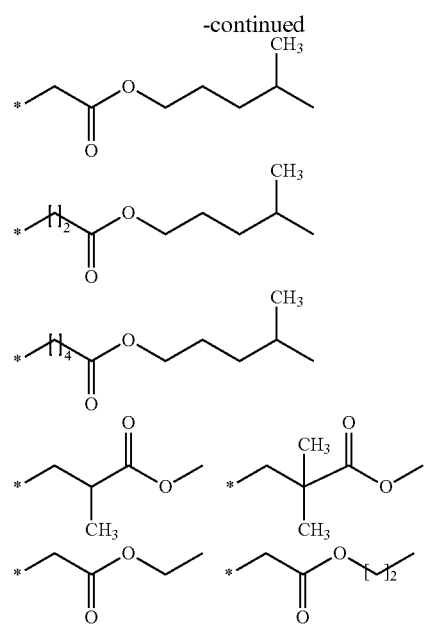

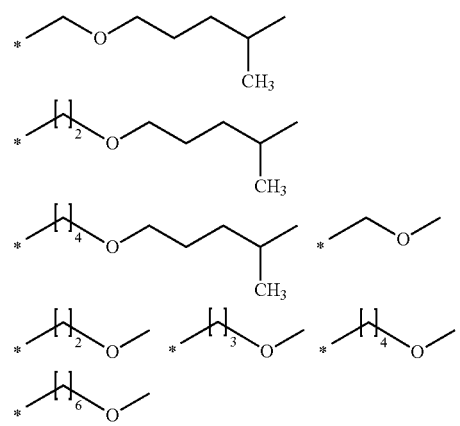

Examples of the group represented by the formula (L1-3) include the following ones.

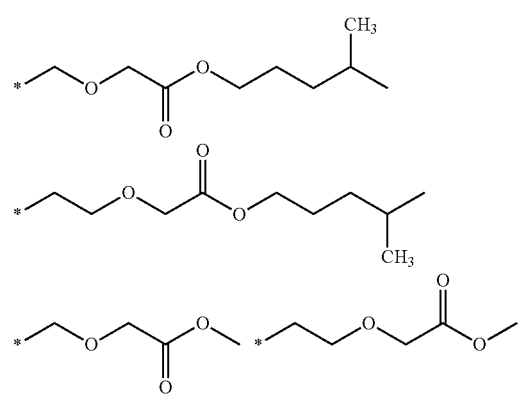

Examples of the group represented by the formula (L1-4) include the following ones.
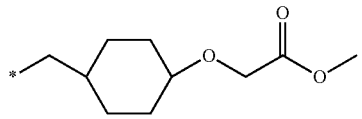
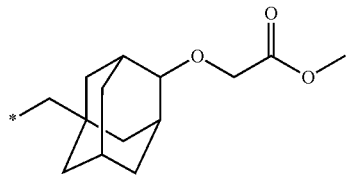
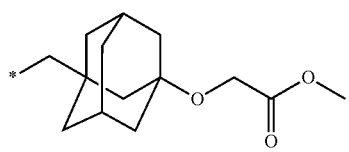
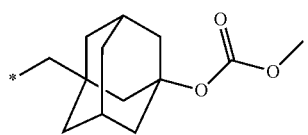
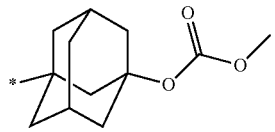
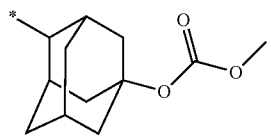
$L^{51}$ is preferably a single bond, a C1 to C8 divalent saturated hydrocarbon group or the group represented by the formula (L1-1), more preferably a single bond or the group represented by the formula (L1-1).
Examples of the structural unit represented by formula (a5-1) include the following ones.
(a5-1-1)
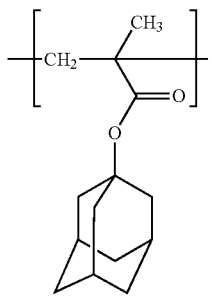
(a5-1-2)
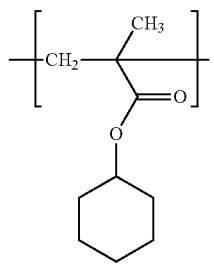
(a5-1-3)
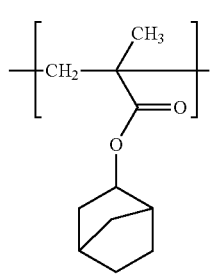
(a5-1-4)
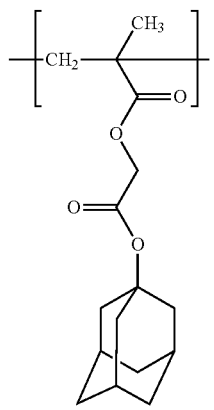
(a5-1-5)
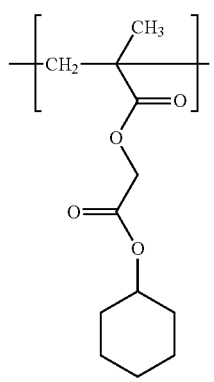

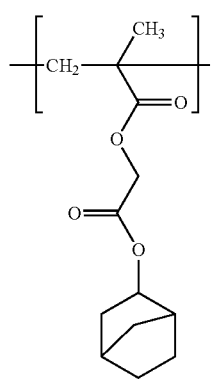 (a5-1-6)
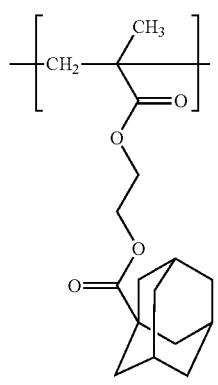 (a5-1-7)
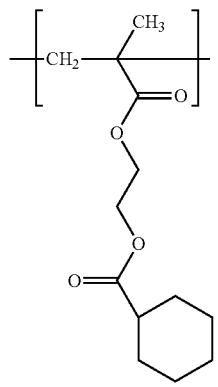 (a5-1-8)
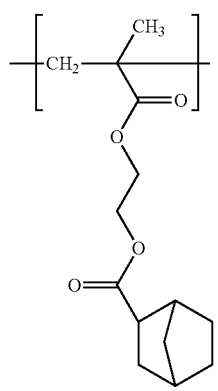 (a5-1-9)
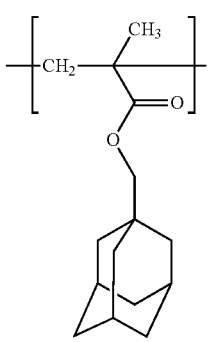 (a5-1-19)
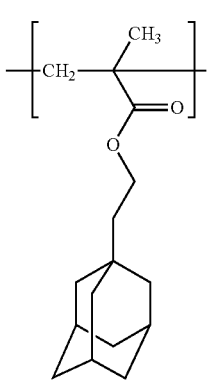 (a5-1-20)
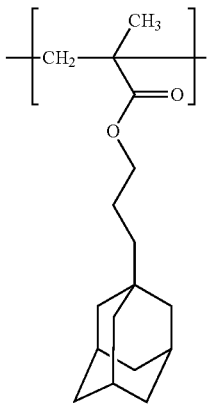 (a5-1-21)
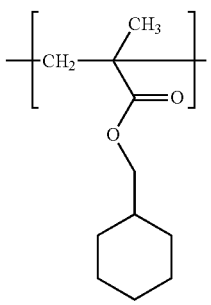 (a5-1-22)

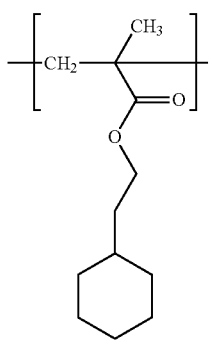
(a5-1-23)

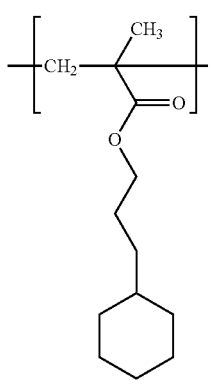
(a5-1-24)

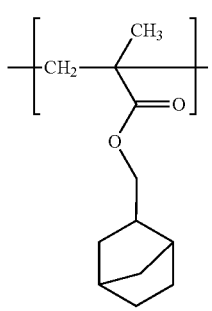
(a5-1-25)

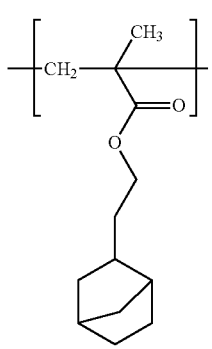
(a5-1-26)

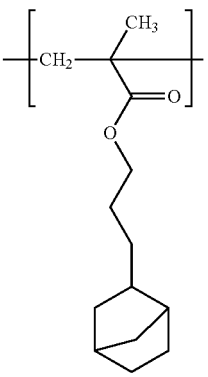
(a5-1-27)

Examples of the structural units represented by formula (a5-1) include structural units represented by the above formulae in which a methyl group corresponding to $R^{51}$ has been replaced by a hydrogen atom.

When the resin (A) further has the structural unit represented by formula (a5), the content thereof is preferably 1 to 30% by mole, more preferably 2 to 20% by mole, and still more preferably 3 to 15% by mole, based on all the structural units of the resin. Resin (A) has preferably the structural unit (a1) and the structural unit (s), more preferably the structural unit (a1) and the structural unit (a2-A). Preferably, Resin (A) consists of the structural units (a1) and (s), or the structural unit (a1), (s), (t) and (II).

In resin (A), the structural unit (a1) is one of the structural unit (a1-1) and the structural unit (a1-2), more preferably the structural unit (a1-2). The structural unit (a1-2) preferably comprises a cyclohexyl group or a cyclopentyl group.

The structural unit having no acid-labile group is preferably one of the structural unit (a2-A), the structural unit (a2) and the structural unit (a3). The structural unit (a2) is preferably the structural unit (a2-1). The structural unit (a3) is preferably one of the structural unit (a3-1), the structural unit (a3-2) and the structural unit (a3-4). The structural unit (a2-A) is preferably one derived from styrene.

Resin (A) has preferably the structural unit (a1-1). The content of the structural unit (a1-1) is preferably 15% by mole or more of the total amount of the structural unit (a1). The more is the structural unit having an adamantyl group, the more improved is the resistance of the photoresist film to dry etching.

Resin (A) can be produced according to known polymerization methods such as radical polymerization, using monomers corresponding to the structural units as mentioned above.

The resin has usually 2,000 or more of the weight-average molecular weight, preferably 2,500 or more of the weight-average molecular weight, more preferably 3,000 or more of the weight-average molecular weight. The resin has usually 50,000 or less of the weight-average molecular weight, preferably more 30,000 or less of the weight-average molecular weight, and preferably more 15,000 or less of the weight-average molecular weight.

The weight-average molecular weight can be measured with gel permeation chromatography.

The photoresist composition of the disclosure may further contain another resin than Resin (A).

Examples of another resin than Resin (A) include what consists of structural units having no acid-labile group, preferably what comprises, not the structural unit (a1), but the structural unit (a4). Here, another resin than Resin (A) is sometimes referred to as "Resin (X)".

Resin (X) may be one which consists of the structural unit (a4), or one which further has the structural unit (a2), the structural unit (a3) or another structural unit having no acid-labile group, known in the art.

In Resin (X), the content of the structural unit (a4) is preferably 40% by mole or more, more preferably 45% by mole or more, still more preferably 50% by mole or more, based on all the structural units of the resin.

Resin (X) usually has 6000 or more of the weight-average molecular weight, preferably 7000 or more of the weight-average molecular weight, more preferably 8000 or more of the weight-average molecular weight. The resin usually has 80,000 or less of the weight-average molecular weight, preferably has 60,000 or less of the weight-average molecular weight.

The weight-average molecular weight can be measured with known methods such as liquid chromatography or gas chromatography.

Resin (X) can be produced according to known polymerization methods such as radical polymerization, using monomers corresponding to the structural units as mentioned above.

When the photoresist composition contains Resin (X), the content of the resin is preferably 1 to 60 weight parts, more preferably 2 to 50 weight parts, and still more preferably 2 to 40 weight parts, and further still more preferably 3 to 30 weight parts, relative to 100 parts of Resin (A).

The total content of the resins in the photoresist composition is usually 80% by mass or more based on sum of the solid components, and usually 99% by mass or less.

In this specification, "solid component" means components other than solvent in the photoresist composition.

The photoresist composition of the disclosure may further contain a solvent.

The amount of the solvent is usually 90% by weight or more, preferably 92% by weight or more preferably 94% by weight or more based on total amount of the photoresist composition. The amount of the solvent is usually 99.9% by weight or less and preferably 99% by weight or less based on total amount of the photoresist composition. The content can be measured with known methods such as liquid chromatography or gas chromatography.

Examples of the solvent include a glycol ether ester such as ethyl cellosolve acetate, methyl cellosolve acetate and propylene glycol monomethyl ether acetate; a glycol ether such as propylene glycol monomethyl ether; an ester such as ethyl lactate, butyl acetate, amyl acetate and ethyl pyruvate; a ketone such as acetone, methyl isobutyl ketone, 2-heptanone and cyclohexanone; and a cyclic ester such as γ-butyrolactone.

The photoresist compositions of the disclosure may further contain a quencher. The "quencher" has the property that it can trap an acid, especially an acid generated from the acid generator by applying a radiation.

Examples of the quencher include a basic nitrogen-containing organic compound and a weak acid salt.

Examples of the basic nitrogen-containing organic compound include an amine compound such as an aliphatic amine, an aromatic amine and an ammonium salt. Examples of the aliphatic amine include a primary amine, a secondary amine and a tertiary amine. Examples of the aromatic amine include an aromatic amine in which an aromatic ring has an amino group such as aniline and a heteroaromatic amine such as pyridine.

Examples of the quencher include 1-naphthylamine, 2-naphthylamine, aniline, diisopropylaniline, 2-, 3- or 4-methylaniline, 4-nitroaniline, N-methylaniline, N,N-dimethylaniline, diphenylamine, hexylamine, heptylamine, octylamine, nonylamine, decylamine, dibutylamine, pentylamine, dioctylamine, triethylamine, trimethylamine, tripropylamine, tributylamine, tripentylamine, trihexylamine, triheptylamine, trioctylamine, trinonylamine, tridecylamine, methyldibutylamine, methyldipentylamine, methyldihexylamine, methyldicyclohexylamine, methyldiheptylamine, methyldioctylamine, methyldinonylamine, methyldidecylamine, ethyldibutylamine, ethyldipentylamine, ethyldihexylamine, ethyldiheptylamine, ethyldioctylamine, ethyldinonylamine, ethyldidecylamine, dicyclohexylmethylamine, 2-tris[2-(2-methoxyethoxy)ethyl]amine, triisopropanolamine, ethylenediamine, tetramethylenediamine, hexamethylenediamine, 4,4'-diamino-1,2-diphenylethane, 4,4'-diamino-3,3'-dimethyldiphenylmethane, 4,4'-diamino-3,3'-diethyldiphenyl methane, piperazine, morpholine, piperidine, hindered amine compound having a piperidine structure, 2,2'-methylenebisaniline, imidazole, 4-methylimidazole, pyridine, 4-methylpyridine, 1,2-di(2-pyridyl)ethane, 1,2-di(4-pyridyl)ethane, 1,2-di(2-pyridyl)ethene, 1,2-di(4-pyridyl)ethene, 1,3-di(4-pyridyl) propane, 1,2-di(4-pyridyloxy)ethane, di(2-pyridyl)ketone, 4,4'-dipyridyl sulfide, 4,4'-dipyridyl disulfide, 2,2'-dipyridylamine, 2,2'-dipicolylamine and bipyridine.

Examples of the quaternary ammonium salts include tetramethylammonium hydroxide, tetrabutylammonium hydroxide, tetrahexylammonium hydroxide, tetraoctylammonium hydroxide, phenyltrimethylammonium hydroxide, (3-trifluoromethylphenyl)trimethylammonium hydroxide and (2-hydroxyethyl)trimethylammonium hydroxide (so-called "choline").

The weak acid salt is usually lower in acidity than the acid generator as mentioned above and Salt (I), examples of which include carboxylic acid salts and sulfonic acid salts.

The acidity in the weak acid salt is shown by the acid dissociation constant (pKa).

The acid dissociation constant of acid generated from the weak acid salt is usually −3<pKa.

The weak acid salt is preferably a salt of −1<pKa<7, and more preferably a salt of 0<pKa<5.

Specific examples of the weak acid salt include JP2012-229206A1, JP2012-6908A1, JP2011-191745A1, JP2012-72109A1, JP2011-39502A1 and the following ones.

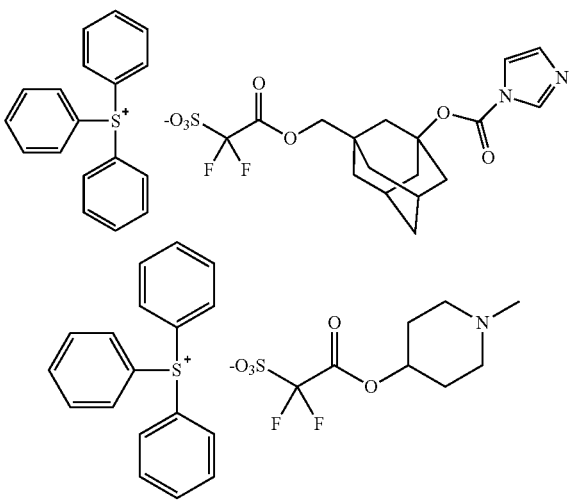

-continued

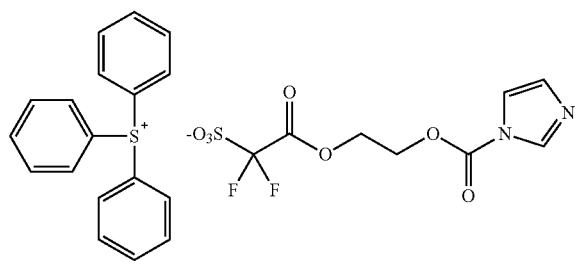
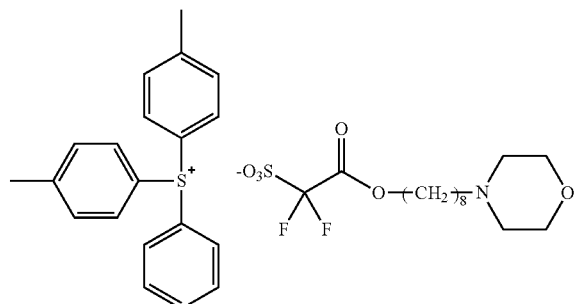
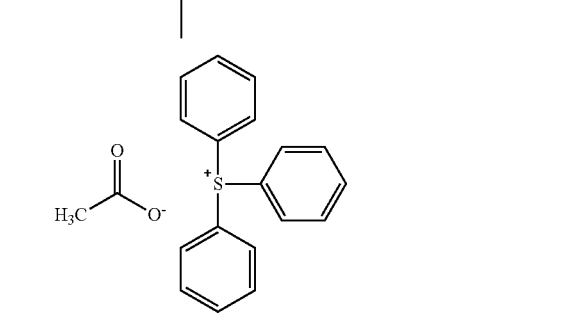
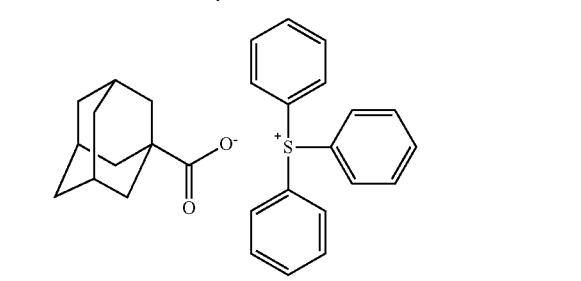
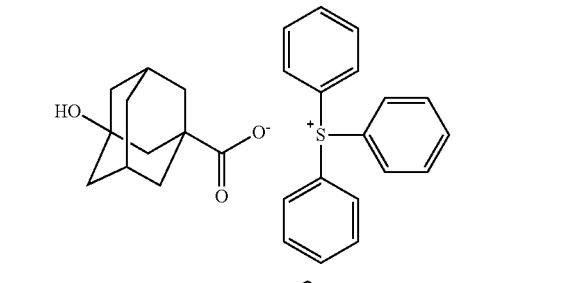
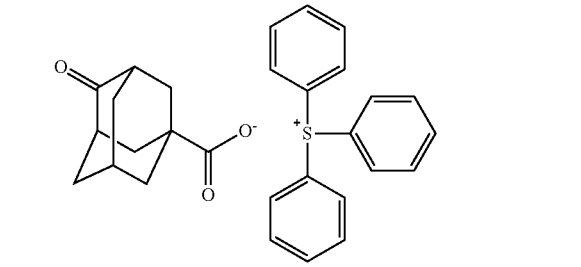

-continued

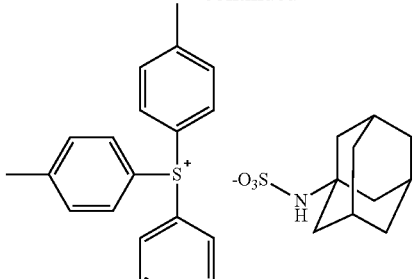
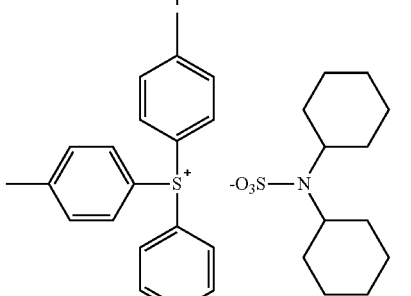
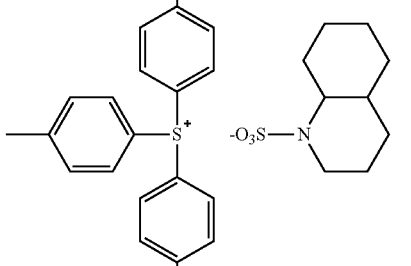

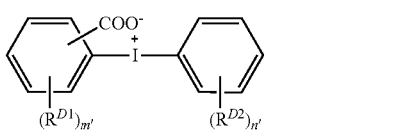

(D)

In the formula (D), $R^{D1}$ and $R^{D2}$ in each occurrence independently represent a C1 to C12 hydrocarbon group, a C1 to C6 alkoxyl group, a C2 to C7 acyl group, a C2 to C7 acyloxy group, a C2 to C7 alkoxycarbonyl group, a nitro group or a halogen atom;

m' and n' each independently represent an integer of 0 to 4.

Examples of the hydrocarbon group for $R^{D1}$ and $R^{D2}$ include any of an aliphatic hydrocarbon group, an alicyclic hydrocarbon group, an aromatic hydrocarbon group and a combination thereof. Examples of the aliphatic hydrocarbon group include an alkyl group suchasmethyl, ethyl, propyl, isopropyl, butyl, isobutyl, tert-butyl, pentyl, hexyl and nonyl groups.

The alicyclic hydrocarbon group is any one of monocyclic or polycyclic hydrocarbon group, and saturated or unsaturated hydrocarbon group.

Examples thereof include a cycloalkyl group such as cyclopropyl, cyclobutyl, cyclopentyl, cyclohexyl, cyclononyl and cyclododecyl groups; and polycyclic groups such as adamantyl and norbornyl groups. Examples of the aromatic hydrocarbon group include an aryl group such as phenyl, 1-naphthyl, 2-naphthyl, 2-methylphenyl, 3-methylphenyl, 4-methylphenyl, 4-ethylphenyl, 4-propylphenyl, 4-isopropylphenyl, 4-butylphenyl, 4-tert-butylphenyl, 4-hexylphenyl, 4-cyclohexylphenyl, anthryl, p-adamantylphenyl, tolyl, xylyl, cumenyl, mesityl, biphenyl, phenanthryl, 2,6-diethylphenyl and 2-methyl-6-ethylphenyl groups.

Examples of the combination thereof include an alkylcycloalkyl, a cycloalkyl-alkyl, aralkyl (e.g., phenylmethyl, 1-phenylethyl, 2-phenylethyl, 1-phenyl-1-propyl, 1-phenyl-2-propyl, 2-phenyl-2-propyl, 3-phenyl-1-propyl, 4-phenyl-1-butyl, 5-phenyl-1-pentyl and 6-phenyl-1-hexyl groups) groups.

Examples of the alkoxyl group include methoxy and ethoxy groups. Examples of the acyl group include acetyl, propanoyl, benzoyl and cyclohexanecarbonyl groups.

Examples of the acyloxy group include a group in which oxy group (—O—) bonds to an acyl group.

Examples of the alkoxycarbonyl group include a group in which the carbonyl group (—CO—) bonds to the alkoxy group.

Example of the halogen atom is a chlorine atom, a fluorine atom and bromine atom.

In the formula (D), $R^{D1}$ and $R^{D2}$ in each occurrence independently preferably represent a C1 to C8 alkyl group, a C3 to C10 cycloalkyl group, a C1 to C6 alkoxyl group, a C2 to C4 acyl group, a C2 to C4 acyloxy group, a C2 to C4 alkoxycarbonyl group, a nitro group or a halogen atom.

m' and n' independently preferably represent an integer of 0 to 3, more preferably an integer of 0 to 2, and more preferably 0. Specific examples of the salt of the formula (D) include compounds below.

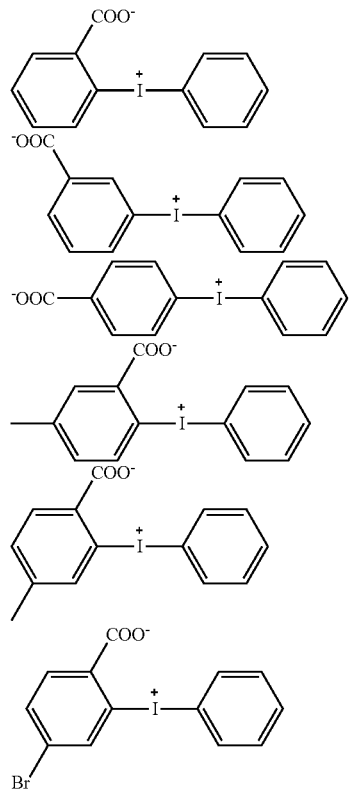

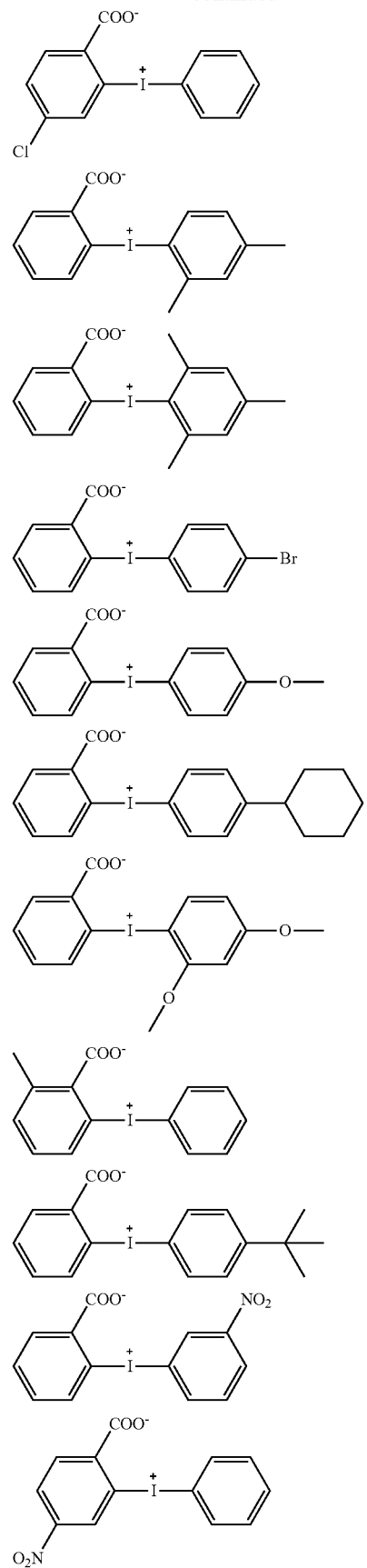

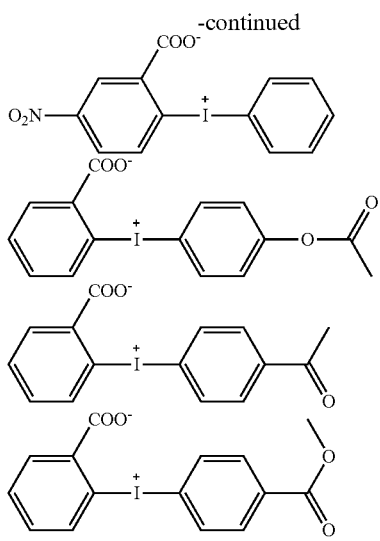

The content of quencher is preferably 0.01 to 5% by mass, more preferably 0.01 to 4% by mass, and still more preferably 0.01 to 3% by mass, based on sum of the solid components.

The photoresist compositions of the disclosure may further contain, if necessary, a small amount of various additives known in the art such as a sensitizer, a dissolution inhibitor, other polymers, a surfactant, a stabilizer and a dye.

The photoresist compositions of the disclosure can usually be prepared by mixing, in a solvent, Salt (I) and Resin (A), and if necessary a known acid generator, a quencher, and/or additives at a suitable ratio for the composition, optionally followed by filtrating the mixture with a filter having 0.003 µm to 0.2 µm of a pore size.

The order of mixing these components is not limited to any specific order. The temperature at mixing the components is usually 10 to 40° C., which can be selected in view of the resin or the like. The mixing time is usually 0.5 to 24 hours, which can be selected in view of the temperature. The means for mixing the components is not limited to specific one. The components can be mixed by being stirred.

The amounts of the components in the photoresist compositions can be adjusted by selecting the amount to be used for production of them.

The photoresist compositions of the disclosure are useful for a chemically amplified photoresist composition.

A photoresist pattern can be produced by the following steps (1) to (5)

(1) a step of applying the photoresist composition of the disclosure on a substrate, (2) a step of forming a composition film by conducting drying, (3) a step of exposing the composition film to radiation, (4) a step of baking the exposed composition film, and (5) a step of developing the baked composition film with an alkaline developer.

The applying of the photoresist composition on a substrate is usually conducted using a conventional apparatus such as spin coater. The photoresist composition is preferably filtrated with filter having a pore size of 0.01 to 0.2 µm before applying. Examples of the substrate include a silicon wafer or a quartz wafer on which a sensor, a circuit, a transistor or the like is formed.

The formation of the composition film is usually conducted using a heating apparatus such as hot plate or a decompressor, and the heating temperature is usually 50 to 200° C. When the pressure is reduced during heating, the operation pressure is usually 1 to $1.0*10^5$ Pa. The heating time is usually 10 to 180 seconds.

The composition film obtained is exposed to radiation using an exposure system. The exposure is usually conducted through a mask having a pattern corresponding to the desired photoresist pattern. Examples of the exposure source include a light source radiating laser light in a UV-region such as a KrF excimer laser (wavelength: 248 nm), an ArF excimer laser (wavelength: 193 nm) and a $F_2$ laser (wavelength: 157 nm), and a light source radiating harmonic laser light in a far UV region or a vacuum UV region by wavelength conversion of laser light from a solid laser light source (such as YAG or semiconductor laser)

The temperature of baking of the exposed composition film is usually 50 to 200° C., and preferably 70 to 150° C.

The development of the baked composition film is usually carried out using a development apparatus. The development method includes dipping methods, paddle methods, spray methods and dynamic dispense method. The developing temperature is preferably 5 to 60° C., and the developing time is preferably 5 to 300 seconds. The positive and negative type photoresist patterns can be obtained by the development depending on a developer to be used therefor. When a positive type photoresist pattern is prepared from the photoresist composition of the disclosure, the development can be conducted with an alkaline developer. The alkaline developer to be used may be any one of various aqueous alkaline solution used in the art. Generally, an aqueous solution of tetramethylammonium hydroxide or (2-hydroxyethyl)trimethylammonium hydroxide (commonly known as "choline") is often used. The alkaline developer may contain a surfactant.

After development, the photoresist film having photoresist pattern is preferably washed with ultrapure water, and the remained water on the photoresist film and the substrate is preferably removed therefrom.

When a negative type photoresist pattern is prepared from the photoresist composition of the disclosure, the development can be conducted with a developer containing an organic solvent, such developer is sometimes referred to as "organic developer". Examples of an organic solvent for organic developer include ketone solvents such as 2-hexanone, 2-heptanone; glycolether ester solvents such as propyleneglycolmonomethylether acetate; ester solvents such as butyl acetate; glycolether solvents such as propyleneglycolmonomethylether; amide solvents such as N,N-dimethylacetamide; and aromatic hydrocarbon solvents such as anisole.

The content of organic solvent is preferably from 90% to 100% by weight, more preferably from 95% to 100% by weight, in an organic developer. Preferred is that the organic developer essentially consists of an organic solvent.

Among them, the organic developer is preferably a developer comprising butyl acetate and/or 2-heptanone.

The total content of butyl acetate and 2-heptanone is preferably from 50% to 100% by weight, more preferably from 90% to 100% by weight. Preferred is that the organic developer essentially consists of butyl acetate and/or 2-heptanone.

The organic developer may comprise a surfactant or a very small amount of water.

Development with an organic developer can be stopped by replacing the developer by other solvent than it such as alcohol.

The photoresist composition of the disclosure is suitable for KrF excimer laser lithography, ArF excimer laser lithography, EUV (extreme ultraviolet) lithography and EB (electron beam) lithography, particularly for EUV (extreme ultraviolet) lithography and EB (electron beam) lithography.

EXAMPLES

The invention as mentioned above will be described more specifically by Examples which are not construed to limit the scope of the disclosure.

The "%" and "part(s)" used to represent the content of any component and the amount of any material used in the following examples and comparative examples are on a mass basis unless otherwise specifically noted.

The weight-average molecular weight of any material used in the following examples is determined with gel permeation chromatography under the following condition.

Equipment: HLC-8120 GCP type, manufactured by TOSOH CORPORATION
Column: Three of TSKgel Multipore $H_{XL}$-M with guard-column, manufactured by TOSOH CORPORATION
Solvent: tetrahydrofuran
Flow rate: 1.0 mL/min.
Detector: RI Detector
Column temperature: 40° C.
Injection volume: 100 μL
Standard reference material: Standard polystyrene (manufactured by TOSOH CORPORATION)
Structures of compounds were determined by mass spectrometry (Liquid Chromatography: 1100 Type, manufactured by AGILENT TECHNOLOGIES LTD., Mass Spectrometry: LC/MSD Type, manufactured by AGILENT TECHNOLOGIES LTD.).
Here, the values at the peaks of spectrum are referred to as "MASS."

Example 1

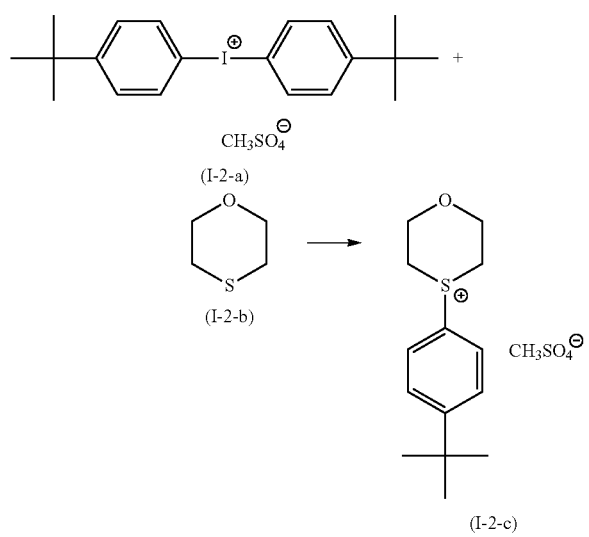

To a reactor, 50 parts of the compound represented by the formula (I-2-a), 10.33 parts of the compound represented by the formula (I-2-b) and 350 parts of chloroform were added and then they were stirred at 23° C. for 30 minutes.

To the resulting mixture, 0.2 parts of copper (II) dibenzoate was added and refluxed at 80° C. for 2 hours, followed by being concentrated.

To the obtained concentrate, 440 parts of tert-butylmethylether were added and the obtained mixture was stirred, followed by being filtrated to obtain 32.96 parts of the compound represented by the formula (I-2-c).

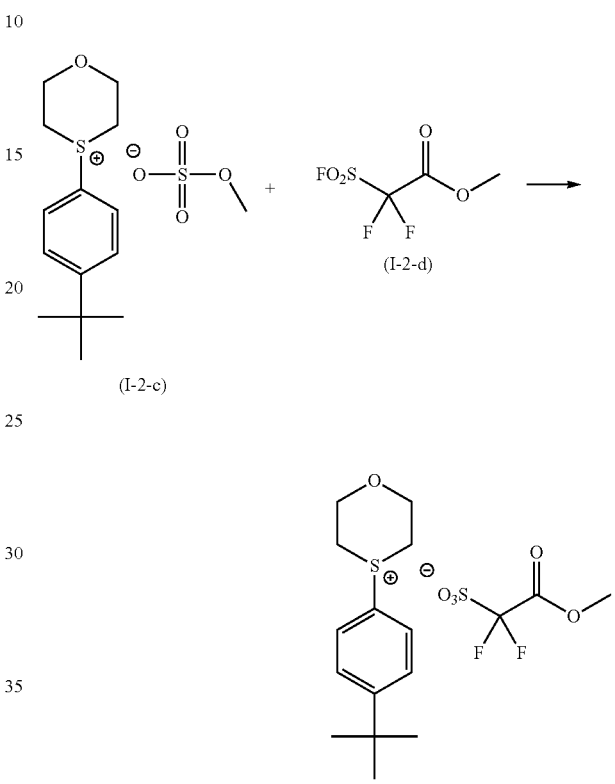

5.68 parts of the compound represented by the formula (I-2-c), 57.1 parts of chloroform, 19.9 parts of ion-exchanged water and 3.02 parts of triethylamine were added to a reactor and then stirred at 23° C. for 30 minutes, followed by being cooled to 5° C.

To the obtained mixture, a mixed solution of 2.61 parts of the compound represented by the formula (I-2-d) and 2.61 parts of chloroform was dropped for 30 minutes, and stirred at 23° C. for one hour, followed by separating an organic layer.

To the collected organic layer, 33 parts of 5% aqueous oxalic acid solution was added, and then stirred at 23° C. for 30 minutes, followed by separating an organic layer. This washing step was conducted three times. To the obtained organic layer, 33 parts of ion-exchanged water was added and stirred at 23° C. for 30 minutes, followed by separating an organic layer. The washing step with water was conducted three times. The washed organic layer was concentrated to obtain 3.66 parts of the compound represented by formula (I-2-e).

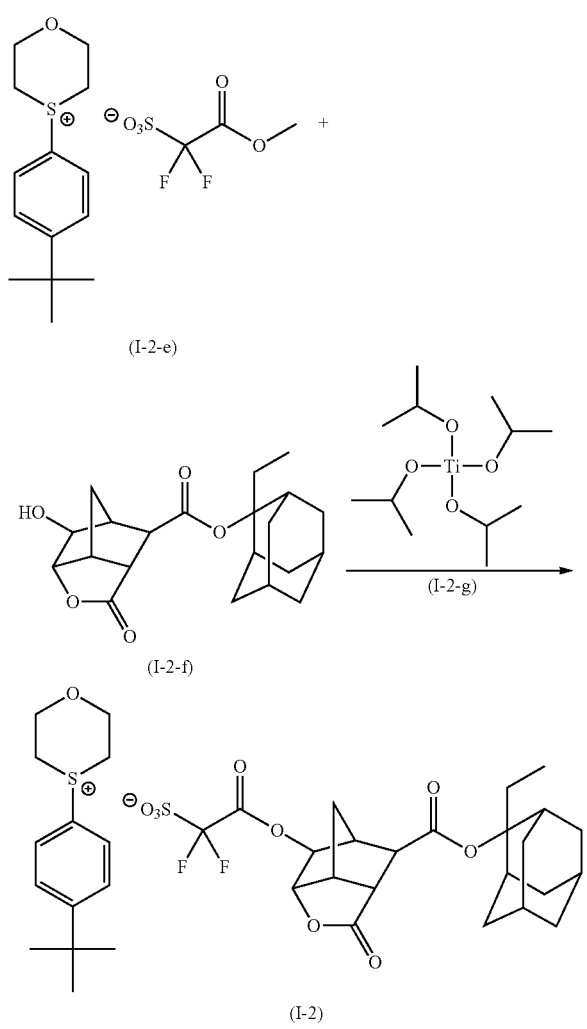

(I-2-e)

(I-2-f)

(I-2-g)

(I-2)

Into the reactor, 3.33 parts of the compound represented by the formula (I-2-e), 4.15 parts of the compound represented by the formula (I-2-f), 50 parts of chloroform and 0.67 parts of the compound represented by the formula (I-2-g) were fed and then stirred at 23° C. for 34 hours. Then the obtained reaction mixture was filtrated and then the filtrated solution was concentrated. To the obtained residue, 50 parts of tert-butylmethylether were added and then stirred at 23° C. for 30 minutes. Then obtained mixture was filtrated to obtain 4.82 parts of the salt represented by the formula (I-2).

MASS (ESI (+) Spectrum): M$^+$237.1
MASS (ESI (−) Spectrum): M$^-$ 517.1

Example 2

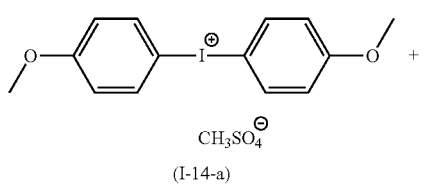

(I-14-a)

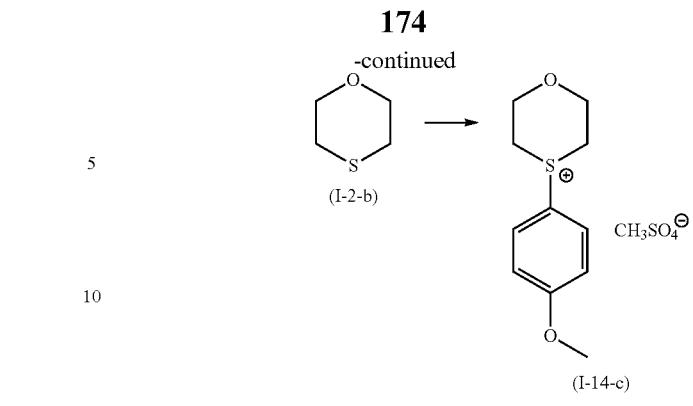

(I-2-b)

(I-14-c)

To a reactor, 45 parts of the compound represented by the formula (I-14-a), 10.33 parts of the compound represented by the formula (I-2-b) and 350 parts of chloroform were added and then they were stirred at 23° C. for 30 minutes.

To the resulting mixture, 0.2 parts of copper (II) dibenzoate was added and refluxed at 80° C. for 2 hours, followed by being concentrated.

To the obtained concentrate, 440 parts of tert-butylmethylether were added and the obtained mixture was stirred, followed by being filtrated to obtain 25.44 parts of the compound represented by the formula (I-14-c).

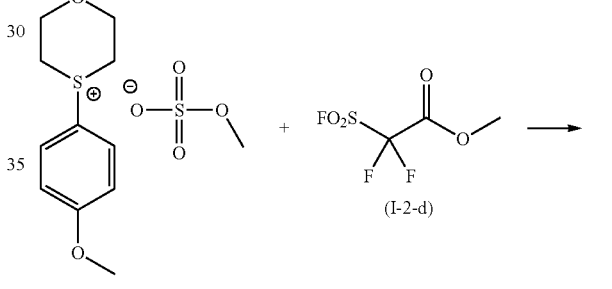

(I-14-c)  (I-2-d)

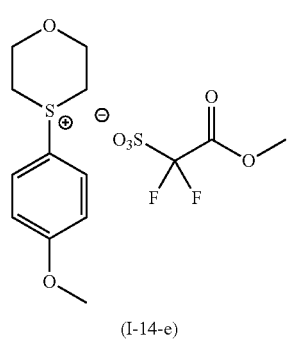

(I-14-e)

5.25 parts of the compound represented by the formula (I-14-c), 57.1 parts of chloroform, 19.9 parts of ion-exchanged water and 3.02 parts of triethylamine were added to a reactor and then stirred at 23° C. for 30 minutes, followed by being cooled to 5° C.

To the obtained mixture, a mixed solution of 2.61 parts of the compound represented by the formula (I-2-d) and 2.61 parts of chloroform was dropped for 30 minutes, and stirred at 23° C. for one hour, followed by separating an organic layer.

To the collected organic layer, 33 parts of 5% aqueous oxalic acid solution was added, and then stirred at 23° C. for 30 minutes, followed by separating an organic layer. To the obtained organic layer, 33 parts of ion-exchanged water was added and then stirred at 23° C. for 30 minutes, followed by separating an organic layer. The washing step with water was conducted three times. The washed organic layer was concentrated to obtain 3.21 parts of the compound represented by formula (I-14-e)

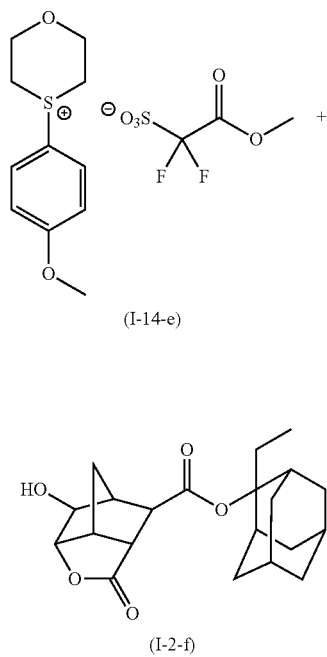

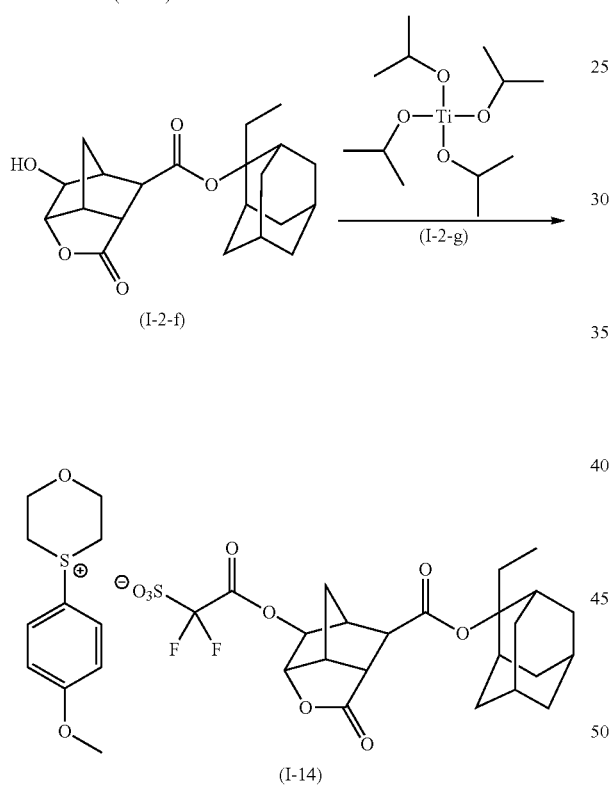

Into the reactor, 3.13 parts of the compound represented by the formula (I-14-e), 4.15 parts of the compound represented by the formula (I-2-f), 50 parts of chloroform and 0.67 parts of the compound represented by the formula (I-2-g) were fed and then stirred at 23° C. for 34 hours. Then the obtained reaction mixture was filtrated, and then the filtrated solution was concentrated. To the obtained residue, 50 parts of tert-butylmethylether were added and then stirred at 23° C. for 30 minutes. Then obtained mixture was filtrated to obtain 3.22 parts of the salt represented by the formula (I-14).

MASS (ESI (+) Spectrum): $M^+$ 211.1
MASS (ESI (−) Spectrum): $M^-$ 517.1

Synthesis Example 1

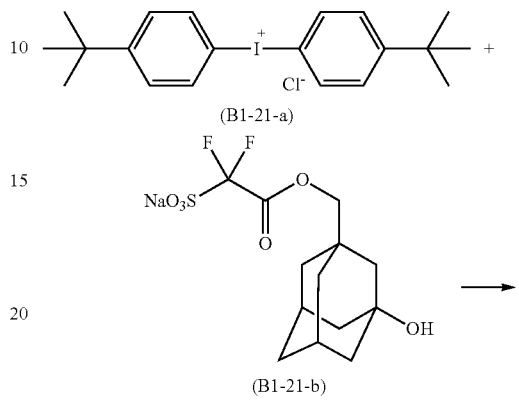

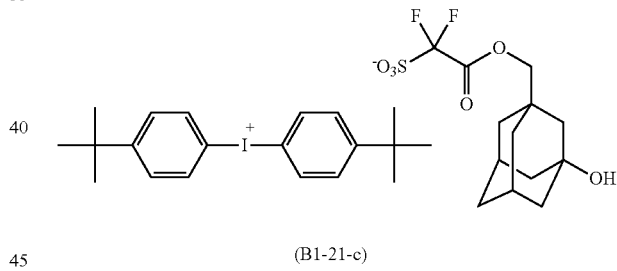

In a reactor, 30.00 parts of the salt represented by the formula (B1-21-b) which had been produced according to the method described in JP 2008-209917 A, 35.50 parts of the salt represented by the formula (31-21-a), 100 parts of chloroform and 50 parts of ion-exchanged water were fed and stirred at 23° C. for 15 hours. From the obtained reaction mixture which had two phases, a chloroform phase was collected with separation.

The chloroform phase was washed with 30 parts of ion-exchanged water for washing: This washing was conducted five times.

The washed chloroform phase was concentrated. To the obtained residue, 100 parts of tert-butylmethylether was added and then stirred at 23° C. for 30 minutes, followed by being filtrated to obtain 48.57 parts of the salt represented by the formula (B1-21-c).

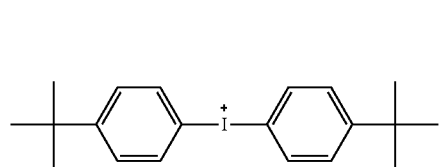
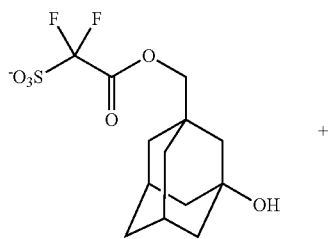

(B1-21-c)

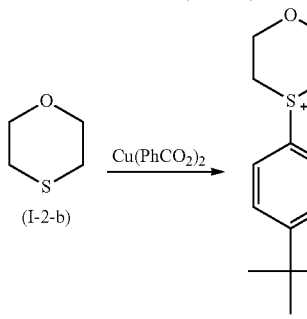
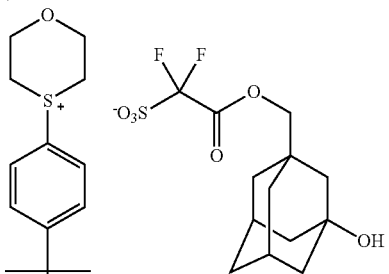

(I-2-b) → (B1-21)

Into a reactor, 20.00 parts of the salt represented by the formula (B1-21-c), 2.84 parts of the compound represented by the formula (I-2-b) and 250 parts of monochlorobenzene were fed and then they were stirred at 23° C. for 30 minutes.

To the resultant mixture, 0.21 part of copper (II) dibenzoate was added. The resultant mixture was stirred at 100° C. for 1 hour. The mixture was concentrated, and then 200 parts of chloroform and 50 parts of ion-exchanged water were added to the obtained residue, followed by being stirred at 23° C. for 30 minutes. Then the organic phase was collected by separation. Then 50 parts of ion-exchanged water was added to the organic layer and stirred at 23° C. for 30 minutes, followed by collecting an organic phase by separation: This washing was conducted five times.

The washed organic layer was concentrated. To the residue, 53.51 parts of acetonitrile was added, and the resultant mixture was concentrated. To the residue, 113.05 parts of tert-butylmethylether was added and then they were stirred, followed by being filtrated to obtain 10.47 parts of the salt represented by the formula (B1-21).

MS (ESI(+) Spectrum): M$^+$ 237.1

MS (ESI(−) Spectrum): M$^−$ 339.1

Compounds used as monomers in the following Synthesis Examples are shown as follow.

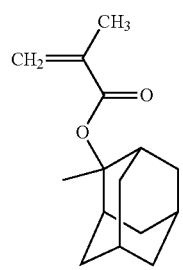

(a1-1-1)

-continued

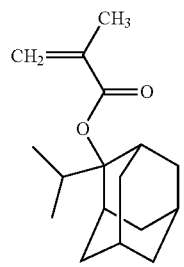

(a1-1-3)

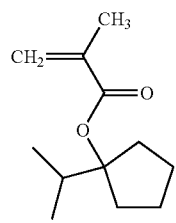

(a1-2-11)

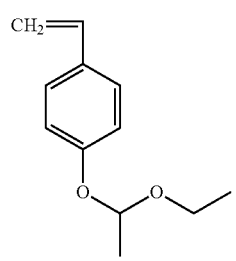

(a1-4-2)

-continued (a2-1-1)
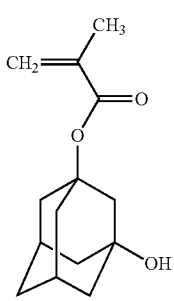

(a3-1-1)
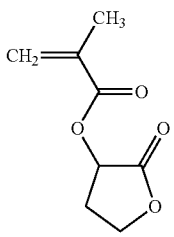

(a3-2-1)
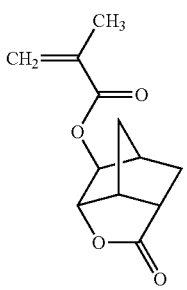

(a2-2-1)
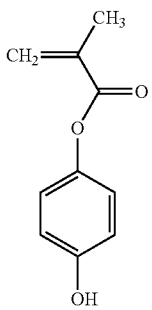

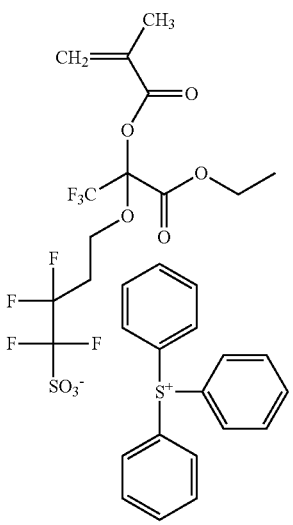

-continued (a7-1)
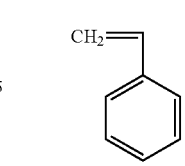

Here, each of the compounds is referred as to "monomer (X)" where "X" is the symbol of the formula representing the monomer.

Synthesis Example 2

Monomers (a1-4-2), (a1-1-1), (a2-1-1), (a7-1) and (a3-1-1) were mixed in the molar ratio of 40/30/5/5/20 (monomer (a1-4-2)/monomer (a1-1-1)/monomer (a2-1-1)/monomer (a7-1)/monomer (a3-1-1)) and propyleneglycolmonomethylether acetate was added thereto in 1.5 parts by weight relative to all monomers to prepare a mixture. To the mixture, azobisisobutyronitrile and azobis(2,4-dimethylvaleronitrile) were added as initiators in the ratio of 1.2% by mole and 3.6% by mole based on molar amounts of all the monomers, and the obtained mixture was heated at 75° C. for about 5 hours. The reaction mixture was poured into a large amount of a mixture of methanol and water to cause precipitation. The precipitate was collected by filtration. The obtained precipitate was dissolved in propyleneglycolmonomethyletheracetate, and aqueous p-toluenesulfonic acid solution was added thereto and then stirred for about 6 hours. Then the obtained mixture was separated to collect an organic layer.

The collected organic layer was poured into a large amount of a mixture of methanol and water to cause precipitation, followed by being filtrated to obtain a resin having a weight-average molecular weight of about $5.9 \times 10^3$ in yield of 61%. This resin is referred to as Resin A1. Resin A1 had the following structural units.

(II-2-A-1-1)
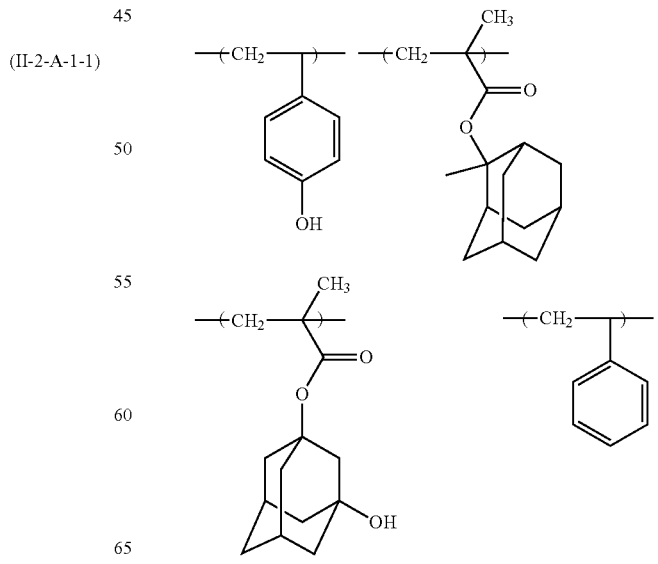

-continued

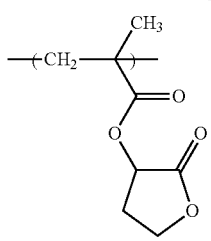

Synthesis Example 3

Monomers (a2-2-1), (a1-1-3), (a2-1-11), (a3-2-1), (a7-1) and (II-2-A-1-1) were mixed in the molar ratio of 10/35/15/30/5/5 (monomer (a2-2-1)/monomer (a1-1-3)/monomer (a2-1-11)/monomer (a3-2-1)/monomer (a7-1)/monomer (II-2-A-1-1)), and methylethylketone was added thereto in 1.5 parts by weight relative to all monomers to prepare a mixture. To the mixture, azobisisobutyronitrile and azobis(2,4-dimethylvaleronitrile) were added as initiators in the ratio of 1.2% by mole and 3.6% by mole based on molar amounts of all the monomers, and the obtained mixture was heated at 75° C. for about 5 hours. The reaction mixture was poured into a large amount of n-heptane to cause precipitation. The precipitate was collected by filtration. The obtained precipitates were poured into a large amount of the mixture of n-heptane and isopropylalcohol (weight ratio of n-heptane/isopropylalcohol=1/4) to cause precipitation. Then the precipitates were filtrated to obtain a resin having a weight-average molecular weight of about $5.5 \times 10^3$ in yield of 45%. This resin is referred to as Resin A2. Resin A2 had the following structural units.

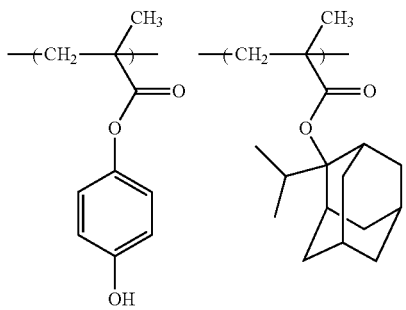

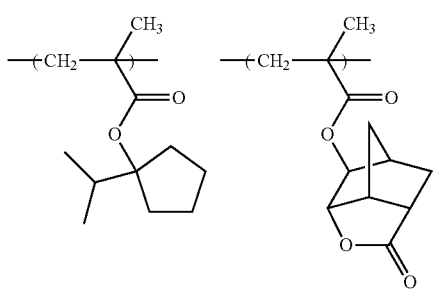

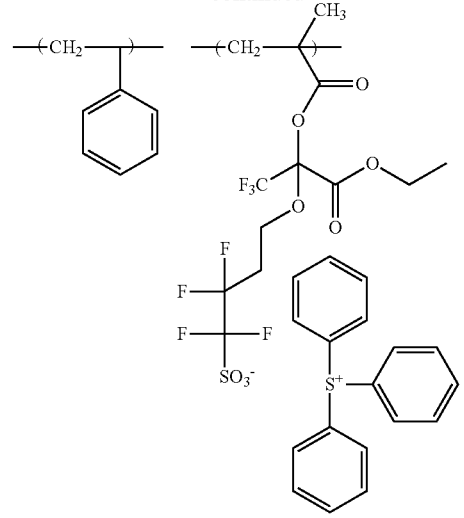

Examples 3 to 12 and Comparative Examples 1 to 5

Production of Photoresist Compositions

The following components as listed in Table 1 were mixed and dissolved in the solvent as mentioned below, and then filtrated through a fluorine resin filter having pore diameter of 0.2 μm, to prepare photoresist compositions.

TABLE 1

| Comp. No. | Resin (kind/ amount (part)) | Acid generator (kind/ amount (part)) | Quencher (kind/ amount (part)) | PB(° C.)/ PEB(° C.) |
|---|---|---|---|---|
| Comp. 1 | A1/10 | I-2/3 | C1/0.3 | 110/110 |
| Comp. 2 | A1/10 | I-2/4 | C1/0.3 | 110/110 |
| Comp. 3 | A1/10 | I-2/4.5 | C1/0.3 | 110/110 |
| Comp. 4 | A1/10 | I-2/3 B1-25/1 | C1/0.3 | 110/110 |
| Comp. 5 | A2/10 | I-2/2 | C1/0.3 | 100/110 |
| Comp. 6 | A2/10 | I-2/2 | C2/0.3 | 100/110 |
| Comp. 7 | A2/10 | I-2/2 | C3/0.3 | 100/110 |
| Comp. 8 | A1/10 | I-2/4 | C3/0.3 | 100/110 |
| Comp. 9 | A1/10 | I-14/4 | C3/0.3 | 100/110 |
| Comp. 10 | A2/10 | I-14/2 | C3/0.3 | 100/110 |
| Compar. Comp. 1 | A1/10 | B1-X/3 | C1/0.3 | 110/110 |
| Compar. Comp. 2 | A1/10 | B1-X/4 | C1/0.3 | 110/110 |
| Compar. Comp. 3 | A1/10 | B1-21/3 | C1/0.3 | 110/110 |
| Compar. Comp. 4 | A1/10 | B1-21/4 | C1/0.3 | 110/110 |
| Compar. Comp. 5 | A1/10 | B1-25/3 | C1/0.3 | 110/110 |

In Table 1, symbols represent the following components.
<Resin>
A1: Resin A1, A2: Resin A2
<Acid Generator>
1-2: Salt represented by formula (1-2)
1-14: Salt represented by formula (1-14)
B1-21: Salt represented by formula (B1-21)
B1-25: Salt represented by formula (B1-25), produced by the method according to JP2011-126869A1.

(B1-25)

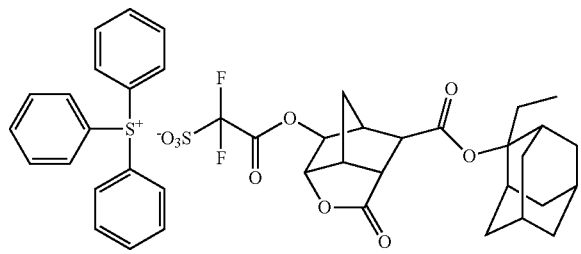

B1-X: Salt represented by formula (B1-X), produced by the method according to JP2011-126869A1.

(B1-X)

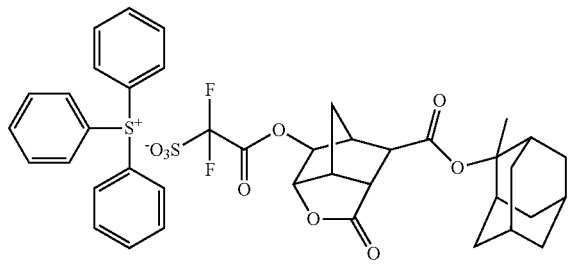

<Quencher>
C1: Tetra(n-butyl)ammonium salicylate, manufactured by Tokyo Chemical Industries, Co., Ltd.
C2: Diisopropylaniline, manufactured by Tokyo Chemical Industries, Co., Ltd.
C3: The compound of the following formula, produced by the method according to JP2011-039502A1.

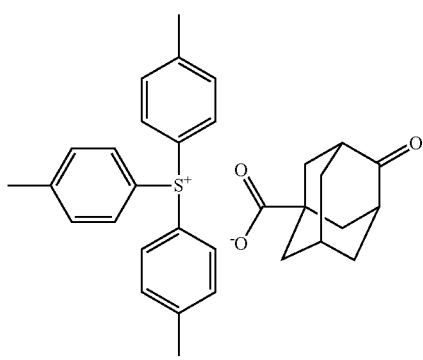

<Solvent>
E1: Mixture of the following ones

| | |
|---|---|
| propyleneglycolmonomethylether acetate | 400 parts |
| propyleneglycolmonomethylether | 100 parts |
| γ-butyrolactone | 5 parts |

<Evaluation Using EB Lithography>

Silicon wafers (6 inches) were treated with hexamethyldisilazane, by applying it on the wafers and then being baked at 90° C. for 60 seconds. One of the above-mentioned photoresist compositions was spin-coated over the treated wafer so that the thickness of the resulting film became 40 nm after drying. The silicon wafer thus coated with the photoresist composition was prebaked on a direct hotplate at a temperature shown in the column "PB" in Table 1 for 60 seconds.

Using an electron beam lithography device ("HL800D 50 keV" manufactured by Hitachi), each wafer thus formed with the respective composition film was subjected to exposure with the exposure quantity being varied stepwise to thereby form a line-and-space pattern. After the exposure, each wafer was subjected to post-exposure baking on a hotplate at a temperature shown in the column "PEB" in Table 1 for 60 seconds and then to development in the manner of paddle development for 60 seconds with 2.38% by weight of aqueous tetramethylammonium hydroxide solution to make a photoresist pattern.

Effective sensitivity was defined as the exposure quantity providing the pattern which has 60 nm of the line width with the ratio of width between the line and the space being 1:1 after exposure and development.

Line Edge Roughness (LER) Evaluation

The photoresist pattern which has 60 nm of the line width was obtained with exposure at the effective sensitivity, and checked irregularity in wall surface, using a scanning electron microscope.

Table 2 illustrates the results thereof. The figures in parentheses represent LER (nm).

TABLE 2

| Ex. No. | Composition | LER(nm) |
|---|---|---|
| Ex. 3 | Comp. 1 | 4.04 |
| Ex. 4 | Comp. 2 | 3.99 |
| Ex. 5 | Comp. 3 | 4.02 |
| Ex. 6 | Comp. 4 | 4.05 |
| Ex. 7 | Comp. 5 | 3.98 |
| Ex. 8 | Comp. 6 | 4.16 |
| Ex. 9 | Comp. 7 | 3.88 |
| Ex. 10 | Comp. 8 | 3.96 |
| Ex. 11 | Comp. 9 | 3.88 |
| Ex. 12 | Comp. 10 | 3.78 |
| Comparative Ex. 1 | Compar. Comp. 1 | 4.38 |
| Comparative Ex. 2 | Compar. Comp. 2 | 4.46 |
| Comparative Ex. 3 | Compar. Comp. 3 | 4.48 |
| Comparative Ex. 4 | Compar. Comp. 4 | 4.44 |
| Comparative Ex. 5 | Compar. Comp. 5 | 4.34 |

<Evaluation Using EUV Lithography>

Silicon wafers (8 inches) were treated with hexamethyldisilazane, by applying it on the wafers and then being baked at 90° C. for 60 seconds. One of the above-mentioned photoresist compositions was spin-coated over the treated wafer so that the thickness of the resulting film became 35 nm after drying. The silicon wafer thus coated with the photoresist composition was prebaked on a direct hotplate at a temperature shown in the column "PB" in Table 1 for 60 seconds.

Using an EUV lithography device, each wafer thus formed with the respective composition film was subjected to exposure with the exposure quantity being varied stepwise to thereby form a line-and-space pattern. After the exposure, each wafer was subjected to post-exposure baking on a hotplate at a temperature shown in the column "PEB" in Table 1 for 60 seconds and then to development in the manner of paddle development for 60 seconds with 2.38% by weight of aqueous tetramethylammonium hydroxide solution to make a photoresist pattern.

Effective sensitivity was defined as the exposure quantity providing the pattern which has 30 nm of the line width with the ratio of width between the line and the space being 1:1 after exposure and development.

Line Edge Roughness (LER) Evaluation

The photoresist pattern which has 30 nm of the line width was obtained with exposure at the effective sensitivity, and checked irregularity in wall surface, using a scanning electron microscope.

Table 3 illustrates the results thereof. The figures in parentheses represent LER (nm).

TABLE 3

| Ex. No. | Composition | LER(nm) |
|---------|-------------|---------|
| Ex. 13 | Comp. 2 | 2.22 |
| Ex. 14 | Comp. 5 | 2.21 |
| Ex. 15 | Comp. 7 | 2.18 |
| Ex. 16 | Comp. 9 | 2.13 |
| Ex. 17 | Comp. 10 | 2.08 |

The salt of the disclosure is suitable for an acid generator and the photoresist composition containing the salt provides a good photoresist pattern with reduced line edge roughness. Therefore, the photoresist composition is useful for manufacturing the semiconductor production.

What is claimed is:

1. A salt represented by the formula (I):

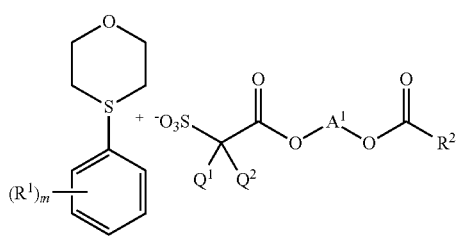

(I)

wherein
$R^1$ each independently represents a C1 to C12 alkyl group in which a methylene group can be replaced by an oxygen atom or a carbonyl group;
$Q^1$ and $Q^2$ each independently represent a fluorine atom or a C1 to C6 perfluoroalkyl group;
$A^1$ represents a lactone ring-containing group which has 4 to 24 carbon atoms;
$R^2$ represents an acid-labile group; and
"m" represents an integer of 0 to 3.

2. The salt according to claim 1 wherein
$A^1$ represents a group which has a norbornanelactone ring.

3. The salt according to claim 1 wherein
$R^2$ is represented by formula (R2-1):

(R2-1)

wherein $R^{2a1}$, $R^{2a2}$ and $R^{2a3}$ independently each represent a C1 to C8 alkyl group, a C3 to C20 alicyclic hydrocarbon group or a group composed of the alkyl group and the alicyclic hydrocarbon group, or $R^{2a1}$ and $R^{2a2}$ can be bonded each other to form a C3 to C20 divalent alicyclic hydrocarbon group together with the carbon atom bonded to $R^{2a1}$ and $R^{2a2}$, and * represents a binding site; or formula (R2-2):

(R2-2)

wherein $R^{2a1'}$ and $R^{2a2'}$ independently each represent a hydrogen atom or a C1 to C12 hydrocarbon group, and $R^{2a3'}$ represents a C1 to C20 hydrocarbon group, or $R^{2a2'}$ and $R^{2a3'}$ can be bonded each other to form a C2 to C20 divalent heterocyclic group together with $X^{2a1'}$ and the carbon atom bonded to $R^{2a2'}$ and $R^{2a3'}$, and a methylene group in the hydrocarbon group and the heterocyclic group can be replaced by —O— or —S—, $X^{2a1'}$ represents an oxygen atom or a sulfur atom, and * represents a binding site.

4. An acid generator which comprises the salt according to claim 1.

5. A photoresist composition which comprises the salt according to claim 1 and a resin having an acid-labile group.

6. A photoresist composition which comprises the salt according to claim 1 and a resin having an acid-labile group, and which further comprises a salt which generates an acid weaker in acidity than an acid generated from the salt according to claim 1.

7. A process for producing a photoresist pattern comprising the following steps (1) to (5):
  (1) a step of applying the photoresist composition according claim 5 on a substrate,
  (2) a step of forming a composition film by conducting drying,
  (3) a step of exposing the composition film to radiation,
  (4) a step of baking the exposed composition film, and
  (5) a step of developing the baked composition film.

* * * * *